United States Patent
Redfearn et al.

(10) Patent No.: US 11,649,445 B2
(45) Date of Patent: *May 16, 2023

(54) COMPOSITIONS COMPRISING DIGESTIVE ENZYMES

(71) Applicant: Clara Foods Co., South San Francisco, CA (US)

(72) Inventors: Halle Redfearn, South San Francisco, CA (US); Harshal Kshirsagar, South San Francisco, CA (US); Kritika Mahadevan, South San Francisco, CA (US); Alexandre Chapeaux, South San Francisco, CA (US); Wesley Rutherford-Jenkins, South San Francisco, CA (US); Joel Andrew Kreps, South San Francisco, CA (US); Isha Joshi, South San Francisco, CA (US)

(73) Assignee: CLARA FOODS CO., Daly City, CA (US)

( * ) Notice: Subject to any disclaimer, the term of this patent is extended or adjusted under 35 U.S.C. 154(b) by 68 days.

This patent is subject to a terminal disclaimer.

(21) Appl. No.: 17/467,601

(22) Filed: Sep. 7, 2021

(65) Prior Publication Data

US 2022/0064619 A1    Mar. 3, 2022

Related U.S. Application Data

(63) Continuation of application No. 17/190,173, filed on Mar. 2, 2021, now Pat. No. 11,142,754, which is a continuation of application No. PCT/US2020/045519, filed on Aug. 7, 2020.

(60) Provisional application No. 62/941,627, filed on Nov. 27, 2019, provisional application No. 62/883,800, filed on Aug. 7, 2019.

(51) Int. Cl.
*C12N 9/50* (2006.01)
*C12P 21/00* (2006.01)
*C12N 9/64* (2006.01)

(52) U.S. Cl.
CPC ............ *C12N 9/50* (2013.01); *C12N 9/6481* (2013.01); *C12P 21/00* (2013.01); *C12Y 304/23001* (2013.01)

(58) Field of Classification Search
None
See application file for complete search history.

(56) References Cited

U.S. PATENT DOCUMENTS

| | | |
|---|---|---|
| 897,192 A | 8/1908 | Joseph |
| 3,251,697 A | 5/1966 | Hans et al. |
| 3,806,608 A | 4/1974 | Perret |
| 4,355,022 A | 10/1982 | Rabussay |
| 4,430,428 A | 2/1984 | Fraser et al. |
| 4,675,201 A | 6/1987 | Lee et al. |
| 4,810,508 A | 3/1989 | Dell'Acqua et al. |
| 4,880,643 A | 11/1989 | Bamforth et al. |
| 5,019,411 A | 5/1991 | Johnson et al. |
| 5,149,521 A | 9/1992 | Hirose et al. |
| 5,283,236 A | 2/1994 | Chiou |
| 5,336,609 A | 8/1994 | Oberto et al. |
| 5,643,792 A | 7/1997 | Okabayashi et al. |
| 5,849,477 A | 12/1998 | O'Malley et al. |
| 6,204,012 B1 | 3/2001 | Hellmuth et al. |
| 6,316,034 B1 | 11/2001 | Daeschel et al. |
| 6,465,254 B1 | 10/2002 | Saito et al. |
| 6,495,344 B1 | 12/2002 | Carr et al. |
| 6,645,739 B2 | 11/2003 | Clark |
| 6,699,691 B2 | 3/2004 | Inan et al. |
| 6,730,499 B1 | 5/2004 | Cregg |
| 6,803,225 B2 | 10/2004 | Contreras et al. |
| 6,875,588 B2 | 4/2005 | Harvey et al. |
| 6,933,146 B2 | 8/2005 | Helliwell et al. |
| 6,994,876 B1 | 2/2006 | Sher et al. |
| 7,029,872 B2 | 4/2006 | Gerngross |
| 7,037,895 B2 | 5/2006 | Assaly et al. |
| 7,078,488 B2 | 7/2006 | Jiang et al. |
| 7,205,018 B2 | 4/2007 | Sherwood et al. |
| 7,252,933 B2 | 8/2007 | Contreras et al. |
| 7,294,507 B2 | 11/2007 | Harvey et al. |
| 7,326,681 B2 | 2/2008 | Gerngross |
| 7,335,761 B2 | 2/2008 | Harvey et al. |
| 7,345,150 B2 | 3/2008 | Assaly et al. |
| 7,348,312 B2 | 3/2008 | Assaly et al. |
| 7,507,573 B2 | 3/2009 | Contreras et al. |
| 7,595,186 B2 | 9/2009 | Gerdes et al. |
| 7,598,055 B2 | 10/2009 | Bobrowicz et al. |
| 7,629,163 B2 | 12/2009 | Gerngross |
| 7,745,200 B2 | 6/2010 | Cregg |
| 7,794,770 B2 | 9/2010 | Sherwood et al. |

(Continued)

FOREIGN PATENT DOCUMENTS

| | | |
|---|---|---|
| AU | 2005264767 A1 | 1/2006 |
| CA | 2574558 A1 | 1/2006 |

(Continued)

OTHER PUBLICATIONS

Alleoni et al. Albumen foam stability and s-ovalbumin contents in eggs coated with whey protein concentrate. Brazilian Journal of Poultry Science, vol. 6, No. 2, pp. 105-110 (Apr.-Jun. 2004).

(Continued)

*Primary Examiner* — Anand U Desai

(74) *Attorney, Agent, or Firm* — Wilson Sonsini Goodrich & Rosati

(57) ABSTRACT

Provided herein are compositions with enhanced protein specific activity, protein combinations and methods for the preparation thereof.

8 Claims, 7 Drawing Sheets

Specification includes a Sequence Listing.

(56) References Cited

U.S. PATENT DOCUMENTS

| | | |
|---|---|---|
| 7,799,363 B2 | 9/2010 | Sherwood et al. |
| 7,842,326 B2 | 11/2010 | Sherwood et al. |
| 7,884,068 B2 | 2/2011 | Assaly et al. |
| 7,897,192 B2 | 3/2011 | Sherwood et al. |
| 7,906,160 B2 | 3/2011 | Sherwood et al. |
| 7,923,430 B2 | 4/2011 | Gerngross |
| 7,923,431 B2 | 4/2011 | Wolff |
| 7,972,809 B2 | 7/2011 | Kobayashi et al. |
| 8,058,053 B2 | 11/2011 | Contreras et al. |
| 8,067,551 B2 | 11/2011 | Gerngross et al. |
| 8,075,919 B2 | 12/2011 | Brown et al. |
| 8,211,691 B2 | 7/2012 | Gerngross |
| 8,222,032 B2 | 7/2012 | Parker et al. |
| 8,227,207 B2 | 7/2012 | Miguel Castro et al. |
| 8,227,436 B2 | 7/2012 | McMillan et al. |
| 8,354,268 B2 | 1/2013 | Contreras et al. |
| 8,445,227 B2 | 5/2013 | Bobrowicz et al. |
| 8,546,136 B2 | 10/2013 | Serber et al. |
| 8,642,017 B2 | 2/2014 | Wagstaff |
| 8,663,971 B2 | 3/2014 | Contreras et al. |
| 8,697,394 B2 | 4/2014 | Bobrowicz et al. |
| 8,753,698 B2 | 6/2014 | Van Amerongen et al. |
| 8,778,659 B2 | 7/2014 | Govindappa et al. |
| 8,809,259 B2 | 8/2014 | Berry et al. |
| 8,815,580 B2 | 8/2014 | Callewaert et al. |
| 8,822,412 B2 | 9/2014 | Berry et al. |
| 8,877,462 B2 | 11/2014 | Gerngross et al. |
| 8,883,445 B2 | 11/2014 | Contreras et al. |
| 8,883,483 B2 | 11/2014 | Gerngross et al. |
| 8,932,825 B2 | 1/2015 | Wildt et al. |
| 8,986,773 B2 | 3/2015 | Beckhoven Van et al. |
| 9,012,175 B2 | 4/2015 | Hartner et al. |
| 9,206,454 B2 | 12/2015 | Weis et al. |
| 9,220,292 B2 | 12/2015 | Jenkins |
| 9,279,129 B2 | 3/2016 | Hartner et al. |
| 9,359,628 B2 | 6/2016 | Contreras et al. |
| 9,598,474 B2 | 3/2017 | Berry et al. |
| 9,605,040 B2 | 3/2017 | Von Maltzahn et al. |
| 9,611,298 B2 | 4/2017 | Berry et al. |
| 9,617,550 B2 | 4/2017 | Gehlsen et al. |
| 9,689,016 B2 | 6/2017 | Marcel et al. |
| 9,700,071 B2 | 7/2017 | Silver et al. |
| 9,757,328 B2 | 9/2017 | Ferrari et al. |
| 10,927,360 B1 | 2/2021 | Redfearn et al. |
| 11,142,754 B2 | 10/2021 | Redfearn et al. |
| 11,279,748 B2 | 3/2022 | Anchel |
| 2002/0098198 A1 | 7/2002 | Watts et al. |
| 2003/0069395 A1 | 4/2003 | Sato et al. |
| 2004/0142906 A1 | 7/2004 | Wang |
| 2004/0231010 A1 | 11/2004 | Murray et al. |
| 2005/0026264 A1 | 2/2005 | Jiang et al. |
| 2005/0090001 A1 | 4/2005 | Parker et al. |
| 2005/0266140 A1 | 12/2005 | Kastenmayer et al. |
| 2006/0228769 A1 | 10/2006 | Yano et al. |
| 2006/0280804 A1 | 12/2006 | Castro et al. |
| 2006/0280840 A1 | 12/2006 | Robertson |
| 2007/0065555 A1 | 3/2007 | Soane et al. |
| 2007/0141139 A1 | 6/2007 | Vandenberg |
| 2007/0231448 A1 | 10/2007 | Takahashi |
| 2008/0166447 A1 | 7/2008 | Strohbehn et al. |
| 2008/0214485 A1 | 9/2008 | McMillan et al. |
| 2008/0260913 A1 | 10/2008 | Orcutt et al. |
| 2009/0029005 A1 | 1/2009 | Van Amerongen et al. |
| 2009/0042249 A1 | 2/2009 | Lubys et al. |
| 2009/0178147 A1 | 7/2009 | Harvey |
| 2009/0191157 A1 | 7/2009 | Albrecht et al. |
| 2009/0263863 A1 | 10/2009 | Contreras et al. |
| 2009/0290005 A1 | 11/2009 | Wanibe et al. |
| 2011/0020811 A1 | 1/2011 | Crowell |
| 2012/0093994 A1 | 4/2012 | Hsieh et al. |
| 2013/0084361 A1 | 4/2013 | Shepheard |
| 2014/0170268 A1 | 6/2014 | Graeber et al. |
| 2014/0345004 A1 | 11/2014 | Callewaert et al. |
| 2014/0356507 A1 | 12/2014 | Tetrick et al. |
| 2014/0369996 A1 | 12/2014 | Ommundsen et al. |
| 2015/0152427 A1 | 6/2015 | Wildt et al. |
| 2015/0191607 A1 | 7/2015 | McDaniel |
| 2015/0284693 A1 | 10/2015 | Nagaoka |
| 2015/0305368 A1 | 10/2015 | Dake et al. |
| 2015/0307562 A1 | 10/2015 | Basu et al. |
| 2016/0024511 A1 | 1/2016 | Tolstorukov et al. |
| 2016/0038428 A1 | 2/2016 | Harel et al. |
| 2016/0039911 A1 | 2/2016 | Lesnicki et al. |
| 2016/0051593 A1 | 2/2016 | Raff |
| 2016/0068880 A1 | 3/2016 | Gerngross |
| 2016/0083722 A1 | 3/2016 | Young et al. |
| 2016/0106137 A1 | 4/2016 | Jenkins |
| 2016/0183567 A1 | 6/2016 | Choi et al. |
| 2017/0029827 A1 | 2/2017 | Gasser et al. |
| 2017/0037418 A1 | 2/2017 | Mattanovich et al. |
| 2017/0159094 A1 | 6/2017 | Natunen et al. |
| 2018/0084814 A1 | 3/2018 | Challakere |
| 2018/0355020 A1 | 12/2018 | Anchel |
| 2020/0138066 A1 | 5/2020 | Anchel |
| 2020/0306342 A1 | 10/2020 | Hamill et al. |
| 2020/0405807 A1 | 12/2020 | Williams et al. |
| 2021/0007384 A1 | 1/2021 | Mahadevan et al. |

FOREIGN PATENT DOCUMENTS

| | | |
|---|---|---|
| CN | 1214729 C | 8/2005 |
| CN | 101022737 A | 8/2007 |
| CN | 101623111 A | 1/2010 |
| CN | 101496575 B | 10/2010 |
| CN | 101496579 B | 10/2010 |
| CN | 102076221 A | 5/2011 |
| CN | 102429307 A | 5/2012 |
| CN | 102308940 B | 8/2012 |
| CN | 102978268 A | 3/2013 |
| CN | 102630865 B | 5/2013 |
| CN | 102008076 B | 7/2013 |
| CN | 103445263 A | 12/2013 |
| CN | 104172168 A | 12/2014 |
| CN | 104172186 A | 12/2014 |
| CN | 104187634 A | 12/2014 |
| CN | 104187666 A | 12/2014 |
| CN | 104256633 A | 1/2015 |
| CN | 104256648 A | 1/2015 |
| CN | 104431285 A | 3/2015 |
| CN | 104694560 A | 6/2015 |
| CN | 104738624 A | 7/2015 |
| CN | 104824674 A | 8/2015 |
| CN | 104855977 A | 8/2015 |
| CN | 104957356 A | 10/2015 |
| CN | 104961823 A | 10/2015 |
| CN | 105012941 A | 11/2015 |
| CN | 105039189 A | 11/2015 |
| CN | 103182074 B | 3/2016 |
| CN | 104146248 B | 6/2016 |
| CN | 105876440 A | 8/2016 |
| CN | 106173829 A | 12/2016 |
| CN | 106259946 A | 1/2017 |
| EP | 0265884 B1 | 12/1992 |
| EP | 1156719 B1 | 5/2003 |
| EP | 1278511 B1 | 8/2004 |
| EP | 1119264 B1 | 3/2005 |
| EP | 1297172 B1 | 11/2005 |
| EP | 1655308 A1 | 5/2006 |
| EP | 1211310 B1 | 12/2006 |
| EP | 1294910 B1 | 11/2008 |
| EP | 1522590 B1 | 8/2009 |
| EP | 2376349 B1 | 10/2012 |
| EP | 2001312 B1 | 5/2014 |
| EP | 2339013 B1 | 7/2014 |
| EP | 2271222 B1 | 2/2015 |
| EP | 2862933 A2 | 4/2015 |
| EP | 2964775 A1 | 1/2016 |
| EP | 3083966 A1 | 10/2016 |
| EP | 1467615 B2 | 3/2017 |
| EP | 3184642 B1 | 5/2019 |
| ES | 2188336 A1 | 6/2003 |
| ES | 2329316 B1 | 10/2010 |
| FR | 2458585 A1 | 1/1981 |
| GB | 1211361 A | 11/1970 |

(56) References Cited

FOREIGN PATENT DOCUMENTS

| | | |
|---|---|---|
| GB | 2033905 B | 10/1982 |
| JP | 2007259805 A | 10/2007 |
| JP | 2008507270 A | 3/2008 |
| JP | 5048487 B2 | 10/2012 |
| JP | 2014171424 A | 9/2014 |
| WO | WO-0200856 A2 | 1/2002 |
| WO | WO-03102187 A1 | 12/2003 |
| WO | WO-2004065593 A1 | 8/2004 |
| WO | WO-2007106731 A2 | 9/2007 |
| WO | WO-2012129036 A2 | 9/2012 |
| WO | WO-2013148330 A1 | 10/2013 |
| WO | WO-2015048339 A2 | 4/2015 |
| WO | WO-2015048342 A2 | 4/2015 |
| WO | WO-2016014900 A2 | 1/2016 |
| WO | WO-2016077457 A1 | 5/2016 |
| WO | WO-2016081645 A1 | 5/2016 |
| WO | WO-2016160655 A1 | 10/2016 |
| WO | WO-2016183056 A1 | 11/2016 |
| WO | WO-2018162557 A2 | 9/2018 |
| WO | WO-2020041483 A1 | 2/2020 |
| WO | WO-2021026510 A1 | 2/2021 |

OTHER PUBLICATIONS

Ambort et al., Perspectives on Mucus Properties and Formation—Lessons from the Biochemical World, Cold Spring Harb Perspect Med; 2:a014159 (9 pages) (2012).
Anumula et al., A comprehensive procedure for preparation of partially methylated alditol acetates from glycoprotein carbohydrates, Anal Biochem., 203(1): 101-108 (1992).
AOAC Official Method 925.09. Solids (Total) and Moisture in Flour, Vacuum Oven Method. Final Action. JAOAC 8, 665(1925); 9, 39, 88(1926); 34, 278(1951). In Official Methods of Analysis of AOAC International, 16th Edition, vol. 2 (Copyright 1995, 1996, 1997, 1998, 1999).
AOAC Official Method 997.02. Yeast and Mold Counts in Foods, Dry Rehydratable Film Method (Petrifilm Method). First Action 1997, Final Action 2000. J AOAC Int 80, 806 (1997). Revised Mar. 2002. AOAC International. One page.
Arntfield et al. Characteristics of heat-induced networks for mixtures of ovalbumin and lysozyme. J Agric. Food Chem 41:2291-2295 (1993).
Aw et al. Can too many copies spoil the broth? Microb Cell Fact. 2013; 12: 128. Published online Dec. 20, 2013. doi: 10.1186/1475-2859-12-128. 9 pages.
Babu. Modulation of Allergic Immune Responses by Engineered Recombinant Ovomucoid Third Domain and Potential Use for Immunotherapy. A Thesis Presented to the Faculty of Graduate Studies of the University of Guelph (Jan. 2006). 162 pages.
Buell et al. Isolation of recombinant plasmids bearing cDNA to hen ovomucoid and lysozyme mRNAs. J Biol Chem 254(18): 9277-9283 (Sep. 25, 1979).
Callewaert et al., Use of HDEL-tagged Trichoderma reesei mannosyl oligosaccharide 1,2-α-D-mannosidase for N-glycan engineering in Pichia pastoris, FEBS Letters, 503:173-178 (2001).
Catterall et al. Primary sequence of ovomucoid messenger RNA as determined from cloned complementary DNA. J Cell Biol 87(2 Pt 1):480-7 (Nov. 1980).
Charoenrat et al. Oxygen-limited fed-batch process: an alternative control for Pichia pastoris recombinant protein processes. Bioprocess Biosyst Eng. Oct. 2005;27(6):399-406. doi: 10.1007/s00449-005-0005-4. Epub Nov. 3, 2005.
Co-pending U.S. Appl. No. 17/147,109, inventors Redfearn; Halle et al., filed Jan. 12, 2021.
Cre-Lox recombination, Wikipedia, downloaded Jun. 12, 2017.
Damasceno et al. An optimized fermentation process for high-level production of a single-chain Fv antibody fragment in Pichia pastoris. Protein Expr Purif. Sep. 2004;37(1):18-26. doi: 10.1016/j.pep.2004.03.019.
Digan et al. Continuous Production of a Novel Lysozyme via Secretion from the Yeast, Pichia pastoris.Bio/Technology 7:160-164(1989).
Duan et al. Effect of oxidative modification on structural and foaming properties of egg white protein. Food Hydrocolloids, vol. 75, pp. 223-228, (Feb. 2018). Available online Aug. 13, 2017.
EP15858729.5 Extended European Report dated Aug. 13, 2018.
EP15858729.5 Partial Supplementary European Search Report dated May 11, 2018.
Fraser et al. Chicken ovalbumin is synthesized and secreted by Escherichia coli. Proc Natl Acad Sci U S A. 75(12): 5936-5940 (Dec. 1978).
Goda et al. Effect of extra N-terminal residues on the stability and folding of human lysozyme expressed in Pichia pastoris. Protein Eng. Apr. 2000;13(4):299-307. doi: 10.1093/protein/13.4.299.
Hughey et al. Antimicrobial activity of lysozyme against bacteria involved in food spoilage and food-borne disease. Appl Environ Microbiol 53(9):2165-70 (Sep. 1987).
Hynes et al. mRNA complexity and egg white protein mRNA content in mature and hormone-withdrawn oviduct. Cell 11:923-932 (Aug. 1977).
International Search Report and Written Opinion dated Feb. 1, 2016 for International Application No. PCT/US2015/060147.
Ito et al. Importance of N-glycosylation positioning for secretion and folding of ovalbumin, Biochemical and Biophysical Research Communications 361(3):725-731 (2007). Available online Jul. 24, 2007.
Ito et al., Structural Characteristics of Hen Egg Ovalbumin Expressed in Yeast Pichia pastoris, Biosci. Biotechnol. Biochem., 69(4): 755-761 (2005).
Jensen. The Basics of Western Blotting. Anat Rec (Hoboken) Mar. 2012;295(3):369-71. doi: 10.1002/ar.22424. Epub Feb. 3, 2012.
Johnson et al. Gelation Properties of Albumen Proteins, Singly and in Combination. Poultry Science 60:2071-2083 (1981).
Julshamin et al. Determination of Arsenic, Cadmium, Mercury, and Lead by Inductively Coupled Plasma/Mass Spectrometry in Foods after Pressure Digestion: NMKL Interlaboratory Study. Journal of AOAC International 90(3):844-856 (2007).
Kato et al. Chicken ovomucoid: determination of its amino acid sequence, determination of the trypsin reactive site, and preparation of all three of its domains. Biochemistry 26(1):193-201 (Jan. 13, 1987).
Krainer et al. Biotechnological advances towards an enhanced peroxidase production in Pichia pastoris. Journal of Biotechnology 233:181-189 (2016).
Lai et al. Molecular structure and flanking nucleotide sequences of the natural chicken ovomucoid gene. Cell 18:829-842 (1979).
Lin et al. Synthesis, Purification, and Active Site Mutagenesis of Recombinant Porcine Pepsinogen. The Journal of Biological Chemistry 264(8):4482-4489 (Mar. 15, 1989).
Lindenmaier et al. Isolation and characterization of the chicken ovomucoid gene. Nucleic Acids Res 7(5):1221-32 (Nov. 10, 1979).
Liu et al. Improved antioxidant activity and physicochemical properties of curcumin by adding ovalbumin and its structural characterization. Food Hydrocolloids 72:304-311 (2017). Available online Jun. 9, 2017.
Lv et al. Structural and Functional Properties of Ovalbumin Glycated by Dry-Heating in the Presence of Maltodextrin. International Journal of Food Properties, 18:1326-1333, 2015. DOI: 10.1080/10942912.2011.620204. Published online Mar. 3, 2015.
Mainwaring et al. Effect of pH on hen egg white lysozyme production and evolution of a recombinant strain of Aspergillus niger. Journal of Biotechnology 75(1):1-10 (Sep. 24, 1999). DOI: 10.1016/S0168-1656(99)00123-6.
Malik et al. A novel fusion protein system for the production of native human pepsinogen in the bacterial periplasm. Protein Expr Purif. Jun. 2006;47(2):662-71. doi: 10.1016/j.pep.2006.02.018. Epub Mar. 20, 2006.
Martinet et al. Modification of the protein glycosylation pathway in the methylotrophic yeast Pichia pastoris. Biotechnology Letters 20(12):1171-1177 (Dec. 1998).
(Martinez, D. et al.) GenBank Accession No. EGR49218. Version No. EGR49218.1. glycoside hydrolase family 79 [Trichoderma

(56) References Cited

OTHER PUBLICATIONS reesei QM6a] (Jul. 25, 2016). Retrieved Dec. 9, 2019 at the world wide web ncbi.nlm.nih.gov/protein/EGR49218.1. 2 pages.
Martinez et al. Genome sequencing and analysis of the biomass-degrading fungus Trichoderma reesei (syn. Hypocrea jecorina). Nat Biotechnol 26(5):553-60 (May 2008). Epub May 4, 2008. doi: 10.1038/nbt1403.
Masuda et al. High yield secretion of the sweet-tasting protein lysozyme from the yeast Pichia pastoris. Protein Expression and Purification 39:35-42 (Nov. 2, 2004).
Mercereau-Puijalon et al. Synthesis of a chicken ovalbumin-like protein in the yeast Saccharomyces cerevisiae. Gene 11:163-167 (1980).
Mine et al. Reduction of antigenicity and allergenicity of genetically modified egg white allergen, ovomucoid third domain. Biochemical and Biophysical Research Communications 302:133-137 (2003).
Mizutani et al., Structural and Functional Characterization of Ovotransferrin Produced by Pichia pastoris, Biosci. Biotechnol. Biochem., 68(2): 376-383 (2004).
Muñoz et al. Cloning of the authentic bovine gene encoding pepsinogen a and its expression in microbial cells. Appl Environ Microbiol. May 2004;70(5):2588-95. doi: 10.1128/aem.70.5.2588-2595.2004.
Nakayama et al., Substrate specificity of α-1,6-mannosyltransferase that initiates N-linked mannose outer chain elongation in Saccharomyces cerevisiae, FEBS Letters, 412(3): 547-550 (1997).
Nilsson et al., Intestinal MUC2 mucin supramolecular topology by packing and release resting on D3 domain assembly, J Mol Biol., 426(14): 2567-2579 (2014).
Ovalbumin, Uptima. Interchim, France. Retrieved Nov. 12, 2020 at the world wide web interchim.fr/ft/R/R5851B.pdf. Published on Apr. 8, 2009 as per Google Search results. 2 pages.
Palmieri et al. [Topical treatment of some dystrophic and inflammatory lesions of the skin and soft tissues.] Archivio per le Scienze Mediche, Oct.-Dec. 1977, 134(4):481-485.
Partow et al. Characterization of different promoters for designing a new expression vector in Saccharomyces cerevisiae. Yeast 27:955-964 (2010). Published online Jul. 12, 2010. DOI: 10.1002/yea.1806.
PCT/US2019/047521 International Search Report and Written Opinion dated Jan. 2, 2020.
PCT/US2020/041720 International Search Report and Written Opinion dated Oct. 8, 2020.
PCT/US2020/045519 International Search Report and Written Opinion dated Oct. 28, 2020.
PCT/US2020/047076 International Search Report and Written Opinion dated Oct. 20, 2020.
Pepsin Activity, Food Chemicals Codex, 11th ed, Pharmacopeial Convention, pp. 1386-1387 (2018). Retrieved Jun. 9, 2020 at the world wide web app.knovel.com/web/view/khtml/print.v/rcid:kpFCCE0042/cid:kt011MEBGL/viewerType:khtml/?notes=off.
Pepsin. Sigma Aldrich Pepsin Product Sheet. Sigma Aldrich. Retrieved Aug. 24, 2020 at the world wide web sigmaaldrich.com/life-science/metabolomics/enzyme-explorer/analytical-enzymes/pepsin.html. 3 pages.
Proctor et al. The chemistry of lysozyme and its use as a food preservative and a pharmaceutical. Crit Rev Food Sci Nutr 26(4):359-95 (1988).
Rajamanickam et al. A novel bi-directional promoter system allows tunable recombinant protein production in Pichia pastoris. Microb Cell Fact 16:152 (2017). 7 pages. DOI 10.1186/s12934-017-0768-8.
Ramat et al. Protein Purification Using Expanded Bed Chromatography. Master of Science in Chemical Engineering Thesis. Worcester Polytechnic Institute Chemical Engineering Department, Winter 2004. 46 pages.
Ramon et al. Sorbitol co-feeding reduces metabolic burden caused by the overexpression of a Rhizopus oryzae lipase in Pichia pastoris. J Biotechnol. May 31, 2007;130(1):39-46. doi: 10.1016/j.jbiotec.2007.02.025. Epub Mar. 3, 2007.

Roth et al., Identification and Quantification of Protein Glycosylation, International Journal of Carbohydrate Chemistry, vol. 2012, Article ID 640923, 10 pages.
Rupa et al. Engineered recombinant ovomucoid third domain can modulate allergenic response in Balb/c mice model. Biochemical and Biophysical Research Communications 342:710-717 (2006).
Rupa et al. Genetically glycosylated ovomucoid third domain can modulate Immunoglobin E antibody production and cytokine response in BALB/c mice. Clinical and Experimental Allergy 37:918-928 (2007).
Rupa et al. Structural and immunological characterization of recombinant ovomucoid expressed in Escherichia coli. Biotechnology Letters 25:427-433 (2003).
Score report to Mcmillan et al per instant SEQ ID No. 1 (U.S. Pat. No. 8,227,436 issued Jul. 24, 2012 & published as 2008/0214485) (Year: 2012).
Score result for SEQ ID No. 3 for Berry et al. (WO2015048339 & Silver et al WO2015048342 published Apr. 2, 2015) (Year: 2015).
Score result for SEQ ID No. 9 for Koentgen (WO2003102187-A1 published Dec. 11, 2003) (Year: 2003).
Shintani et al. Engineering of Porcine Pepsin: Alteration of S1 Substrate Specificity of Pepsin to Those of Fungal Aspartic Proteinases by Site-Directed Mutagenesis. J. Biol. Chem. 1997 272: 18855-18861. doi:10.1074/jbc.272.30.18855.
Takao et al. Production of swine pepsinogen by protein-producing Bacillus brevis carrying swine pepsinogen cDNA. Appl Microbiol Biotechnol 30, 75-80 (1989). DOI: doi.org/10.1007/BF00256000.
Teh et al., Expression and analysis of the glycosylation properties of recombinant human erythropoietin expressed in Pichia pastoris, Genetics and Molecular Biology, 34(3):464-470 (2011).
Thiex et al. Determination of Ash in Animal Feed: AOAC Official Method 942.05 Revisited. J AOAC Int Sep.-Oct. 2012;95(5):1392-7.
Towbin. Western Blotting. In Encyclopedia of Immunology Second Edition, P. J. Delves, ed., pp. 2503-2507 (1998). Elsevier Ltd.
U.S. Appl. No. 15/522,986 Office Action dated Aug. 8, 2019.
U.S. Appl. No. 15/522,986 Office Action dated Jan. 25, 2019.
U.S. Appl. No. 16/701,022 First Action Interview—Office Action dated Sep. 24, 2020.
U.S. Appl. No. 16/891,835 Notice of Allowance dated Dec. 31, 2020.
U.S. Appl. No. 16/891,835 Office Action dated Sep. 4, 2020.
U.S. Appl. No. 16/986,016 Office Action dated Sep. 24, 2020.
U.S. Appl. No. 16/701,022 First Action Interview Pilot Program Pre-Interview Communication dated Apr. 28, 2020.
USP, Pepsin Activity. Ninth Edition of the Food Chemicals Codex (FCC 9). United States Pharmacopeia Convention, Rockville, MD, 2015e, pp. 1410-1411. Retrieved Jun. 9, 2020 at the world wide web app.knovel.com/web/view/khtml/print.v/rcid:kpFCCE0021/cid:kt00U53N01/viewerType:khtml/?notes=off.
Verostek et al. Selective organic precipitation/extraction of released N-glycans following large-scale enzymatic deglycosylation of glycoproteins. Anal Biochem. Feb. 15, 2000;278(2):111-22. doi: 10.1006/abio.1999.4433.
Wang et al. High-level expression of endo-β-N-acetylglucosaminidase H from Streptomyces plicatus in Pichia pastoris and its application for the deglycosylation of glycoproteins. PLoS One. Mar. 17, 2015;10(3):e0120458. doi: 10.1371/journal.pone.0120458. eCollection 2015.
Wang et al. Methanol-Independent Protein Expression by AOX1 Promoter with trans-Acting Elements Engineering and Glucose-Glycerol-Shift Induction in Pichia pastoris. Sci Rep. 2017; 7: 41850. Sci Rep. 2017; 7: 41850.Published online Feb. 2, 2017. doi: 10.1038/srep41850.
Wang et al., Proteomic analysis of fertilized egg white during early incubation, EuPA Open Proteomics, 2: 38-59 (2014).
Wieser et al. Preparation of a Defined Gluten Hydrolysate for Diagnosis and Clinical Investigations of Wheat Hypersensitivities. Nutrients. Oct. 2018; 10(10): 1411. Published online Oct. 2, 2018. doi: 10.3390/nu10101411. 14 pages.

(56) References Cited

OTHER PUBLICATIONS

Xiong et al. Effects of site-specific phosphorylation on the mechanical properties of ovalbumin-based hydrogels. International Journal of Biological Macromolecules 102:1286-1296 (2017). Available online May 8, 2017.

Yamamoto et al. Characterization of *Bacillus* sp. endo-beta-N-acetylglucosaminidase and its application to deglycosylation of hen ovomucoid. Biotechnol Appl Biochem. Dec. 1998;28 ( Pt 3):235-42.

Yoshimasu et al. Soluble expression and purification of porcine pepsinogen from Pichia pastoris. Protein Expression and Purification 25(2):229-236 (2002).

Zhang et al. Fermentation strategies for recombinant protein expression in the methylotrophic yeast *Pichia pastoris*. Biotechnol Bioprocess Eng 5, 275-287 (2000). DOI: doi.org/10.1007/BF02942184.

Zocchi et al. Expression and purification of a recombinant avidin with a lowered isoelectric point in Pichia pastoris. Protein Expression and Purification 32:167-174 (2003).

Correction to Wang et al. High-level expression of endo-β-N-acetylglucosaminidase H from Streptomyces plicatus in Pichia pastoris and its application for the deglycosylation of glycoproteins. PLoS One. Mar. 17, 2015;10(3):e0120458. doi: 10.1371/journal.pone.0120458. eCollection 2015.

U.S. Appl. No. 17/190,173 Notice of Allowance dated Jul. 14, 2021.
U.S. Appl. No. 17/190,173 Notice of Allowance dated Jul. 8, 2021.

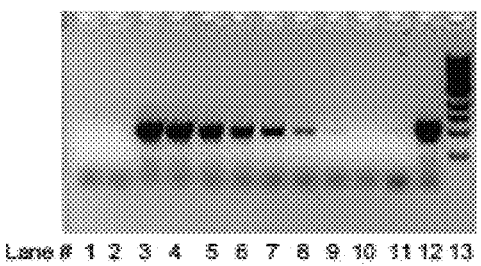

Lane # 1 2 3 4 5 6 7 8 9 10 11 12 13

| Lane # | |
|---|---|
| 1 | 50mg/mL Pepsin PEP19232 |
| 2 | 50mg/mL Pepsin PEP19232 |
| 3 | 1ng pepsinogen plasmid DNA |
| 4 | 0.1ng pepsinogen plasmid DNA |
| 5 | 0.01ng pepsinogen plasmid DNA |
| 6 | 1000fg pepsinogen plasmid DNA |
| 7 | 100fg pepsinogen plasmid DNA |
| 8 | 10fg pepsinogen plasmid DNA |
| 9 | 1fg pepsinogen plasmid DNA |
| 10 | 0.1fg pepsinogen plasmid DNA |
| 11 | negative control |
| 12 | positive control |
| 13 | 1kb DNA ladder |

FIG. 7A

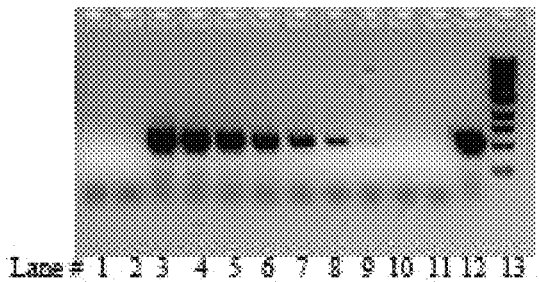

Lane # 1 2 3 4 5 6 7 8 9 10 11 12 13

| Lane # | |
|---|---|
| 1 | 50mg/mL Pepsin PEP19241 |
| 2 | 50mg/mL Pepsin PEP19241 |
| 3 | 1ng pepsinogen plasmid DNA |
| 4 | 0.1ng pepsinogen plasmid DNA |
| 5 | .01ng pepsinogen plasmid DNA |
| 6 | 1000fg pepsinogen plasmid DNA |
| 7 | 100fg pepsinogen plasmid DNA |
| 8 | 10fg pepsinogen plasmid DNA |
| 9 | 1fg pepsinogen plasmid DNA |
| 10 | 0.1fg pepsinogen plasmid DNA |
| 11 | negative control |
| 12 | positive control |
| 13 | 1kb DNA ladder |

FIG. 7B

SEQUENCE LISTING

```
<160> NUMBER OF SEQ ID NOS: 13

<210> SEQ ID NO 1
<211> LENGTH: 385
<212> TYPE: PRT
<213> ORGANISM: Sus scrofa

<400> SEQUENCE: 1

Met Lys Trp Leu Leu Leu Leu Ser Leu Val Val Leu Ser Glu Cys Leu
1               5                   10                  15

Val Lys Val Pro Leu Val Arg Lys Lys Ser Leu Arg Gln Asn Leu Ile
            20                  25                  30

Lys Asn Gly Lys Leu Lys Asp Phe Leu Lys Thr His Lys His Asn Pro
        35                  40                  45

Ala Ser Lys Tyr Phe Pro Glu Ala Ala Ala Leu Ile Gly Asp Glu Pro
    50                  55                  60

Leu Glu Asn Tyr Leu Asp Thr Glu Tyr Phe Gly Thr Ile Gly Ile Gly
65                  70                  75                  80

Thr Pro Ala Gln Asp Phe Thr Val Ile Phe Asp Thr Gly Ser Ser Asn
                85                  90                  95

Leu Trp Val Pro Ser Val Tyr Cys Ser Ser Leu Ala Cys Ser Asp His
```

```
              100                 105                 110
Asn Gln Phe Asn Pro Asp Asp Ser Ser Thr Phe Glu Ala Thr Ser Gln
            115                 120                 125

Glu Leu Ser Ile Thr Tyr Gly Thr Gly Ser Met Thr Gly Ile Leu Gly
    130                 135                 140

Tyr Asp Thr Val Gln Val Gly Gly Ile Ser Asp Thr Asn Gln Ile Phe
145                 150                 155                 160

Gly Leu Ser Glu Thr Glu Pro Gly Ser Phe Leu Tyr Tyr Ala Pro Phe
                165                 170                 175

Asp Gly Ile Leu Gly Leu Ala Tyr Pro Ser Ile Ser Ala Ser Gly Ala
            180                 185                 190

Thr Pro Val Phe Asp Asn Leu Trp Asp Gln Gly Leu Val Ser Gln Asp
        195                 200                 205

Leu Phe Ser Val Tyr Leu Ser Ser Asn Asp Asp Ser Gly Ser Val Val
    210                 215                 220

Leu Leu Gly Gly Ile Asp Ser Ser Tyr Tyr Thr Gly Ser Leu Asn Trp
225                 230                 235                 240

Val Pro Val Ser Val Glu Gly Tyr Trp Gln Ile Thr Leu Asp Ser Ile
                245                 250                 255

Thr Met Asp Gly Glu Thr Ile Ala Cys Ser Gly Gly Cys Gln Ala Ile
            260                 265                 270

Val Asp Thr Gly Thr Ser Leu Leu Thr Gly Pro Thr Ser Ala Ile Ala
        275                 280                 285

Asn Ile Gln Ser Asp Ile Gly Ala Ser Glu Asn Ser Asp Gly Glu Met
    290                 295                 300

Val Ile Ser Cys Ser Ser Ile Asp Ser Leu Pro Asp Ile Val Phe Thr
305                 310                 315                 320

Ile Asn Gly Val Gln Tyr Pro Leu Ser Pro Ser Ala Tyr Ile Leu Gln
                325                 330                 335

Asp Asp Asp Ser Cys Thr Ser Gly Phe Glu Gly Met Asp Val Pro Thr
            340                 345                 350

Ser Ser Gly Glu Leu Trp Ile Leu Gly Asp Val Phe Ile Arg Gln Tyr
        355                 360                 365

Tyr Thr Val Phe Asp Arg Ala Asn Asn Lys Val Gly Leu Ala Pro Val
    370                 375                 380

Ala
385

<210> SEQ ID NO 2
<211> LENGTH: 374
<212> TYPE: PRT
<213> ORGANISM: Sus scrofa

<400> SEQUENCE: 2

Glu Ala Glu Ala Leu Val Lys Val Pro Leu Val Arg Lys Lys Ser Leu
1               5                   10                  15

Arg Gln Asn Leu Ile Lys Asn Gly Lys Leu Lys Asp Phe Leu Lys Thr
            20                  25                  30

His Lys His Asn Pro Ala Ser Lys Tyr Phe Pro Glu Ala Ala Ala Leu
        35                  40                  45

Ile Gly Asp Glu Pro Leu Glu Asn Tyr Leu Asp Thr Glu Tyr Phe Gly
    50                  55                  60

Thr Ile Gly Ile Gly Thr Pro Ala Gln Asp Phe Thr Val Ile Phe Asp
65                  70                  75                  80
```

```
Thr Gly Ser Ser Asn Leu Trp Val Pro Ser Val Tyr Cys Ser Ser Leu
                 85                  90                  95

Ala Cys Ser Asp His Asn Gln Phe Asn Pro Asp Asp Ser Ser Thr Phe
            100                 105                 110

Glu Ala Thr Ser Gln Glu Leu Ser Ile Thr Tyr Gly Thr Gly Ser Met
            115                 120                 125

Thr Gly Ile Leu Gly Tyr Asp Thr Val Gln Val Gly Gly Ile Ser Asp
            130                 135                 140

Thr Asn Gln Ile Phe Gly Leu Ser Glu Thr Glu Pro Gly Ser Phe Leu
145                 150                 155                 160

Tyr Tyr Ala Pro Phe Asp Gly Ile Leu Gly Leu Ala Tyr Pro Ser Ile
                165                 170                 175

Ser Ala Ser Gly Ala Thr Pro Val Phe Asp Asn Leu Trp Asp Gln Gly
            180                 185                 190

Leu Val Ser Gln Asp Leu Phe Ser Val Tyr Leu Ser Ser Asn Asp Asp
            195                 200                 205

Ser Gly Ser Val Val Leu Gly Gly Ile Asp Ser Ser Tyr Tyr Thr
            210                 215                 220

Gly Ser Leu Asn Trp Val Pro Val Ser Val Glu Gly Tyr Trp Gln Ile
225                 230                 235                 240

Thr Leu Asp Ser Ile Thr Met Asp Gly Glu Thr Ile Ala Cys Ser Gly
                245                 250                 255

Gly Cys Gln Ala Ile Val Asp Thr Gly Thr Ser Leu Leu Thr Gly Pro
            260                 265                 270

Thr Ser Ala Ile Ala Asn Ile Gln Ser Asp Ile Gly Ala Ser Glu Asn
            275                 280                 285

Ser Asp Gly Glu Met Val Ile Ser Cys Ser Ser Ile Asp Ser Leu Pro
            290                 295                 300

Asp Ile Val Phe Thr Ile Asn Gly Val Gln Tyr Pro Leu Ser Pro Ser
305                 310                 315                 320

Ala Tyr Ile Leu Gln Asp Asp Ser Cys Thr Ser Gly Phe Glu Gly
            325                 330                 335

Met Asp Val Pro Thr Ser Ser Gly Glu Leu Trp Ile Leu Gly Asp Val
            340                 345                 350

Phe Ile Arg Gln Tyr Tyr Thr Val Phe Asp Arg Ala Asn Asn Lys Val
            355                 360                 365

Gly Leu Ala Pro Val Ala
    370

<210> SEQ ID NO 3
<211> LENGTH: 386
<212> TYPE: PRT
<213> ORGANISM: Ovis aries

<400> SEQUENCE: 3

Met Lys Trp Leu Leu Leu Ala Leu Val Val Leu Ser Glu Cys Ser
1               5                   10                  15

Val Phe Lys Ile Pro Leu Val Lys Lys Ser Leu Arg Gln Asn Leu
             20                  25                  30

Ile Glu Asn Gly Lys Leu Lys Glu Phe Met Lys Thr His Lys Tyr Asn
            35                  40                  45

Leu Gly Ser Lys Tyr Ile Arg Glu Ala Ala Thr Leu Val Ser Asp Gln
    50                  55                  60

Pro Leu Gln Asn Tyr Leu Asp Thr Glu Tyr Phe Gly Thr Ile Gly Ile
65                  70                  75                  80
```

Gly Thr Pro Ala Gln Asp Phe Thr Val Ile Phe Asp Thr Gly Ser Ser
                85                  90                  95

Asn Leu Trp Val Pro Ser Ile Tyr Cys Ser Ser Glu Ala Cys Thr Asn
            100                 105                 110

His Asn Arg Phe Asn Pro Gln Asp Ser Ser Thr Tyr Glu Ala Thr Ser
        115                 120                 125

Glu Thr Leu Ser Ile Thr Tyr Gly Thr Gly Ser Met Thr Gly Ile Leu
    130                 135                 140

Gly Tyr Asp Thr Val Glu Val Gly Gly Ile Ser Asp Thr Asn Gln Ile
145                 150                 155                 160

Phe Gly Leu Ser Glu Thr Glu Pro Gly Ser Phe Leu Tyr Tyr Ala Pro
                165                 170                 175

Phe Asp Gly Ile Leu Gly Leu Ala Tyr Pro Ser Ile Ser Ser Ser Gly
            180                 185                 190

Ala Thr Pro Val Phe Asp Asn Ile Trp Asp Gln Gly Leu Val Ser Gln
        195                 200                 205

Asp Leu Phe Ser Val Tyr Leu Ser Ser Asn Glu Glu Ser Gly Ser Val
    210                 215                 220

Val Met Phe Gly Gly Ile Asp Ser Ser Tyr Tyr Ser Gly Ser Leu Asn
225                 230                 235                 240

Trp Val Pro Val Ser Val Glu Gly Tyr Trp Gln Ile Thr Val Asp Ser
                245                 250                 255

Ile Thr Met Asn Gly Glu Ser Ile Ala Cys Ser Asp Gly Cys Gln Ala
            260                 265                 270

Ile Val Asp Thr Gly Thr Ser Leu Leu Ala Gly Pro Thr Thr Ala Ile
        275                 280                 285

Ser Asn Ile Gln Ser Tyr Ile Gly Ala Ser Glu Asp Ser Ser Gly Glu
    290                 295                 300

Glu Val Ile Ser Cys Ser Ser Ile Asp Ser Leu Pro Asp Ile Val Phe
305                 310                 315                 320

Thr Ile Asn Gly Val Gln Tyr Pro Val Pro Pro Ser Ala Tyr Ile Leu
                325                 330                 335

Gln Asn Asp Asp Val Cys Ser Ser Gly Phe Glu Gly Met Asp Ile Pro
            340                 345                 350

Thr Ser Ser Gly Asp Leu Trp Ile Leu Gly Asp Val Phe Ile Arg Gln
        355                 360                 365

Tyr Phe Thr Val Phe Asp Arg Ala Asn Asn Gln Ile Gly Leu Ala Pro
    370                 375                 380

Val Ala
385

<210> SEQ ID NO 4
<211> LENGTH: 372
<212> TYPE: PRT
<213> ORGANISM: Cervus elaphus hippelaphus

<400> SEQUENCE: 4

Met Leu Arg His Arg Ile Pro Leu Val Lys Lys Ser Leu Arg Arg
1               5                   10                  15

Asn Leu Ile Glu Asn Gly Lys Leu Lys Glu Phe Met Gln Thr His Lys
            20                  25                  30

Tyr Asn Leu Ala Ser Lys Tyr Phe Pro Glu Thr Ala Thr Leu Val Ser
        35                  40                  45

Asp Gln Pro Leu Gln Asn Tyr Leu Asp Thr Glu Tyr Phe Gly Thr Ile

```
            50                  55                  60
Gly Ile Gly Thr Pro Ala Gln Asp Phe Thr Val Ile Phe Asp Thr Gly
 65                  70                  75                  80

Ser Ser Asn Leu Trp Val Pro Ser Ile Tyr Cys Ser Ser Glu Ala Cys
                     85                  90                  95

Thr Asn His Asn Arg Phe Asn Pro Glu Asp Ser Ser Thr Tyr Glu Ala
                100                 105                 110

Thr Ser Glu Thr Leu Ser Ile Thr Tyr Gly Thr Gly Ser Met Thr Gly
                115                 120                 125

Ile Leu Gly Tyr Asp Thr Val Gln Val Gly Gly Ile Thr Asp Thr Asn
            130                 135                 140

Gln Ile Phe Gly Leu Ser Glu Thr Glu Pro Gly Ser Phe Leu Tyr Tyr
145                 150                 155                 160

Ala Pro Phe Asp Gly Ile Leu Gly Leu Ala Tyr Pro Ser Ile Ser Ser
                165                 170                 175

Ser Gly Ala Thr Pro Val Phe Asp Asn Ile Trp Asp Gln Gly Leu Val
                180                 185                 190

Ser Gln Asp Leu Phe Ser Val Tyr Leu Ser Ser Asn Glu Glu Ser Gly
                195                 200                 205

Ser Val Val Ile Phe Gly Asp Ile Asp Ser Ser Tyr Tyr Ser Gly Ser
            210                 215                 220

Leu Asn Trp Val Pro Val Ser Val Glu Gly Tyr Trp Gln Ile Thr Val
225                 230                 235                 240

Asp Ser Ile Thr Met Asn Gly Glu Ser Ile Ala Cys Ser Asp Gly Cys
                245                 250                 255

Gln Ala Ile Val Asp Thr Gly Thr Ser Leu Leu Ala Gly Pro Thr Thr
                260                 265                 270

Ala Ile Ser Asn Ile Gln Ser Tyr Ile Gly Ala Ser Glu Asp Ser Ser
                275                 280                 285

Gly Glu Val Val Ile Ser Cys Ser Ser Ile Asp Ser Leu Pro Asp Val
            290                 295                 300

Val Phe Thr Ile Asn Gly Val Gln Tyr Pro Val Pro Pro Ser Ala Tyr
305                 310                 315                 320

Ile Leu Gln Ser Asp Gly Val Cys Ser Ser Gly Phe Glu Gly Met Asp
                325                 330                 335

Val Ser Thr Ser Ser Gly Asp Leu Trp Ile Leu Gly Asp Val Phe Ile
                340                 345                 350

Arg Gln Tyr Tyr Thr Val Phe Asp Arg Ala Asn Asn Gln Ile Gly Leu
                355                 360                 365

Ala Pro Val Ala
370

<210> SEQ ID NO 5
<211> LENGTH: 386
<212> TYPE: PRT
<213> ORGANISM: Capra hircus

<400> SEQUENCE: 5

Met Lys Trp Leu Leu Leu Leu Ala Leu Val Val Leu Ser Glu Cys Ser
 1               5                  10                  15

Phe Phe Lys Ile Pro Leu Val Lys Lys Ser Leu Arg Gln Asn Leu
                 20                  25                  30

Ile Glu Asn Gly Lys Leu Lys Glu Phe Met Lys Thr His Lys Tyr Asn
             35                  40                  45
```

Leu Gly Ser Lys Tyr Ile Arg Glu Ala Ala Thr Leu Val Ser Asp Gln
    50                  55                  60

Pro Leu Gln Asn Tyr Leu Asp Thr Glu Tyr Phe Gly Thr Ile Gly Ile
 65                  70                  75                  80

Gly Thr Pro Ala Gln Asp Phe Thr Val Ile Phe Asp Thr Gly Ser Ser
                85                  90                  95

Asn Leu Trp Val Pro Ser Val Tyr Cys Ser Ser Glu Ala Cys Thr Asn
                100                 105                 110

His Asn Arg Phe Asn Pro Gln Asp Ser Ser Thr Tyr Glu Ala Thr Ser
                115                 120                 125

Glu Thr Leu Ser Ile Thr Tyr Gly Thr Gly Ser Met Thr Gly Val Leu
    130                 135                 140

Gly Tyr Asp Thr Val Glu Val Gly Gly Ile Ser Asp Thr Asn Gln Ile
145                 150                 155                 160

Phe Gly Leu Ser Glu Thr Glu Pro Gly Ser Phe Leu Tyr Tyr Ala Pro
                165                 170                 175

Phe Asp Gly Ile Leu Gly Leu Ala Tyr Pro Ser Ile Ser Ser Ser Gly
                180                 185                 190

Ala Thr Pro Val Phe Asp Asn Ile Trp Asp Gln Gly Leu Val Ser Gln
    195                 200                 205

Asp Leu Phe Ser Val Tyr Leu Ser Ser Asn Glu Glu Ser Gly Ser Val
    210                 215                 220

Val Ile Phe Gly Gly Ile Asp Ser Ser Tyr Tyr Ser Gly Ser Leu Asn
225                 230                 235                 240

Trp Val Pro Val Ser Val Glu Gly Tyr Trp Gln Ile Thr Val Asp Ser
                245                 250                 255

Ile Thr Met Asn Gly Glu Ser Ile Ala Cys Ser Asp Gly Cys Gln Ala
                260                 265                 270

Ile Val Asp Thr Gly Thr Ser Leu Leu Ala Gly Pro Thr Thr Ala Ile
                275                 280                 285

Ser Asn Ile Gln Ser Tyr Ile Gly Ala Ser Glu Asp Ser Ser Gly Glu
    290                 295                 300

Glu Val Ile Ser Cys Ser Ser Ile Asp Ser Leu Pro Asp Ile Val Phe
305                 310                 315                 320

Thr Ile Asn Gly Val Gln Tyr Pro Val Pro Pro Ser Ala Tyr Ile Leu
                325                 330                 335

Gln Ser Asp Asp Val Cys Ser Ser Gly Phe Glu Gly Met Asp Ile Ser
                340                 345                 350

Thr Ser Ser Gly Asp Leu Trp Ile Leu Gly Asp Val Phe Ile Arg Gln
    355                 360                 365

Tyr Phe Thr Val Phe Asp Arg Ala Asn Asn Gln Ile Gly Leu Ala Pro
    370                 375                 380

Val Ala
385

<210> SEQ ID NO 6
<211> LENGTH: 386
<212> TYPE: PRT
<213> ORGANISM: Bos taurus

<400> SEQUENCE: 6

Met Lys Trp Leu Leu Leu Ala Leu Val Ala Leu Ser Glu Cys Ser
1               5                   10                  15

Val Val Lys Ile Pro Leu Val Lys Lys Ser Leu Arg Gln Asn Leu
                20                  25                  30

Ile Glu Asn Gly Lys Leu Lys Glu Phe Met Arg Thr His Lys Tyr Asn
        35                  40                  45

Leu Gly Ser Lys Tyr Ile Arg Glu Ala Ala Thr Leu Val Ser Glu Gln
 50                  55                  60

Pro Leu Gln Asn Tyr Leu Asp Thr Glu Tyr Phe Gly Thr Ile Gly Ile
 65                  70                  75                  80

Gly Thr Pro Ala Gln Asp Phe Thr Val Ile Phe Asp Thr Gly Ser Ser
                 85                  90                  95

Asn Leu Trp Val Pro Ser Ile Tyr Cys Ser Ser Glu Ala Cys Thr Asn
                100                 105                 110

His Asn Arg Phe Asn Pro Gln Asp Ser Ser Thr Tyr Glu Ala Thr Ser
            115                 120                 125

Glu Thr Leu Ser Ile Thr Tyr Gly Thr Gly Ser Met Thr Gly Ile Leu
130                 135                 140

Gly Tyr Asp Thr Val Gln Val Gly Gly Ile Ser Asp Thr Asn Gln Ile
145                 150                 155                 160

Phe Gly Leu Ser Glu Thr Glu Pro Gly Ser Phe Leu Tyr Tyr Ala Pro
                165                 170                 175

Phe Asp Gly Ile Leu Gly Leu Ala Tyr Pro Ser Ile Ser Ser Ser Gly
            180                 185                 190

Ala Thr Pro Val Phe Asp Asn Ile Trp Asp Gln Gly Leu Val Ser Gln
            195                 200                 205

Asp Leu Phe Ser Val Tyr Leu Ser Ser Asn Glu Glu Ser Gly Ser Val
210                 215                 220

Val Ile Phe Gly Asp Ile Asp Ser Ser Tyr Tyr Ser Gly Ser Leu Asn
225                 230                 235                 240

Trp Val Pro Val Ser Val Glu Gly Tyr Trp Gln Ile Thr Val Asp Ser
                245                 250                 255

Ile Thr Met Asn Gly Glu Ser Ile Ala Cys Ser Asp Gly Cys Gln Ala
            260                 265                 270

Ile Val Asp Thr Gly Thr Ser Leu Leu Ala Gly Pro Thr Thr Ala Ile
            275                 280                 285

Ser Asn Ile Gln Ser Tyr Ile Gly Ala Ser Glu Asp Ser Ser Gly Glu
            290                 295                 300

Val Val Ile Ser Cys Ser Ser Ile Asp Ser Leu Pro Asp Ile Val Phe
305                 310                 315                 320

Thr Ile Asn Gly Val Gln Tyr Pro Val Pro Pro Ser Ala Tyr Ile Leu
                325                 330                 335

Gln Ser Asn Gly Ile Cys Ser Ser Gly Phe Glu Gly Met Asp Ile Ser
            340                 345                 350

Thr Ser Ser Gly Asp Leu Trp Ile Leu Gly Asp Val Phe Ile Arg Gln
            355                 360                 365

Tyr Phe Thr Val Phe Asp Arg Gly Asn Asn Gln Ile Gly Leu Ala Pro
370                 375                 380

Val Ala
385

<210> SEQ ID NO 7
<211> LENGTH: 388
<212> TYPE: PRT
<213> ORGANISM: Homo sapiens

<400> SEQUENCE: 7

Met Lys Trp Leu Leu Leu Leu Gly Leu Val Ala Leu Ser Glu Cys Ile

-continued

```
1               5                   10                  15
Met Tyr Lys Val Pro Leu Ile Arg Lys Lys Ser Leu Arg Arg Thr Leu
                20                  25                  30

Ser Glu Arg Gly Leu Leu Lys Asp Phe Leu Lys Lys His Asn Leu Asn
                35                  40                  45

Pro Ala Arg Lys Tyr Phe Pro Gln Trp Glu Ala Pro Thr Leu Val Asp
                50                  55                  60

Glu Gln Pro Leu Glu Asn Tyr Leu Asp Met Glu Tyr Phe Gly Thr Ile
65                  70                  75                  80

Gly Ile Gly Thr Pro Ala Gln Asp Phe Thr Val Val Phe Asp Thr Gly
                85                  90                  95

Ser Ser Asn Leu Trp Val Pro Ser Val Tyr Cys Ser Ser Leu Ala Cys
                100                 105                 110

Thr Asn His Asn Arg Phe Asn Pro Glu Asp Ser Ser Thr Tyr Gln Ser
                115                 120                 125

Thr Ser Glu Thr Val Ser Ile Thr Tyr Gly Thr Gly Ser Met Thr Gly
                130                 135                 140

Ile Leu Gly Tyr Asp Thr Val Gln Val Gly Gly Ile Ser Asp Thr Asn
145                 150                 155                 160

Gln Ile Phe Gly Leu Ser Glu Thr Glu Pro Gly Ser Phe Leu Tyr Tyr
                165                 170                 175

Ala Pro Phe Asp Gly Ile Leu Gly Leu Ala Tyr Pro Ser Ile Ser Ser
                180                 185                 190

Ser Gly Ala Thr Pro Val Phe Asp Asn Ile Trp Asn Gln Gly Leu Val
                195                 200                 205

Ser Gln Asp Leu Phe Ser Val Tyr Leu Ser Ala Asp Asp Lys Ser Gly
                210                 215                 220

Ser Val Val Ile Phe Gly Gly Ile Asp Ser Ser Tyr Tyr Thr Gly Ser
225                 230                 235                 240

Leu Asn Trp Val Pro Val Thr Val Glu Gly Tyr Trp Gln Ile Thr Val
                245                 250                 255

Asp Ser Ile Thr Met Asn Gly Glu Thr Ile Ala Cys Ala Glu Gly Cys
                260                 265                 270

Gln Ala Ile Val Asp Thr Gly Thr Ser Leu Leu Thr Gly Pro Thr Ser
                275                 280                 285

Pro Ile Ala Asn Ile Gln Ser Asp Ile Gly Ala Ser Glu Asn Ser Asp
                290                 295                 300

Gly Asp Met Val Val Ser Cys Ser Ala Ile Ser Ser Leu Pro Asp Ile
305                 310                 315                 320

Val Phe Thr Ile Asn Gly Val Gln Tyr Pro Val Pro Pro Ser Ala Tyr
                325                 330                 335

Ile Leu Gln Ser Glu Gly Ser Cys Ile Ser Gly Phe Gly Met Gly Asn
                340                 345                 350

Val Pro Thr Glu Ser Gly Glu Leu Trp Ile Leu Gly Asp Val Phe Ile
                355                 360                 365

Arg Gln Tyr Phe Thr Val Phe Asp Arg Ala Asn Asn Gln Val Gly Leu
                370                 375                 380

Ala Pro Val Ala
385

<210> SEQ ID NO 8
<211> LENGTH: 388
<212> TYPE: PRT
<213> ORGANISM: Bos mutus
```

<400> SEQUENCE: 8

```
Arg Ile Met Lys Trp Leu Leu Leu Ala Leu Val Ala Leu Ser Glu
1               5                   10                  15

Cys Ser Val Val Lys Ile Pro Leu Val Lys Lys Ser Leu Arg Gln
                20                  25                  30

Asn Leu Ile Glu Asn Gly Lys Leu Lys Glu Phe Met Arg Thr His Lys
            35                  40                  45

Tyr Asn Leu Gly Ser Lys Tyr Ile Arg Glu Ala Ala Thr Leu Val Ser
    50                  55                  60

Glu Gln Pro Leu Gln Asn Tyr Leu Asp Thr Glu Tyr Phe Gly Thr Ile
65                  70                  75                  80

Gly Ile Gly Thr Pro Ala Gln Asp Phe Thr Val Ile Phe Asp Thr Gly
                85                  90                  95

Ser Ser Asn Leu Trp Val Pro Ser Ile Tyr Cys Ser Ser Glu Ala Cys
                100                 105                 110

Thr Asn His Asn Arg Phe Asn Pro Gln Asp Ser Ser Thr Tyr Glu Ala
            115                 120                 125

Thr Ser Glu Thr Leu Ser Ile Thr Tyr Gly Thr Gly Ser Met Thr Gly
130                 135                 140

Val Leu Gly Tyr Asp Thr Val Gln Val Gly Gly Ile Ser Asp Thr Asn
145                 150                 155                 160

Gln Ile Phe Gly Leu Ser Glu Thr Glu Pro Gly Ser Phe Leu Tyr Tyr
                165                 170                 175

Ala Pro Phe Asp Gly Ile Leu Gly Leu Ala Tyr Pro Ser Ile Ser Ser
            180                 185                 190

Ser Gly Ala Thr Pro Val Phe Asp Asn Ile Trp Asp Gln Gly Leu Val
        195                 200                 205

Ser Gln Asp Leu Phe Ser Val Tyr Leu Ser Ser Asn Glu Glu Ser Gly
210                 215                 220

Ser Val Val Ile Phe Gly Asp Ile Asp Ser Ser Tyr Tyr Ser Gly Ser
225                 230                 235                 240

Leu Asn Trp Val Pro Val Ser Val Glu Gly Tyr Trp Gln Ile Thr Val
                245                 250                 255

Asp Ser Ile Thr Met Asn Gly Glu Ser Ile Ala Cys Ser Asp Gly Cys
            260                 265                 270

Gln Ala Ile Val Asp Thr Gly Thr Ser Leu Leu Ala Gly Pro Thr Thr
        275                 280                 285

Ala Ile Ser Asn Ile Gln Ser Tyr Ile Gly Ala Ser Glu Asp Ser Ser
290                 295                 300

Gly Glu Val Val Ile Ser Cys Ser Ser Ile Asp Ser Leu Pro Asp Ile
305                 310                 315                 320

Val Phe Thr Ile Asn Gly Val Gln Tyr Pro Val Pro Ser Ala Tyr
                325                 330                 335

Ile Leu Gln Ser Asp Gly Ile Cys Ser Ser Gly Phe Glu Gly Met Asp
            340                 345                 350

Ile Ser Thr Ser Ser Gly Asp Leu Trp Ile Leu Gly Asp Val Phe Ile
        355                 360                 365

Arg Gln Tyr Phe Thr Val Phe Asp Arg Gly Asn Asn Gln Ile Gly Leu
370                 375                 380

Ala Pro Val Ala
385
```

<210> SEQ ID NO 9
<211> LENGTH: 386
<212> TYPE: PRT
<213> ORGANISM: Bos indicus

<400> SEQUENCE: 9

Met Lys Trp Leu Leu Leu Ala Leu Val Ala Leu Ser Glu Cys Ser
1               5                   10                  15

Val Val Lys Ile Pro Leu Val Lys Lys Ser Leu Arg Gln Asn Leu
            20                  25                  30

Ile Glu Asn Gly Lys Leu Lys Glu Phe Met Arg Thr His Lys Tyr Asn
            35                  40                  45

Leu Gly Ser Lys Tyr Ile Arg Glu Ala Ala Thr Leu Val Ser Glu Gln
    50                  55                  60

Pro Leu Gln Asn Tyr Leu Asp Thr Glu Tyr Phe Gly Thr Ile Gly Ile
65                  70                  75                  80

Gly Thr Pro Ala Gln Asp Phe Thr Val Ile Phe Asp Thr Gly Ser Ser
                85                  90                  95

Asn Leu Trp Val Pro Ser Ile Tyr Cys Ser Ser Glu Ala Cys Thr Asn
            100                 105                 110

His Asn Arg Phe Asn Pro Gln Asp Ser Ser Thr Tyr Glu Ala Thr Ser
            115                 120                 125

Glu Thr Leu Ser Ile Thr Tyr Gly Thr Gly Ser Met Thr Gly Val Leu
130                 135                 140

Gly Tyr Asp Thr Val Gln Val Gly Gly Ile Ser Asp Thr Asn Gln Ile
145                 150                 155                 160

Phe Gly Leu Ser Glu Thr Glu Pro Gly Ser Phe Leu Tyr Tyr Ala Pro
                165                 170                 175

Phe Asp Gly Ile Leu Gly Leu Ala Tyr Pro Ser Ile Ser Ser Ser Arg
            180                 185                 190

Ala Thr Pro Val Phe Asp Asn Ile Trp Asp Gln Gly Leu Val Ser Gln
            195                 200                 205

Asp Leu Phe Ser Val Tyr Leu Ser Ser Asn Glu Glu Ser Gly Ser Val
210                 215                 220

Val Ile Phe Gly Asp Ile Asp Ser Ser Tyr Tyr Ser Gly Ser Leu Asn
225                 230                 235                 240

Trp Val Pro Val Ser Val Glu Gly Tyr Trp Gln Ile Thr Val Asp Ser
                245                 250                 255

Ile Thr Met Asn Gly Glu Ser Ile Ala Cys Ser Asp Gly Cys Gln Ala
            260                 265                 270

Ile Val Asp Thr Gly Thr Ser Leu Leu Ala Gly Pro Thr Thr Ala Ile
            275                 280                 285

Ser Asn Ile Gln Ser Tyr Ile Gly Ala Ser Glu Asp Ser Ser Gly Glu
290                 295                 300

Val Val Ile Ser Cys Ser Ser Ile Asp Ser Leu Pro Asp Ile Val Phe
305                 310                 315                 320

Thr Ile Asn Gly Val Gln Tyr Pro Val Pro Pro Ser Ala Tyr Ile Leu
                325                 330                 335

Gln Ser Asp Gly Ile Cys Ser Ser Gly Leu Glu Gly Met Asp Ile Ser
            340                 345                 350

Thr Ser Ser Gly Asp Leu Trp Ile Leu Gly Asp Val Phe Ile Arg Gln
            355                 360                 365

Tyr Phe Thr Val Phe Asp Arg Gly Asn Asn Gln Ile Gly Leu Ala Pro
370                 375                 380

Val Ala
385

<210> SEQ ID NO 10
<211> LENGTH: 326
<212> TYPE: PRT
<213> ORGANISM: Sus scrofa

<400> SEQUENCE: 10

Ile Gly Asp Glu Pro Leu Glu Asn Tyr Leu Asp Thr Glu Tyr Phe Gly
1               5                   10                  15

Thr Ile Gly Ile Gly Thr Pro Ala Gln Asp Phe Thr Val Ile Phe Asp
            20                  25                  30

Thr Gly Ser Ser Asn Leu Trp Val Pro Ser Val Tyr Cys Ser Ser Leu
        35                  40                  45

Ala Cys Ser Asp His Asn Gln Phe Asn Pro Asp Ser Ser Thr Phe
    50                  55                  60

Glu Ala Thr Ser Gln Glu Leu Ser Ile Thr Tyr Gly Thr Gly Ser Met
65                  70                  75                  80

Thr Gly Ile Leu Gly Tyr Asp Thr Val Gln Val Gly Gly Ile Ser Asp
                85                  90                  95

Thr Asn Gln Ile Phe Gly Leu Ser Glu Thr Glu Pro Gly Ser Phe Leu
            100                 105                 110

Tyr Tyr Ala Pro Phe Asp Gly Ile Leu Gly Leu Ala Tyr Pro Ser Ile
        115                 120                 125

Ser Ala Ser Gly Ala Thr Pro Val Phe Asp Asn Leu Trp Asp Gln Gly
    130                 135                 140

Leu Val Ser Gln Asp Leu Phe Ser Val Tyr Leu Ser Ser Asn Asp Asp
145                 150                 155                 160

Ser Gly Ser Val Val Leu Leu Gly Gly Ile Asp Ser Ser Tyr Tyr Thr
                165                 170                 175

Gly Ser Leu Asn Trp Val Pro Val Ser Val Glu Gly Tyr Trp Gln Ile
            180                 185                 190

Thr Leu Asp Ser Ile Thr Met Asp Gly Glu Thr Ile Ala Cys Ser Gly
        195                 200                 205

Gly Cys Gln Ala Ile Val Asp Thr Gly Thr Ser Leu Leu Thr Gly Pro
    210                 215                 220

Thr Ser Ala Ile Ala Asn Ile Gln Ser Asp Ile Gly Ala Ser Glu Asn
225                 230                 235                 240

Ser Asp Gly Glu Met Val Ile Ser Cys Ser Ser Ile Asp Ser Leu Pro
                245                 250                 255

Asp Ile Val Phe Thr Ile Asn Gly Val Gln Tyr Pro Leu Ser Pro Ser
            260                 265                 270

Ala Tyr Ile Leu Gln Asp Asp Ser Cys Thr Ser Gly Phe Glu Gly
        275                 280                 285

Met Asp Val Pro Thr Ser Ser Gly Glu Leu Trp Ile Leu Gly Asp Val
    290                 295                 300

Phe Ile Arg Gln Tyr Tyr Thr Val Phe Asp Arg Ala Asn Asn Lys Val
305                 310                 315                 320

Gly Leu Ala Pro Val Ala
                325

<210> SEQ ID NO 11
<211> LENGTH: 4
<212> TYPE: PRT
<213> ORGANISM: Artificial Sequence

```
<220> FEATURE:
<223> OTHER INFORMATION: Peptide

<400> SEQUENCE: 11

Glu Ala Glu Ala
1

<210> SEQ ID NO 12
<211> LENGTH: 31
<212> TYPE: DNA
<213> ORGANISM: Artificial Sequence
<220> FEATURE:
<223> OTHER INFORMATION: Synthetic oliogonucleotide

<400> SEQUENCE: 12
gaagctgaag ctctagtaaa ggtgcctcta g                              31

<210> SEQ ID NO 13
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 13
tgcaacaggt gctagaccca ccttgttgtt ag                             32
```

COMPOSITIONS COMPRISING DIGESTIVE ENZYMES

CROSS-REFERENCE TO RELATED APPLICATIONS

This application is a Continuation Application of U.S. application Ser. No. 17/190,173, filed Mar. 2, 2021, which issued Oct. 12, 2023 as U.S. Pat. No. 11,142,754; U.S. Ser. No. 17/190,173 is a Continuation Application of International Patent Application No. PCT/US2020/045519, filed Aug. 7, 2020, which claims the benefit of U.S. Provisional Application No. 62/883,800, filed Aug. 7, 2019, and U.S. Provisional Application No. 62/941,627, filed Nov. 27, 2019; each of which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Aug. 3, 2020, is named 49160-716.601_ST25.txt and is 33,680 bytes in size.

BACKGROUND OF THE INVENTION

Pepsin is a protease that cleaves polypeptides into smaller units. In nature, pepsin is a digestive enzyme found in the stomach of animals and humans, that helps to digest food. Outside of its naturally-occurring environment, pepsin is used as a processing enzyme in a variety of applications. For example, pepsin can be used to modify food ingredients, it is a component in cheese making, used in the leather industry and also used to prepare antibody fragments used for pharmaceutical and biotechnology applications.

Pepsin is expressed as a zymogen pepsinogen, which has additional amino acids as compared with pepsin. Under non-acidic pH condition, pepsinogen is activimmature, due to the presence of the propeptide. Under acidic pH conditions, pepsinogen can unfold and cleave itself to create the mature form of the enzyme which is pepsin. Typically, the enzyme is extracted from pig stomach. Because the stomach is an acidic environment, the extracted form is primarily the cleaved and active pepsin form.

SUMMARY OF THE INVENTION

An aspect of the present disclosure is a method of producing a high-activity stable pepsin composition. The method comprises steps of (a) providing a microorganism that expresses a recombinant pepsinogen; (b) culturing the microorganism under conditions in which the recombinant pepsinogen polypeptide is expressed and secreted by the microorganism into a growth media; (c) harvesting the growth media and removing the microorganism therefrom to obtain a liquid starting material; (d) lowering the pH of the liquid starting material to less than pH 4.0 to obtain an activated pepsin composition; and (e) raising the pH of the activated pepsin composition to a pH of between about 5.4 and 7.0 to obtain a high-activity stable pepsin composition.

In some embodiments, the method further comprises, after step (d), a step of isolating activated pepsin polypeptide from other proteins and small molecules in the activated pepsin composition and/or, after step (e), a step of isolating activated pepsin polypeptide from other proteins and small molecules in the high-activity stable pepsin composition.

In some embodiments, the high-activity stable pepsin composition comprises an intact and stable proteolytically inactive form of recombinant pepsin.

In some embodiments, the high-activity stable pepsin composition has a specific activity at pH of 2 of at least 20,000 FCC units/mg total protein, e.g., greater than 30,000 FCC units/mg total protein, greater than 40,000 FCC units/mg total protein, greater than 50,000 FCC units/mg total protein, greater than 60,000 FCC units/mg total protein, or greater than 65,000 FCC units/mg total protein. In embodiments, an FCC unit (also referred to herein as a pepsin unit) is defined as that quantity of enzyme that produces the equivalent of 1 μmol of tyrosine per min under the conditions of incubating the enzyme with 2% hemoglobin substrate at pH 1.6 for 10 minutes at 25° C. (see *Food Chemical Codex*, 11*th ed.* (Pharmacopeial Convention. 2018) at 1386-87 "Pepsin Activity").

In some embodiments, the final pH of the high-activity stable pepsin composition is between about 5.4 and 6.0.

In some embodiments, the recombinant pepsinogen is present in at least about 1, 2, 3, 4, 5, 6, 7, 8, 9, 10, 11, 12, 13, 14, 15, 16, 17, 18, 19, 20 or greater than 20 g/liter in the growth medium prior to step (c).

In some embodiments, the growth medium is filtered after step (b), the liquid starting material is filtered after step (c), the activated pepsin composition is filtered after step (d), and/or the high-activity stable pepsin composition is filtered after step (e).

In some embodiments, a recombinant pepsin in the high-activity stable pepsin composition comprises an amino acid sequence of a pig, a sheep, a Central European red deer, a goat, a cow, a human, a yak, or a zebu pepsin.

In some embodiments, the recombinant pepsinogen comprises an amino acid sequence of a pig, a sheep, a Central European red deer, a goat, a cow, a human, a yak, or a zebu pepsinogen.

In some embodiments, the recombinant pepsinogen comprises an amino acid sequence of one of SEQ ID Nos. 1-9 or a sequence with at least 90% identity thereto.

In some embodiments, the microorganism is selected from yeast, filamentous fungi, a *Saccharomyces* species, a bacteria, a *Pichia* species, a *Trichoderma* species and an *Aspergillus* species.

In some embodiments, the microorganism that expresses the recombinant pepsinogen comprises a first inducible promoter which regulates the expression of the recombinant pepsinogen. In some cases, the method further comprises a step of inducing the expression of the recombinant pepsinogen after or at least partially concurrent with the step of culturing the microorganism. In some cases, the microorganism is a *Pichia* species. In some embodiments, the microorganism further comprises a helper factor, e.g., a helper factor that is expressed from a second inducible promoter. In some cases, the first inducible promoter, the second inducible promoter, or both the first and second inducible promoters are induced by methanol.

In some embodiments, the method further comprises a desalting step after the harvesting step and/or the method further comprises a drying step after the harvesting step. The drying step may be spray drying or lyophilization.

In some embodiments, the high-activity stable pepsin composition comprises a recombinant pepsin having an amino acid sequence of SEQ ID NO. 10 or a sequence with at least 90% identity thereto.

Another aspect of the present disclosure is a method of producing a recombinant pepsinogen. The method including steps of (a) providing a microorganism that expresses a recombinant pepsinogen, in which the expressed pepsinogen is secreted by the microorganism into a growth media; (b) culturing the microorganism until the secreted pepsinogen is present in the growth medium in an amount of at least about 1, 2, 3, 4, 5, 6, 7, 8, 9, 10, 11, 12, 13, 14, 15, 16, 17, 18, 19, 20 or greater than 20 g/liter; and (c) harvesting the growth media and removing the microorganism therefrom to obtain a liquid material in which the recombinant pepsinogen is substantially in a proteolytically inactive form.

In some embodiments, the recombinant pepsinogen comprises an amino acid sequence of a pig, a sheep, a Central European red deer, a goat, a cow, a human, a yak, or a zebu pepsinogen.

In some embodiments, the recombinant pepsinogen comprises an amino acid sequence of one of SEQ ID Nos. 1-9 or a sequence with at least 90% identity thereto.

In some embodiments, the microorganism is selected from yeast, filamentous fungi, a *Saccharomyces* species, a bacteria, a *Pichia* species, a *Trichoderma* species and an *Aspergillus* species.

In some embodiments, the microorganism that expresses the recombinant pepsinogen comprises a first inducible promoter which regulates the expression of the recombinant pepsinogen. In some cases, the method further comprises a step of inducing the expression of the recombinant pepsinogen after or at least partially concurrent with the step of culturing the microorganism. In some cases, the microorganism is a *Pichia* species. In some embodiments, the microorganism further comprises a helper factor, e.g., a helper factor that is expressed from a second inducible promoter. In some cases, the first inducible promoter, the second inducible promoter, or both the first and second inducible promoters are induced by methanol.

In some embodiments, the method further comprises a desalting step after the harvesting step and/or the method further comprises a drying step after the harvesting step. The drying step may be spray drying or lyophilization.

In some embodiments, the recombinant pepsinogen that is substantially in the proteolytically inactive form is capable of being activated by reducing the pH or by exposure to an acidic environment to produce a high-activity stable pepsin composition, in which the high-activity stable pepsin composition has a specific activity at pH of 2 of at least 20,000 FCC units/mg total protein, e.g., greater than 30,000 FCC units/mg total protein, greater than 40,000 FCC units/mg total protein, greater than 50,000 FCC units/mg total protein, greater than 60,000 FCC units/mg total protein, or greater than 65,000 FCC units/mg total protein. In embodiments, an FCC unit (also referred to herein as a pepsin unit) is defined as that quantity of enzyme that produces the equivalent of 1 μmol of tyrosine per min under the conditions of incubating the enzyme with 2% hemoglobin substrate at pH 1.6 for 10 minutes at 25° C. (see *Food Chemical Codex*, 11*th ed.* (Pharmacopeial Convention. 2018) at 1386-87 "Pepsin Activity").

In some embodiments, the high-activity stable pepsin composition comprises a recombinant pepsin having an amino acid sequence of SEQ ID NO. 10 or a sequence with at least 90% identity thereto.

In some embodiments, the method further comprises formulating the recombinant pepsinogen with at least one ingredient to create a formulated recombinant pepsinogen composition in liquid (e.g., syrup and gel), powder, pill, tablet or capsule form.

Yet another aspect of the present disclosure is a method of treating a disease or condition of the gastrointestinal tract. The method including steps of (a) providing the recombinant pepsinogen in a formulated composition, in which the pepsinogen is produced by the method according to any herein disclosed method and (b) administering the formulated composition for oral administration; in which upon contact of the formulated composition with an animal gut environment, the pepsinogen is converted to high-activity stable pepsin; and in which the pepsin is effective to treat the disease or condition of the gastrointestinal tract.

In an aspect, the present disclosure provides a composition comprising a recombinant pepsin polypeptide. The composition is (a) free from animal-derived proteins, (b) the pepsin polypeptide is substantially in an intact and stable proteolytically inactive form, (c) the composition has a pH greater than about 5.4, and (d) the composition has a specific activity of at least 20,000 FCC units/mg total protein.

In some embodiments, the composition has a specific activity of at least 30,000 FCC units/mg total protein, at least 40,000 FCC units/mg total protein, at least 50,000 FCC units/mg total protein, at least 60,000 FCC units/mg total protein, or at least 70,000 FCC units/mg total protein.

In some embodiments, the composition has a pH between about 5.4 to about 6.0.

In some embodiments, the proteolytically inactive pepsin polypeptide form is stable in the composition for at least 6 months at room temperature. In some embodiments, the proteolytically inactive pepsin polypeptide form is stable in the composition for at least 6 months at 4° C. In some embodiments, the composition comprises a protein content of at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, or 90% w/w.

In some embodiments, the recombinant pepsin polypeptide comprises an amino acid sequence of a pig, a sheep, a Central European red deer, a goat, a cow, a human, a yak, or a zebu pepsin.

In some embodiments, the recombinant pepsin polypeptide comprises SEQ ID NO: 10, or an amino acid sequence with at least 90% identity thereto.

In some embodiments, the recombinant pepsin polypeptide is produced in a yeast, a filamentous fungi, a *Saccharomyces* species, a bacteria, a *Pichia* species, a *Trichoderma* species, or an *Aspergillus* species. In some cases, the recombinant pepsin polypeptide is produced in a *Pichia* sp.

In some embodiments, the composition is in powdered form. In some embodiments, the proteolytically inactive pepsin polypeptide form is stable in the powdered composition for at least 6 months at room temperature. In some embodiments, the proteolytically inactive pepsin polypeptide form is stable in the powdered composition for at least 6 months at 4° C. In some embodiments, the powdered composition comprises a protein content of at least 15%, 20%, 25%, 30%, 35%, 40%, 45%, 50%, 55%, 60%, 65%, 70%, 75%, 80%, 85%, or 90% w/w. In some embodiments, the powdered composition has a moisture content of less than about 10%. In some embodiments, the recombinant pepsin polypeptide is produced in a yeast, a filamentous fungi, a *Saccharomyces* species, a bacteria, a *Pichia* species, a *Trichoderma* species, or an *Aspergillus* species. In some cases, the recombinant pepsin polypeptide is produced in a *Pichia* sp.

In some embodiments, the composition is in liquid form. In a liquid composition, the concentration of the recombinant pepsin polypeptide may be at least 2 g per liter, at least 5 g per liter, at least 7 g per liter, at least 10 g per liter, at least 15 g per liter, or at least 20 g per liter. In some embodiments, the proteolytically inactive pepsin polypeptide form is stable in the liquid composition for at least 30 days at a temperature of about 4° C. In some embodiments, the recombinant pepsin polypeptide is produced in a yeast, a filamentous fungi, a *Saccharomyces* species, a bacteria, a *Pichia* species, a *Trichoderma* species, or an *Aspergillus* species. In some cases, the recombinant pepsin polypeptide is produced in a *Pichia* sp.

In some embodiments, at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, or 99% w/w of the protein in the composition is recombinant pepsin.

In an aspect, the present disclosure provides a composition comprising a recombinant pepsinogen polypeptide. The composition is (a) free from animal-derived proteins, (b) the pepsinogen polypeptide is substantially in an intact and stable proteolytically inactive form, (c) the composition has a pH greater than about 5.4, and (d) the pepsinogen polypeptide is capable of being activated to a proteolytically active pepsin form that has a specific activity of at least 20,000 FCC units/mg total protein.

In some embodiments, the specific activity is at least 30,000 FCC units/mg total protein, at least 40,000 FCC units/mg total protein, at least 50,000 FCC units/mg total protein, at least 60,000 FCC units/mg total protein, or at least 70,000 FCC units/mg total protein.

In some embodiments, the composition is a liquid and the recombinant pepsinogen polypeptide is present in the composition at least about 1, 2, 3, 4, 5, 6, 7, 8, 9, 10, 11, 12, 13, 14, 15, 16, 17, 18, 19, 20 or greater than 20 g/liter.

In some embodiments, the composition is a powder.

In some embodiments, the recombinant pepsinogen comprises an amino acid sequence of one of SEQ ID NOs: 1-9, or an amino acid sequence with at least 90% identity thereto. In some cases, the amount of pepsin in the composition is less than 10%, 5%, 1%, 0.5%, 0.1% or 0.05% (weight pepsin/weight pepsinogen).

In some embodiments, at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, or 99% w/w of the protein in the composition is recombinant pepsinogen.

In some embodiments, the composition comprises a protein content of at least 1%, 2%, 3%, 4%, 5%, 6%, 7%, 8%, 9%, 10%, 1%, 2%, %13%, %14%, 15%, 20%, 25%, 30%, 35%, 40%, 45%, 50%, 55%, 60%, 65%, 70%, 75%, 80%, 85%, or 90% w/w.

In some embodiments, the composition further comprises at least one ingredient to create a formulated recombinant pepsinogen composition in liquid (e.g., syrup and gel), powder, pill, tablet or capsule form. The formulated composition may be substantially devoid of pepsin. The pepsinogen is capable of activation when exposed to an animal gut environment and/or to a pH of about 2.

In some embodiments, the recombinant pepsinogen polypeptide is produced in a yeast, a filamentous fungi, a *Saccharomyces* species, a bacteria, a *Pichia* species, a *Trichoderma* species or an *Aspergillus* species. In some cases, the recombinant pepsinogen polypeptide is produced in a *Pichia* sp.

An aspect of the present disclosure is a method of producing a stable pepsin composition. The method comprises steps of (a) providing a microorganism that expresses a recombinant pepsinogen; (b) culturing the microorganism under conditions in which the recombinant pepsinogen polypeptide is expressed and secreted by the microorganism into a growth media; (c) harvesting the growth media and removing the microorganism therefrom to obtain a liquid starting material; (d) lowering the pH of the liquid starting material to less than pH 4.0 to obtain an activated pepsin composition; and (e) raising the pH of the activated pepsin composition to a pH of between about 5.4 and 7.0 to obtain a stable pepsin composition. The stable pepsin composition has a specific activity at pH of 2 of between about 100 FCC units/mg total protein and about 19,000 FCC units/mg total protein.

In some embodiments, the method further comprises, after step (d), a step of isolating activated pepsin polypeptide from other proteins and small molecules in the activated pepsin composition and/or, after step (e), a step of isolating activated pepsin polypeptide from other proteins and small molecules in the stable pepsin composition.

In some embodiments, the stable pepsin composition comprises an intact and stable proteolytically inactive form of recombinant pepsin.

In some embodiments, the specific activity at pH of 2 is at least 500 FCC units/mg total protein, at least 1000 FCC units/mg total protein, at least 2000 FCC units/mg total protein, at least 5000 FCC units/mg total protein, at least 10000 FCC units/mg total protein, or at least 15000 FCC units/mg total protein, and less than 20000 FCC units/mg total protein. As examples, the specific activity at pH of 2 is at least 100 FCC units/mg total protein, at least 200 FCC units/mg total protein, at least 300 FCC units/mg total protein, at least 400 FCC units/mg total protein, at least 500 FCC units/mg total protein, at least 600 FCC units/mg total protein, at least 700 FCC units/mg total protein, at least 800 FCC units/mg total protein, at least 900 FCC units/mg total protein, at least 1000 FCC units/mg total protein, at least 1100 FCC units/mg total protein, at least 1200 FCC units/mg total protein, at least 1300 FCC units/mg total protein, at least 1400 FCC units/mg total protein, at least 1500 FCC units/mg total protein, at least 1600 FCC units/mg total protein, at least 1700 FCC units/mg total protein, at least 1800 FCC units/mg total protein, at least 1900 FCC units/mg total protein, at least 2000 FCC units/mg total protein, at least 3000 FCC units/mg total protein, at least 4000 FCC units/mg total protein, at least 5000 FCC units/mg total protein, at least 6000 FCC units/mg total protein, at least 7000 FCC units/mg total protein, at least 8000 FCC units/mg total protein, at least 9000 FCC units/mg total protein, at least 10000 FCC units/mg total protein, at least 11000 FCC units/mg total protein, at least 12000 FCC units/mg total protein, at least 13000 FCC units/mg total protein, at least 14000 FCC units/mg total protein, at least 15000 FCC units/mg total protein, at least 16000 FCC units/mg total protein, at least 17000 FCC units/mg total protein, at least 18000 FCC units/mg total protein, or at least 19000 FCC units/mg total protein and less than 20000 FCC units/mg total protein.

In some embodiments, the final pH of the stable pepsin composition is between about 5.4 and 6.0.

In some embodiments, the recombinant pepsinogen is present in at least about 1, 2, 3, 4, 5, 6, 7, 8, 9, 10, 11, 12, 13, 14, 15, 16, 17, 18, 19, 20 or greater than 20 g/liter in the growth medium prior to step (c).

In some embodiments, the growth medium is filtered after step (b), the liquid starting material is filtered after step (c), the activated pepsin composition is filtered after step (d), and/or the stable pepsin composition is filtered after step (e).

In some embodiments, a recombinant pepsin in the stable pepsin composition comprises an amino acid sequence of a pig, a sheep, a Central European red deer, a goat, a cow, a human, a yak, or a zebu pepsin.

Another aspect of the present disclosure is a method of producing a recombinant pepsinogen. The method comprises steps of (a) providing a microorganism that expresses a recombinant pepsinogen, wherein the expressed pepsinogen is secreted by the microorganism into a growth media; (b) culturing the microorganism until the secreted pepsinogen is present in the growth medium in an amount of at least about 1, 2, 3, 4, 5, 6, 7, 8, 9, 10, 11, 12, 13, 14, 15, 16, 17, 18, 19, 20 or greater than 20 g/liter; and (c) harvesting the growth media and removing the microorganism therefrom to obtain a liquid material in which the recombinant pepsinogen is substantially in a proteolytically inactive form. The recombinant pepsinogen that is substantially in the proteolytically inactive form is capable of being activated by reducing the pH or by exposure to an acidic environment to produce a stable pepsin composition, wherein the stable pepsin composition has a specific activity at pH of 2 of between about 100 FCC units/mg total protein and about 19,000 FCC units/mg total protein.

In some embodiments, the recombinant pepsinogen comprises an amino acid sequence of a pig, a sheep, a Central European red deer, a goat, a cow, a human, a yak, or a zebu pepsinogen.

In some embodiments, the recombinant pepsinogen comprises an amino acid sequence of one of SEQ ID Nos. 1-9 or a sequence with at least 90% identity thereto.

In some embodiments, the microorganism that expresses the recombinant pepsinogen comprises a first inducible promoter which regulates the expression of the recombinant pepsinogen. In some embodiments, the method further comprises a step of inducing the expression of the recombinant pepsinogen after or at least partially concurrent with the step of culturing the microorganism.

In some embodiments, the microorganism is selected from yeast, filamentous fungi, a *Saccharomyces* species, a bacteria, a *Pichia* species, a *Trichoderma* species and an *Aspergillus* species. In some embodiments, the microorganism is a *Pichia* species. In some embodiments, the microorganism further comprises a helper factor. In some embodiments, the helper factor is expressed from a second inducible promoter. In some embodiments, the first inducible promoter, the second inducible promoter, or both the first and second inducible promoters are induced by methanol.

In some embodiments, the method further comprises a desalting step after the harvesting step and/or a drying step after the harvesting step. In some embodiments, the drying step comprises spray drying or lyophilization.

In some embodiments, the specific activity at pH of 2 is at least 500 FCC units/mg total protein, at least 1000 FCC units/mg total protein, at least 2000 FCC units/mg total protein, at least 5000 FCC units/mg total protein, at least 10000 FCC units/mg total protein, or at least 15000 FCC units/mg total protein, and less than 20000 FCC units/mg total protein. As examples, the specific activity at pH of 2 is at least 100 FCC units/mg total protein, at least 200 FCC units/mg total protein, at least 300 FCC units/mg total protein, at least 400 FCC units/mg total protein, at least 500 FCC units/mg total protein, at least 600 FCC units/mg total protein, at least 700 FCC units/mg total protein, at least 800 FCC units/mg total protein, at least 900 FCC units/mg total protein, at least 1000 FCC units/mg total protein, at least 1100 FCC units/mg total protein, at least 1200 FCC units/mg total protein, at least 1300 FCC units/mg total protein, at least 1400 FCC units/mg total protein, at least 1500 FCC units/mg total protein, at least 1600 FCC units/mg total protein, at least 1700 FCC units/mg total protein, at least 1800 FCC units/mg total protein, at least 1900 FCC units/mg total protein, at least 2000 FCC units/mg total protein, at least 3000 FCC units/mg total protein, at least 4000 FCC units/mg total protein, at least 5000 FCC units/mg total protein, at least 6000 FCC units/mg total protein, at least 7000 FCC units/mg total protein, at least 8000 FCC units/mg total protein, at least 9000 FCC units/mg total protein, at least 10000 FCC units/mg total protein, at least 11000 FCC units/mg total protein, at least 12000 FCC units/mg total protein, at least 13000 FCC units/mg total protein, at least 14000 FCC units/mg total protein, at least 15000 FCC units/mg total protein, at least 16000 FCC units/mg total protein, at least 17000 FCC units/mg total protein, at least 18000 FCC units/mg total protein, or at least 19000 FCC units/mg total protein and less than 20000 FCC units/mg total protein.

In some embodiments, the stable pepsin composition comprises a recombinant pepsin having an amino acid sequence of SEQ ID NO. 10 or a sequence with at least 90% identity thereto.

In some embodiments, the method further comprising formulating the recombinant pepsin or recombinant pepsinogen with at least one ingredient to create, respectively, a formulated recombinant pepsin composition or recombinant pepsinogen composition in liquid, powder, pill, tablet, or capsule form. In some embodiments, the liquid is a syrup or a gel Yet another aspect of the present disclosure is composition comprising a recombinant pepsin polypeptide. The composition is (a) free from animal-derived proteins, (b) the pepsin polypeptide is substantially in an intact and stable proteolytically inactive form, (c) the composition has a pH greater than about 5.4, and (d) the composition has a specific activity of between about 100 FCC units/mg total protein and about 19,000 FCC units/mg total protein.

In some embodiments, the specific activity at pH of 2 is at least 500 FCC units/mg total protein, at least 1000 FCC units/mg total protein, at least 2000 FCC units/mg total protein, at least 5000 FCC units/mg total protein, at least 10000 FCC units/mg total protein, or at least 15000 FCC units/mg total protein, and less than 20000 FCC units/mg total protein. In some embodiments, the specific activity at pH of 2 is at least 500 FCC units/mg total protein, at least 1000 FCC units/mg total protein, at least 2000 FCC units/mg total protein, at least 5000 FCC units/mg total protein, at least 10000 FCC units/mg total protein, or at least 15000 FCC units/mg total protein, and less than 20000 FCC units/mg total protein. As examples, the specific activity at pH of 2 is at least 100 FCC units/mg total protein, at least 200 FCC units/mg total protein, at least 300 FCC units/mg total protein, at least 400 FCC units/mg total protein, at least 500 FCC units/mg total protein, at least 600 FCC units/mg total protein, at least 700 FCC units/mg total protein, at least 800 FCC units/mg total protein, at least 900 FCC units/mg total protein, at least 1000 FCC units/mg total protein, at least 1100 FCC units/mg total protein, at least 1200 FCC units/mg total protein, at least 1300 FCC units/mg total protein, at least 1400 FCC units/mg total protein, at least 1500 FCC units/mg total protein, at least 1600 FCC units/mg total protein, at least 1700 FCC units/mg total protein, at least 1800 FCC units/mg total protein, at least 1900 FCC units/mg total protein, at least 2000 FCC units/mg total protein, at least 3000 FCC units/mg total protein, at least 4000 FCC units/mg total protein, at least 5000 FCC units/mg total protein, at least 6000 FCC units/mg total protein, at least 7000 FCC units/mg total protein, at least 8000 FCC units/mg total protein, at least 9000 FCC units/mg total protein, at least 10000 FCC units/mg total protein, at least 11000 FCC units/mg total protein, at least 12000 FCC units/mg total protein, at least 13000 FCC units/mg total protein, at least 14000 FCC units/mg total protein, at least 15000 FCC units/mg total protein, at least 16000 FCC units/mg total protein, at least 17000 FCC units/mg total protein, at least 18000 FCC units/mg total protein, or at least 19000 FCC units/mg total protein and less than 20000 FCC units/mg total protein.

In some embodiments, the composition has a pH between about 5.4 to about 6.0.

In some embodiments, the composition comprises a protein content of at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, or 90% w/w.

In some embodiments, the composition is in powdered form.

In some embodiments, the composition is in liquid form.

In some embodiments, the recombinant pepsin polypeptide is at least 10 mg per liter, at least 100 mg per liter, at least 500 mg per liter, at least 1 g per liter, at least 2 g per liter, at least 5 g per liter, at least 7 g per liter, at least 10 g per liter, at least 15 g per liter, or at least 20 g per liter. As examples, the recombinant pepsin polypeptide is at least 10 mg per liter, at least 20 mg per liter, at least 30 mg per liter, at least 40 mg per liter, at least 50 mg per liter, at least 60 mg per liter, at least 70 mg per liter, at least 80 mg per liter, at least 90 mg per liter, at least 100 mg per liter, at least 200 mg per liter, at least 300 mg per liter, at least 400 mg per liter, at least 500 mg per liter, at least 600 mg per liter, at least 700 mg per liter, at least 800 mg per liter, at least 900 mg per liter, at least 1000 mg per liter, at least 1100 mg per liter, at least 1200 mg per liter, at least 1300 mg per liter, at least 1400 mg per liter, at least 1500 mg per liter, at least 1600 mg per liter, at least 1700 mg per liter, at least 1800 mg per liter, or at least 1900 mg per liter.

In some embodiments, the recombinant pepsin polypeptide comprises an amino acid sequence of a pig, a sheep, a Central European red deer, a goat, a cow, a human, a yak, or a zebu pepsin.

In some embodiments, the recombinant pepsin polypeptide comprises SEQ ID NO: 10, or an amino acid sequence with at least 90% identity thereto.

In some embodiments, the recombinant pepsin polypeptide is produced in a yeast, a filamentous fungi, a *Saccharomyces* species, a bacteria, a *Pichia* species, a *Trichoderma* species, or an *Aspergillus* species. In some embodiments, the recombinant pepsin polypeptide is produced in a *Pichia* sp.

In some embodiments, the liquid form is a syrup or a gel.

In some embodiments, at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, or 99% w/w of the protein in the composition is recombinant pepsin.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Additionally, any composition or method disclosed herein is applicable to any herein-disclosed composition or method. In other words, any aspect or embodiment described herein can be combined with any other aspect or embodiment as disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7A to FIG. 7C show gels showing the absence of nucleic acid encoding pepsinogen in recombinant pepsin compositions, as compared to positive controls of plasmid DNA containing a nucleic acid encoding pepsinogen.

DETAILED DESCRIPTION OF THE INVENTION

Figure 1:
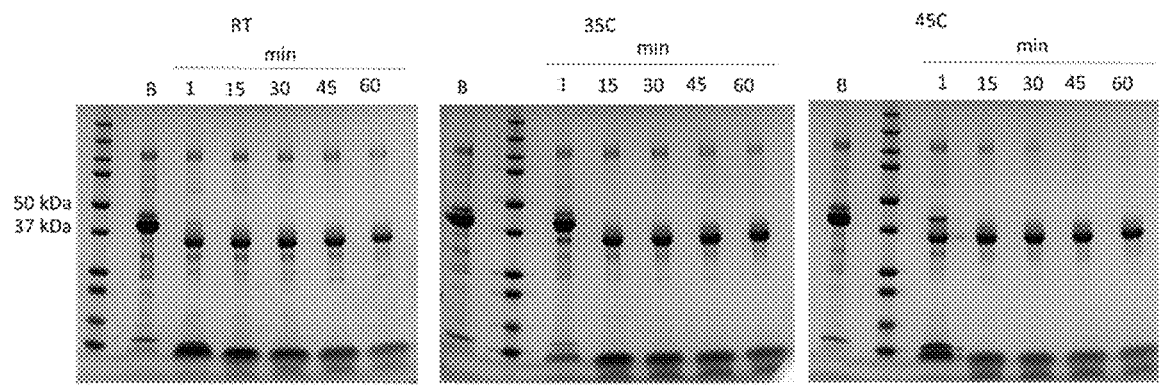
FIG. 1 shows pepsinogen composition at pH 5.95 (lane B) compared to activated pepsin at pH 3.5 at various temperatures after incubation with HCl for 1 minute, 15 minutes, 30 minutes, 45 minutes and 60 minutes.

Provided herein are compositions and methods for making compositions comprising pepsin or comprising pepsinogen.

Expression of Pepsinogen

The protein pepsinogen refers to an immature form of the protein pepsin and carries a propeptide. Upon maturation, the propeptide is cleaved off to produce pepsin. The mature form pepsin may be enzymatically active under certain conditions, such as low pH. In some embodiments, compositions containing the mature form of a recombinant pepsin, when placed under activation conditions, provide a high level of enzymatic activity.

Provided herein are methods for producing compositions of recombinant pepsin that are stable and can be activated to a high level of specific activity.

An aspect of the present disclosure is a method of producing a high-activity stable pepsin composition. The method comprises steps of (a) providing a microorganism that expresses a recombinant pepsinogen; (b) culturing the microorganism under conditions in which the recombinant pepsinogen polypeptide is expressed and secreted by the microorganism into a growth media; (c) harvesting the growth media and removing the microorganism therefrom to obtain a liquid starting material; (d) lowering the pH of the liquid starting material to less than pH 4.0 to obtain an activated pepsin composition; and (e) raising the pH of the activated pepsin composition to a pH of between about 5.4 and 7.0 to obtain a high-activity stable pepsin composition.

In some embodiments, the method further comprises, after step (d), a step of isolating activated pepsin polypeptide from other proteins and small molecules in the activated pepsin composition and/or, after step (e), a step of isolating activated pepsin polypeptide from other proteins and small molecules in the high-activity stable pepsin composition.

Provided herein are methods for producing compositions of recombinant pepsinogen that are stable and can be activated to a high level of specific activity.

Another aspect of the present disclosure is a method of producing a recombinant pepsinogen. The method including steps of (a) providing a microorganism that expresses a recombinant pepsinogen, in which the expressed pepsinogen is secreted by the microorganism into a growth media; (b) culturing the microorganism until the secreted pepsinogen is present in the growth medium in an amount of at least about 1, 2, 3, 4, 5, 6, 7, 8, 9, 10, 11, 12, 13, 14, 15, 16, 17, 18, 19, 20 or greater than 20 g/liter; and (c) harvesting the growth media and removing the microorganism therefrom to obtain a liquid material in which the recombinant pepsinogen is substantially in a proteolytically inactive form.

The methods herein comprise a step of expressing recombinant pepsinogen in a host cell. As used herein, a "host" or "host cell" denotes here any protein production host selected or genetically modified to produce a desired product. Exemplary hosts include fungi, such as filamentous fungi, as well as bacteria, yeast, plant, insect, and mammalian cells. A host cell may be *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum* gloeosporiodes, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium (Talaromyces) emersonii*, *Penicillium funiculosum*, *Penicillium purpurogenum*, *Penicillium roqueforti*, *Pleurotus* spp., *Pleurotus ostreatus*, *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, or *Trichoderma vireus*. A host cell can be an organism that is approved as generally regarded as safe by the U.S. Food and Drug Administration.

A host cell may be a microorganism. In some embodiments, the microorganism is selected from yeast, filamentous fungi, a *Saccharomyces* species, a bacteria, a *Pichia* species, a *Trichoderma* species and an *Aspergillus* species.

In some embodiments, the host cell for recombinant pepsinogen production can be a *Pichia* species (*Komagataella phaffii* and *Komagataella pastoris*), a *Saccharomyces* species, a *Trichoderma* species, a *Pseudomonas* species or an *E. coli* species. In some embodiments, pepsinogen is expressed in a *Pichia* species, such as *Komagataella phaffii*.

The recombinant expression of pepsinogen in a host cell can be regulated by a promoter.

In some embodiments, the microorganism (or host cell) that expresses the recombinant pepsinogen comprises a first inducible promoter which regulates the expression of the recombinant pepsinogen. In some methods of the present disclosure comprise a step of inducing the expression of recombinant pepsinogen after or at least partially concurrent with the step of culturing the microorganism or host cell. In some cases, the first inducible promoter is induced by methanol.

Promoters include, but are not limited to, acu-5, adh1+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbhl), ccg-1, cDNA1, cellular filament polypeptide (cfp), cpc-2, ctr4+, CUP1, dihydroxyacetone synthase (DAS), enolase (ENO, ENO1), formaldehyde dehydrogenase (FLD1), FMD, formate dehydrogenase (FMDH), G1, G6, GAA, GAL1, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, invl+, isocitrate lyase (ICL1), acetohydroxy acid isomeroreductase (ILV5), KAR2, KEX2, β-galactosidase (lac4), LEU2, melO, MET3, methanol oxidase (MOX), nmt1, NSP, pcbC, PET9, peroxin 8 (PEX8), phosphoglycerate kinase (PGK, PGK1), phol, PHO5, PHO89, phosphatidylinositol synthase (PIS1), PYKI, pyruvate kinase (pkil), RPS7, sorbitol dehydrogenase (SDH), 3-phosphoserine aminotransferase (SERI), SSA4, SV40, TEF, translation elongation factor 1 alpha (TEF1), THII1, homoserine kinase (THRI), tpi, TPS1, triose phosphate isomerase (TPI1), XRP2, YPT1. In some embodiments of the methods, the expression of pepsinogen is achieved by regulating the expression using an inducible promoter. Exemplary inducible promoters that can be used for expression include, but are not limited to methanol inducible promoters, such as alcohol oxidase promoters AOX1 and AOX2, and sugar inducible promoters such as glucose-induced and rhamnose regulated promoters.

In some embodiments, the recombinant pepsinogen expressed in the host cell is secreted without conversion to a proteolytically active form such that the recombinant pepsinogen is present in and can be isolated from the growth media in which the host cell is grown. Secretion of recombinant pepsinogen can be achieved by including a secretion signal in the expression construct, which can be cleaved off as the polypeptide is transited through the host cell secretory pathway. In some embodiments, the secretion signal is present at the N-terminus of the recombinant pepsinogen polypeptide (for example, the bolded sequence in SEQ ID NO: 1). Exemplary secretion signals include but are not limited to the mating factor α-factor pro sequence from Cerevisiae, an Ost1 signal sequence, hybrid Ost1-α-factor pro sequence, and synthetic signal sequences. In some embodiments, the pepsinogen expression constructs include a heterologous secretion signal (e.g., not derived natively from pepsinogen). In some embodiments, the pepsinogen expression constructs include a heterologous secretion signal and lack any secretion signal naturally-derived from or associated with a native pepsinogen coding sequence.

Expression constructs can also include transcriptional terminators. Exemplary transcriptional terminator elements include, but are not limited to, acu-5, adh1+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbhl), ccg-1, cDNA1, cellular filament polypeptide (cfp), cpc-2, ctr4+, CUP1, dihydroxyacetone synthase (DAS), enolase (ENO, ENO1), formaldehyde dehydrogenase (FLD1), FMD, formate dehydrogenase (FMDH), G1, G6, GAA, GAL1, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, invl+, isocitrate lyase (ICL1), acetohydroxy acid isomeroreductase (ILV5), KAR2, KEX2, β-galactosidase (lac4), LEU2, melO, MET3, methanol oxidase (MOX), nmt1, NSP, pcbC, PET9, peroxin 8 (PEX8), phosphoglycerate kinase (PGK, PGK1), phol, PHO5, PHO89, phosphatidylinositol synthase (PIS1), PYKI, pyruvate kinase (pkil), RPS7, sorbitol dehydrogenase (SDH), 3-phosphoserine aminotransferase (SERI), SSA4, SV40, TEF, translation elongation factor 1 alpha (TEF1), THI1, homoserine kinase (THRI), tpi, TPS1, triose phosphate isomerase (TPI1), XRP2, and YPT1.

In some embodiments, the microorganism further comprises a helper factor, e.g., a helper factor that is expressed from a second inducible promoter. In some cases, the second inducible promoter is induced by methanol.

Pepsinogen coding sequences for use in producing recombinant pepsinogen include animal pepsinogen sequences such as a pig, a sheep, a Central European red deer, a goat, a cow, a human, a yak, or a zebu pepsinogen. In some embodiments, a pepsinogen sequence is one of SEQ ID NOs: 1-9. The below table also includes the amino acid sequence for an active pepsin (SEQ ID NO: 10).

| Sequence name | SEQ ID NO | Sequence |
|---|---|---|
| Porcine Pepsinogen (Pre-pro form of Pepsin) | 1 | MKWLLLLSLVVLSECLVKVPLVRKKSLRQNLIKNGKLKDFLKTHKHNPASK YFPEAAALIGDEPLENYLDTEYFGTIGIGTPAQDFTVIFDTGSSNLWVPSVY CSSSLACSDHNQFNPDDSSTFEATSQELSITYGTGSMTGILGYDTVQVGGIS DTNQIFGLSETEPGSFLYYAPFDGILGLAYPSISASGATPVFDNLWDQGLVS QDLFSVYLSSNDDSGSVVLLGGIDSSYYTGSLNWVPVSVEGYWQITLDSIT MDGETIACSGGCQAIVDTGTSLLTGPTSAIANIQSDIGASENSDGEMVISC SSIDSLPDIVFTINGVQYPLSPSAYILQDDDSCTSGFEGMDVPTSSGELWIL GDVFIRQYYTVFDRANNKVGLAPVA |
| Pepsinogen sequence (by Edman sequencing) | 2 | EAEALVKVPLVRKKSLRQNLIKNGKLKDFLKTHKHNPASKYFPEAAALIGDE PLENYLDTEYFGTIGIGTPAQDFTVIFDTGSSNLWVPSVYCSSSLACSDHNQF NPDDSSTFEATSQELSITYGTGSMTGILGYDTVQVGGISDTNQIFGLSETEP GSFLYYAPFDGILGLAYPSISASGATPVFDNLWDQGLVSQDLFSVYLSSND DSGSVVLLGGIDSSYYTGSLNWVPVSVEGYWQITLDSITMDGETIACSGGC QAIVDTGTSLLTGPTSAIANIQSDIGASENSDGEMVISCSSIDSLPDIVFTIN GVQYPLSPSAYILQDDDSCTSGFEGMDVPTSSGELWILGDVFIRQYYTVFD RANNKVGLAPVA |
| Ovis aries (sheep) Pepsinogen | 3 | MKWLLLLALVVLSECSVFKIPLVKKKSLRQNLIENGKLKEFMKTHKYNLGSK YIREAATLVSDQPLQNYLDTEYFGTIGIGTPAQDFTVIFDTGSSNLWVPSIY CSSEACTNHNRFNPQDSSTYEATSETLSITYGTGSMTGILGYDTVEVGGISD TNQIFGLSETEPGSFLYYAPFDGILGLAYPSISSSGATPVFDNIWDQGLVSQ DLFSVYLSSNEESGSVVMFGGIDSSYYSGSLNWVPVSVEGYWQITVDSIT MNGESIACSDGCQAIVDTGTSLLAGPTTAISNIQSYIGASEDSSGEEVISCSS IDSLPDIVFTINGVQYPVPPSAYILQNDDVCSSGFEGMDIPTSSGDLWILGD VFIRQYFTVFDRANNQIGLAPVA |
| Cervus elaphus hippelaphus (central European red deer) Pepsinogen | 4 | MLRHRIPLVKKKSLRRNLIENGKLKEFMQTHKYNLASKYFPETATLVSDQPL QNYLDTEYFGTIGIGTPAQDFTVIFDTGSSNLWVPSIYCSSEACTNHNRFN PEDSSTYEATSETLSITYGTGSMTGILGYDTVQVGGITDTNQIFGLSETEPGS FLYYAPFDGILGLAYPSISSSGATPVFDNIWDQGLVSQDLFSVYLSSNEESG SVVIFGDIDSSYYSGSLNWVPVSVEGYWQITVDSITMNGESIACSDGCQAI VDTGTSLLAGPTTAISNIQSYIGASEDSSGEVVISCSSIDSLPDVVFTINGVQY PVPPSAYILQSDGVCSSGFEGMDVSTSSGDLWILGDVFIRQYYTVFDRAN NQIGLAPVA |
| Capra hircus (Goat) Pepsinogen | 5 | MKWLLLLALVVLSECSFFKIPLVKKKSLRQNLIENGKLKEFMKTHKYNLGSK YIREAATLVSDQPLQNYLDTEYFGTIGIGTPAQDFTVIFDTGSSNLWVPSVY CSSEACTNHNRFNPQDSSTYEATSETLSITYGTGSMTGVLGYDTVEVGGIS DTNQIFGLSETEPGSFLYYAPFDGILGLAYPSISSSGATPVFDNIWDQGLVS QDLFSVYLSSNEESGSVVIFGGIDSSYYSGSLNWVPVSVEGYWQITVDSIT MNGESIACSDGCQAIVDTGTSLLAGPTTAISNIQSYIGASEDSSGEEVISCSS IDSLPDIVFTINGVQYPVPPSAYILQSDDVCSSGFEGMDISTSSGDLWILGD VFIRQYFTVFDRANNQIGLAPVA |

-continued

| Sequence name | SEQ ID NO | Sequence |
|---|---|---|
| Bos taurus (Bovine) Pepsinogen | 6 | MKWLLLLALVALSECSVVKIPLVKKKSLRQNLIENGKLKEFMRTHKYNLGSK YIREAATLVSEQPLQNYLDTEYFGTIGIGTPAQDFTVIFDTGSSNLWVPSIYC SSEACTNHNRFNPQDSSTYEATSETLSITYGTGSMTGILGYDTVQVGGISD TNQIFGLSETEPGSFLYYAPFDGILGLAYPSISSSGATPVFDNIWDQGLVSQ DLFSVYLSSNEESGSVVIFGDIDSSYYSGSLNWVPVSVEGYWQITVDSITM NGESIACSDGCQAIVDTGTSLLAGPTTAISNIQSYIGASEDSSGEVVISCSSID SLPDIVFTINGVQYPVPPSAYILQSNGICSSGFEGMDISTSSGDLWILGDVFI RQYFTVFDRGNNQIGLAPVA |
| Homo sapiens Pepsinogen | 7 | MKWLLLLGLVALSECIMYKVPLIRKKSLRRTLSERGLLKDFLKKHNLNPARK YFPQWEAPTLVDEQPLENYLDMEYFGTIGIGTPAQDFTVVFDTGSSNLWV PSVYCSSLACTNHNRFNPEDSSTYQSTSETVSITYGTGSMTGILGYDTVQV GGISDTNQIFGLSETEPGSFLYYAPFDGILGLAYPSISSSGATPVFDNIWNQ GLVSQDLFSVYLSADDKSGSVVIFGGIDSSYYTGSLNWVPVTVEGYWQITV DSITMNGETIACAEGCQAIVDTGTSLLTGPTSPIANIQSDIGASENSDGDM VVSCSAISSLPDIVFTINGVQYPVPPSAYILQSEGSCISGFQGMNVPTESGEL WILGDVFIRQYFTVFDRANNQVGLAPVA |
| Bos mutus (yak) Pepsinogen | 8 | RIMKWLLLLALVALSECSVVKIPLVKKKSLRQNLIENGKLKEFMRTHKYNLG SKYIREAATLVSEQPLQNYLDTEYFGTIGIGTPAQDFTVIFDTGSSNLWVPSI YCSSEACTNHNRFNPQDSSTYEATSETLSITYGTGSMTGVLGYDTVQVGGI SDTNQIFGLSETEPGSFLYYAPFDGILGLAYPSISSSGATPVFDNIWDQGLV SQDLFSVYLSSNEESGSVVIFGDIDSSYYSGSLNWVPVSVEGYWQITVDSIT MNGESIACSDGCQAIVDTGTSLLAGPTTAISNIQSYIGASEDSSGEVVISCSS IDSLPDIVFTINGVQYPVPPSAYILQSDGICSSGFEGMDISTSSGDLWILGDV FIRQYFTVFDRGNNQIGLAPVA |
| Bos indicus (Zebu) Pepsinogen | 9 | MKWLLLLALVALSECSVVKIPLVKKKSLRQNLIENGKLKEFMRTHKYNLGSK YIREAATLVSEQPLQNYLDTEYFGTIGIGTPAQDFTVIFDTGSSNLWVPSIYC SSEACTNHNRFNPQDSSTYEATSETLSITYGTGSMTGVLGYDTVQVGGISD TNQIFGLSETEPGSFLYYAPFDGILGLAYPSISSSRATPVFDNIWDQGLVSQ DLFSVYLSSNEESGSVVIFGDIDSSYYSGSLNWVPVSVEGYWQITVDSITM NGESIACSDGCQAIVDTGTSLLAGPTTAISNIQSYIGASEDSSGEVVISCSSID SLPDIVFTINGVQYPVPPSAYILQSDGICSSGLEGMDISTSSGDLWILGDVFI RQYFTVFDRGNNQIGLAPVA |
| Pepsin sequence (by Edman sequencing, | 10 | IGDEPLENYLDTEYFGTIGIGTPAQDFTVIFDTGSSNLWVPSVYCSSLACSD HNQFNPDDSSTFEATSQELSITYGTGSMTGILGYDTVQVGGISDTNQIFGL SETEPGSFLYYAPFDGILGLAYPSISASGATPVFDNLWDQGLVSQDLFSVYL SSNDDSGSVVLLGGIDSSYYTGSLNWVPVSVEGYWQITLDSITMDGETIAC SGGCQAIVDTGTSLLTGPTSAIANIQSDIGASENSDGEMVISCSSIDSLPDIV FTINGVQYPLSPSAYILQDDDSCTSGFEGMDVPTSSGELWILGDVFIRQYY TVFDRANNKVGLAPVA |

A recombinant pepsinogen or recombinant pepsin can include additional sequences. Expression of recombinant pepsinogen or recombinant pepsin in a host cell, for instance a *Pichia* species, a *Saccharomyces* species, a *Trichoderma* species, a *Pseudomonas* species may lead to an addition of peptides to the pepsinogen or pepsin sequence as part of post-transcriptional or post-translational modifications. Such peptides may not be part of the native pepsinogen or pepsin sequences. For instance, expressing a pepsinogen sequence in a *Pichia* species, such as *Komagataella phaffii* and *Komagataella pastoris* may lead to addition of a peptide at the N-terminus or C-terminus. In some cases, a tetrapeptide EAEA (SEQ ID NO: 11) is added to the N-terminus of the pepsinogen sequence upon expression in a host cell. In some embodiments, pepsinogen or pepsin or both include the amino acids EAEA (SEQ ID NO: 11) at the N-terminus for example, in SEQ ID NO: 2.

A recombinant pepsinogen polypeptide can be a non-naturally occurring variant of a pepsinogen. Such a variant can comprise one or more amino acid insertions, deletions, or substitutions relative to a native pepsinogen sequence.

Similarly, a recombinant pepsin polypeptide can be a non-naturally occurring variant of a pepsin. Such a variant can comprise one or more amino acid insertions, deletions, or substitutions relative to a native pepsin sequence. Variants of pepsinogen can have at least 70%, 75%, 80%, 85%, 90%, 95%, 96%, 97%, 98%, or 99% sequence identity to SEQ ID NOs: 1-9 and variants of pepsin can have at least 70%, 75%, 80%, 85%, 90%, 95%, 96%, 97%, 98%, or 99% sequence identity to SEQ ID NO: 10. The term "sequence identity" as used herein in the context of amino acid sequences is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

In some embodiments, a variant is one that confers additional features, such as reduced allergenicity. Depending on the host organism used to express the recombinant pepsinogen, it can have a glycosylation, acetylation, or phosphorylation pattern different from wildtype pepsinogen and/or wildtype pepsin. For example, the recombinant pepsinogen or recombinant pepsin disclosed herein may or may not be glycosylated, acetylated, or phosphorylated. A recombinant pepsinogen or a recombinant pepsin may have an avian, non-avian, microbial, non-microbial, mammalian, or non-mammalian glycosylation, acetylation, or phosphorylation pattern.

In some cases, recombinant pepsinogen or recombinant pepsin may be deglycosylated (e.g., chemically, enzymatically, Endo-H, PNGase F, O-Glycosidase, Neuraminidase, β1-4 Galactosidase, β-N-acetylglucosaminidase), deacetylated (e.g., protein deacetylase, histone deacetylase, sirtuin), or dephosphorylated (e.g., acid phosphatase, lambda protein phosphatase, calf intestinal phosphatase, alkaline phosphatase). Deglycosylation, deacetylation or dephosphorylation may produce a polypeptide that is more uniform or is capable of producing a composition with less variation.

The pepsinogen expression constructs and host cells (e.g., a microorganism) can be used to produce recombinant pepsinogen in liquid culture, such as in a test tube, shaker flask, or small-scale and large-scale fermentation vessel. In the methods provided herein, the host cell carrying the pepsinogen expression construct can be initially cultured under conditions where there is little to no expression of pepsinogen as a starter culture, and grown to a target cell number, density or for a target duration (referred to as a "growth phase").

In some embodiments of the method, after such growth phase, recombinant pepsinogen expression can be initiated ("expression phase"). In some embodiments, expression is initiated such as by induction of an inducible promoter, e.g., a promoter induced by methanol. In some embodiments, expression is initiated such as by release of a repressible promoter or by removal of a blocking sequence, protein binding or other form of repression of expression. In other cases, the expression of pepsinogen can be driven by a constitutive promoter.

In some embodiments, the pH of the culture media is controlled during the growth phase, the expression phase, or during both phases. In some embodiments, the pH of the growth phase is about pH 5. In some embodiments, the pH of the growth media is about 5, and then is increased to about pH 6 before the expression phase.

After initiation of the expression phase, the culturing is continued for a target length of time or up until a target amount of recombinant pepsinogen is recovered from the culture media. In the methods disclosed herein, the cultured host organism can provide a titer of at least about 1, 2, 3, 4, 5, 6, 7, 8, 9, 10, 11, 12, 13, 14, 15, 16, 17, 18, 19 or 20 g/L of total protein or greater than 20 g/liter.

By producing pepsinogen recombinantly, the ultimate recombinant pepsin composition will comprise fewer additional and contaminating proteins, for example when compared to extracting pepsin from natural sources, e.g. from a pig's digestive system. In particular, when extracting pepsin from natural sources, contaminating animal proteins will be included in the extract. In embodiments, a recombinant pepsin composition may comprise less than 5% of impurities/contaminating proteins, i.e., non-pepsin proteins. For example, a recombinant pepsin composition may comprise less than 4.5%, 4.0%, 3.5%, 3.0%, 2.5%, 2.0%, 1.5%, 1.0%, 0.5% or less of contaminating proteins. In various embodiments, a recombinant pepsin composition comprises little to no contaminating animal proteins. In some embodiments, a recombinant pepsin composition is free from animal-derived proteins.

In some embodiments, the method further comprises steps of isolating pepsinogen and/or activated pepsin polypeptide from other proteins and small molecules present in a growth medium, a liquid starting medium, and/or a composition.

Recombinant pepsin and/or recombinant pepsinogen compositions of the present disclosure may include additional proteins, e.g., proteins that are added to promote desirable qualities and features to a composition.

Pepsinogen Protein Isolation and Conversion to Pepsin

The methods herein can include one or more steps whereby the recombinant pepsinogen is separated from the host cell and other culture media components. Host cells, some host cell proteins, and cellular debris can be removed through centrifugation, filtration or a combination thereof. However, such gross separation of the host cell and other culture media components does not result in a purified recombinant pepsinogen composition and/or an isolated recombinant pepsinogen composition as additional proteins and other molecules remain in the composition that contains the pepsinogen.

In some embodiments, the growth medium is filtered and/or centrifuged after culturing a microorganism, a liquid starting material is filtered and/or centrifuged after harvesting a growth medium, and/or a final or penultimate composition is filtered and/or centrifuged.

In some embodiments, a composition comprises recombinant pepsinogen in its stable zymogen (inactive) form that can be activated under specific conditions. Such compositions provide improved stability and control of activity upon conversion to a proteolytically active form as compared to the proteolytically active enzyme extracted from animal gut and other sources.

In some embodiments, a composition contains recombinant pepsinogen in a stable, inactive form and the compositions are substantially recombinant pepsinogen and contain low amounts or little to no recombinant pepsin. In some embodiments, the compositions have a ratio of recombinant pepsinogen to recombinant pepsin of at least about 10:1, 100:1, 1000:1 or greater than 1000:1.

In some embodiments, methods for producing a composition of the present disclosure include one or more pH shift steps to convert recombinant pepsinogen to recombinant pepsin and to maintain recombinant pepsin in a stable form. The recombinant pepsinogen compositions disclosed herein can be activated to convert the recombinant pepsinogen to the pepsin form of the enzyme, such as by lowering the pH of the composition, by addition of an acidic ingredient, addition of acid, or by placing the composition in an acidic environment. In some embodiments, in a first pH shift step, the pH can be lowered below pH 5, such as to about pH 4 or pH 3.5 or pH 2.0 for a period of time to convert recombinant pepsinogen to recombinant pepsin. Such a pH shift can be performed at room temperature or at about 20° C. to about 25° C. or at a temperature at or about 10° C.-45° C. In some embodiments, the duration for treating at a pH below 5, e.g., about pH 4 or about pH 3.5, is about 1, 2, 3, 4, 5, 6, 7, 8, 9, 10, 15, 20, 25, 30, 35, 40, 45, 50, 55 or 60 minutes. In some embodiments, the duration for treating at a pH below 5, e.g., about pH 4 or about pH 3.5, is about 1 hour, 2 hours, 2.25 hours, or 2.5 hours.

In embodiments, growth media comprising recombinant pepsinogen is harvested and cellular material is removed, thereby obtaining a liquid starting material. The pH of the liquid starting material is lowered to less than pH 4.0 (such as pH 3.5) to obtain an activated recombinant pepsin composition. The pH may be lowered by the addition of an acid, for example hydrochloric acid, phosphoric acid, sulfuric acid, or nitric acid. Thus, in embodiments, it is unnecessary to first purify the recombinant pepsinogen, e.g., from a growth media, before converting the recombinant pepsinogen to recombinant pepsin. Surprisingly, a purer recombinant pepsin product which has higher activity is provided by converting newly-synthesized recombinant pepsinogen to recombinant pepsin and subsequently purifying the recombinant pepsin rather than purifying the recombinant pepsinogen.

In embodiments, the compositions are composed of primarily recombinant pepsin and have little or no detectable pepsinogen or other intermediates derived from pepsinogen. In some embodiments, the amount of recombinant pepsinogen in the composition comprising recombinant pepsin is less than about 10%, 5%, 1%, 0.5%, 0.1% or 0.05% (weight pepsinogen/weight pepsin).

In some embodiments, at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, or 99% w/w of the protein in the composition is recombinant pepsin.

In some embodiments, the composition comprises a protein content of at least 1%, 2%, 3%, 4%, 5%, 6%, 7%, 8%, 9%, 10%, 11%, 12%, 3%, 14%, %15%, 20%, 25%, 30%, 35%, 40%, 45%, 50%, 55%, 60%, 65%, 70%, 75%, 80%, 85%, or 90% w/w.

In some embodiments, active recombinant pepsin is then converted to stable (e.g., inactive) recombinant pepsin, such as by raising the pH. In some embodiments, a second pH shift step raises the pH to at least has a pH 5.4, e.g., about pH 6 or above pH 6, following the first pH shift step to maintain pepsin in a stable form that is enzymatically inactive when held at such pH conditions.

Raising the pH of a pepsin composition to greater than 5.4, e.g., about pH 6.0, obtains a stable recombinant pepsin composition. By stable is meant, in part, that the recombinant pepsin does not substantially digest itself and remains in an intact form. The compositions of the present disclosure comprise recombinant pepsins that are intact and in a stable proteolytically inactive form. This form is not present in natural pepsin because natural pepsin compositions self-digest over time (i.e., they are not stable in maintaining a substantially intact form of pepsin in the composition). Such an intact and stable proteolytically inactive form of the recombinant pepsin compositions provided herein advantageously allows long-term storage (at room temperature or at refrigeration temperature) of compositions of the present disclosure. Long-term storage may be for a month, two months, three months, four months, five months, six months, seven months, eight months, nine months, ten months, eleven months, twelve months or longer. After such long-term storage, the recombinant pepsin can be activated by lowering the pH of a composition. Enzymic activity of the re-activated recombinant pepsin is maintained after long-term storage, e.g., within about 15% of a composition's original activity.

In some embodiments, following the pH shift steps, the stable recombinant pepsin can be purified. For example, by removing contaminating proteins, carbohydrates, lipids, salts, nucleic acids, small molecules, cells (e.g., microorganism), or cell components (e.g., cellular debris). In embodiments which include a step of "harvesting the growth media and removing the microorganism therefrom", the removal of the microorganism may be a consequence of harvesting the growth medium and not a separate step of "removing". For example, the growth medium may be filtered and/or centrifuged during harvesting; either of these would remove microorganisms in the growth medium. Alternately, "removing the microorganism" may be a distinct step from the harvesting the growth medium; this distinct step purposefully removes the microorganism.

In some embodiments, following the pH shift steps, the stable pepsin can be concentrated, such as to a 2×, 3×, 4×, 5×, 10× or greater than 10× concentrated form. In some embodiments, the concentrate is maintained as a liquid. In some embodiments, the concentrate is lyophilized or dried and stored as a solid or powder. In some embodiments, the stable pepsin concentrate can be diluted for formulation, for final product production or for consumption. In some embodiments, the diluted stable pepsin is maintained at a pH to about pH 6 (e.g., 5.4 to 6.0) or above pH 6. In some embodiments, the diluent for the pepsinogen composition is NaCl.

In some embodiments, stable recombinant pepsin is subsequently converted to an enzymatically active form, such as by lowering the pH ("activated recombinant pepsin composition"). Activated recombinant pepsin compositions provided herein can have a high specific activity.

In some embodiments, the method further comprises a step of isolating the activated pepsin polypeptide from contaminating proteins, carbohydrates, lipids, salts, nucleic acids, and small molecules in the liquid starting material and the lowering of the pH of the liquid starting material may be performed after the isolating the recombinant pepsin polypeptide to provide an activated recombinant pepsin composition. In some embodiments, the isolating of the activated pepsin polypeptide occurs after a step of lowering the pH of the liquid starting material to less than pH 4.0 to obtain an activated pepsin composition and a step of raising the activated pepsin composition to a pH of about 6.0 to obtain a high-activity stable pepsin composition.

For example, a stable and inactive recombinant pepsin composition, which has a pH of about 6 (e.g., between 5.4 and 6.0), can be converted into an active recombinant pepsin composition by lowering the pH of the composition to less than pH 4.0.

In some embodiments, a method further comprises a desalting step after a harvesting pepsinogen or pepsin and/or the method may further comprise a drying step after the harvesting. The drying step may be spray drying or lyophilization.

Compositions and Uses of Compositions

Recombinant pepsin compositions can include stable recombinant pepsin, a concentrate of stable recombinant pepsin, a dilution of stable recombinant pepsin, as well as mixtures of stable recombinant pepsin with one or more additional ingredients. Recombinant pepsin compositions of the present disclosure may include additional proteins, e.g., proteins added to promote desirable qualities and features to a composition.

In an aspect, the present disclosure provides a composition comprising a recombinant pepsin polypeptide. The composition is (a) free from animal-derived proteins, (b) the pepsin polypeptide is substantially in an intact and stable proteolytically inactive form, (c) the composition has a pH greater than about 5.4, and (d) the composition has a specific activity of at least 20,000 FCC units/mg total protein.

In some embodiments, a composition comprising recombinant pepsin is substantially free from animal-derived proteins.

Recombinant pepsin compositions also can include activated recombinant pepsin compositions, a dilution of activated recombinant pepsin compositions, as well as mixtures of activated recombinant pepsin compositions with one or more additional ingredients. Recombinant pepsin compositions of the present disclosure may include additional proteins, e.g., proteins added to promote desirable qualities and features to a composition.

In some embodiments, the recombinant pepsin compositions are substantially free contaminating proteins, carbohydrates, lipids, salts, nucleic acids, and small molecules.

In some embodiments, the activated recombinant pepsin compositions disclosed herein (after the pH has been lowered) provide a specific activity that is higher than commercially-available pepsin-related products. In some embodiments, the activated recombinant pepsin composition provided herein have a specific activity that is at least about 25%, 30%, 35%, 40%, 45%, 50%, 60%, 70%, 75%, 80%, 90% 100%, 150%, 200%, or 250% higher than a commercially-available pepsin-related product. In some embodiments, the activated recombinant pepsin composition provided herein have a specific activity that is at least about 1.2, 1.5, 1.7, 2, 2.5, 3, 3.5 or greater than 3.5-fold higher than a commercially-available pepsin-related product.

In some embodiments, a recombinant pepsin composition, such as a recombinant pepsin composition comprising a pepsin polypeptide substantially in an intact and stable proteolytically inactive form, is in a powdered form of the composition. In some embodiments, a recombinant pepsin composition, such as a recombinant pepsin composition comprising a pepsin polypeptide substantially in an intact and stable proteolytically inactive form, is in a liquid form of the composition. The proteolytically inactive pepsin polypeptide form (in a powdered or a liquid composition) may be stable for at least six months at room temperature, e.g., six months, seven months, eight months, nine months, ten months, eleven months, twelve months or longer. The proteolytically inactive pepsin polypeptide form (in a powdered or a liquid composition) may be stable in the composition for at least six months at 4° C., e.g., six months, seven months, eight months, nine months, ten months, eleven months, twelve months or longer. A powdered composition may have a moisture content of less than about 10%, e.g., less than 10%, less than 9%, less than 8%, less than 7%, less than 6%, less than 5%, or lower. In some embodiments, a composition comprises a protein content of at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, or 90% w/w; the remaining substances in a composition may be additional organic matter.

In embodiments, the compositions are composed of primarily recombinant pepsin and have little or no detectable pepsinogen or other intermediates derived from pepsinogen. In some embodiments, the amount of recombinant pepsinogen in the composition comprising recombinant pepsin is less than about 10%, 5%, 1%, 0.5%, 0.1% or 0.05% (weight pepsinogen/weight pepsin).

In some embodiments, at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, or 99% w/w of the protein in the composition is recombinant pepsin.

In some embodiments, a recombinant pepsin composition has a specific activity at pH of 2 of at least 20,000 FCC units/mg total protein (expressed as units of pepsin activity per total of all protein in the composition), e.g., of at least 25,000 FCC units/mg total protein, of at least 30,000 FCC units/mg total protein, of at least 35,000 FCC units/mg total protein, at least 40,000 FCC units/mg total protein, of at least 45,000 FCC units/mg total protein, at least 50,000 FCC units/mg total protein, of at least 55,000 FCC units/mg total protein, at least 60,000 FCC units/mg total protein, of at least 65,000 FCC units/mg total protein, and at least 70,000 FCC units/mg total protein. The FCC units/mg total protein may relate to the total amount of recombinant pepsin protein alone. As mentioned above, a recombinant pepsin compositions of the present disclosure may include additional proteins; thus, the FCC units/mg total protein may relate to the recombinant pepsin protein and the additional proteins. An FCC unit (also referred to herein as a pepsin unit) is defined as that quantity of enzyme that produces the equivalent of 1 µmol of tyrosine per min under the conditions of incubating the enzyme with 2% hemoglobin substrate at pH 1.6 for 10 minutes at 25° C. (see *Food Chemical Codex*, 11*th* ed. (Pharmacopeial Convention. 2018) at 1386-87 "Pepsin Activity").

In some embodiments, a powdered recombinant pepsin composition has a specific activity at pH of 2 of at least 20,000 FCC units/mg total powder, e.g., of at least 25,000 FCC units/mg total powder, of at least 30,000 FCC units/mg total powder, of at least 35,000 FCC units/mg total powder, at least 40,000 FCC units/mg total powder, at least 45,000 FCC units/mg total powder, at least 50,000 FCC units/mg total powder, at least 55,000 FCC units/mg total powder, at least 60,000 FCC units/mg total powder, at least 65,000 FCC units/mg total powder, and at least 70,000 FCC units/mg total powder. As used herein, an FCC unit (also referred to herein as a pepsin unit) is defined as that quantity of enzyme that produces the equivalent of 1 µmol of tyrosine per min under the conditions of incubating the enzyme with 2% hemoglobin substrate at pH 1.6 for 10 minutes at 25° C. (see *Food Chemical Codex*, 11*th* ed. (Pharmacopeial Convention. 2018) at 1386-87 "Pepsin Activity").

In some embodiments, the recombinant pepsin polypeptide in a composition comprises SEQ ID NO: 10, or an amino acid sequence with at least 90% identity thereto.

In another aspect, the present disclosure provides a composition comprising a recombinant pepsinogen polypeptide. The composition is (a) free from animal-derived proteins, (b) the pepsinogen polypeptide is substantially in an intact and stable proteolytically inactive form, (c) the composition has a pH greater than about 5.4, and (d) the pepsinogen polypeptide is capable of being activated to a proteolytically active pepsin form that has a specific activity of at least 20,000 FCC units/mg total protein.

Recombinant pepsinogen compositions can include recombinant pepsinogen, a concentrate of recombinant pepsinogen, as well as mixtures of recombinant pepsinogen with one or more additional ingredients.

In some embodiments, the recombinant pepsinogen compositions disclosed herein, have a significantly lower amount of pepsin in the composition initially, e.g., such as when secreted from a host cell, as compared to commercially-available pepsin-related products. In some embodiments, the amount of recombinant pepsin in the recombinant pepsinogen compositions disclosed herein is less than 50%, 25%, 10%, 5%, 1%, 0.1% or less than 0.1% of the pepsin found in commercially-available pepsin-related products. In some cases, the amount of pepsin in a recombinant pepsinogen composition is less than 10%, 5%, 1%, 0.5%, 0.1% or 0.05% (weight pepsin/weight pepsinogen). The formulated composition may be substantially devoid of pepsin.

In some embodiments, at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, or 99% w/w of the protein in the composition is recombinant pepsinogen.

In some embodiments, the composition comprises a protein content of at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, or 90% w/w.

In some embodiments, the recombinant pepsinogen in a composition comprises an amino acid sequence of one of SEQ ID Nos. 1-9 or a sequence with at least 90% identity thereto.

A consumable composition can be an ingredient of a final product or finished product. For example, recombinant pepsinogen or recombinant pepsin can be mixed with water or other liquids to form a proteolytically inactive solution of recombinant pepsinogen or recombinant pepsin. In some cases, recombinant pepsinogen or recombinant pepsin can be mixed with water or other liquids to form a proteolytically active solution of recombinant pepsin. This solution can be an ingredient that is then mixed with other ingredients to make a final product for an end-user. A final or finished product is one that is ready for an end-user's use, such as for use in a food-making or industrial process, or for use as a digestive aid or treatment by an end-user for consumption by an animal, such as a human, companion animal or livestock. The finished product can be a processed product, such as processed food or a processed drink, or an industrial product, such as preparation of proteins, antibodies and peptides for use in medicine and in uses such as hide and leather preparation. In some instances, the pepsinogen or pepsin is provided in a separate container to be mixed into the final product or with other components to make a final product by the end-user.

In some embodiments, the recombinant pepsinogen compositions and recombinant pepsin compositions provided herein are formulated. Formulation can include ingredients suitable to create an orally consumable ingredient or orally administered pharmaceutical formulation. A formulated comprising recombinant pepsinogen or recombinant pepsin may comprise at least 2 g, 5 g, 7 g, 10 g, 15 g, 20 g of the enzyme per liter of the composition.

In some embodiments, a recombinant pepsinogen or recombinant pepsin compositions disclosed herein are formulated with at least one ingredient to form a digestive aid, such as in a pill, powder, tablet, capsule, caplets, liquid, syrup, gel or other suitable forms for human and animal oral ingestion. A recombinant pepsinogen composition or a recombinant pepsin composition may be formulated as a microencapsulate or liposomes suspended in syrups, liquids, sugar and pectin-based confectionary. Digestive aid recombinant pepsinogen or recombinant pepsin compositions can be ingested by an animal, including but not limited to human, companion animal or farm animal, to provide pepsin to aid the animal's digestion. For example, such digestive aid recombinant pepsin composition can be taken orally with the form of the enzyme in the composition as primarily or substantially the inactive pepsin form. Upon reaching an acidic environment in the animal's gut, the pepsin is converted into the active enzymatic form of pepsin and then the recombinant pepsin can aid in breaking down other proteins in the animal's gut to aid in the animal's digestion and improve nutrient absorption.

The at least one ingredient may be a food additive or pharmaceutically-acceptable excipient. These ingredients can add volume and/or mass to a composition. They may improve functional performance and/or physical characteristics. The ingredient may relate to pH adjustment; examples include, but are not limited to, Tris buffer, potassium phosphate, sodium hydroxide, potassium hydroxide, citric acid, sodium citrate, sodium bicarbonate, and hydrochloric acid. The ingredient may be a salt; examples include, but are not limited, to acid salts, alkali salts, organic salts, inorganic salts, phosphates, chloride salts, sodium salts, sodium chloride, potassium salts, potassium chloride, magnesium salts, magnesium chloride, magnesium perchlorate, calcium salts, calcium chloride, ammonium chloride, iron salts, iron chlorides, zinc salts, and zinc chloride. The ingredient may be a carbohydrate; examples include, but are not limited to, sugar, sucrose, glucose, fructose, galactose, lactose, maltose, mannose, allulose, tagatose, xylose, arabinose, high fructose corn syrup, high maltose corn syrup, corn syrup (e.g., glucose-free corn syrup), sialic acid, monosaccharides, disaccharides, and polysaccharides (e.g., polydextrose, maltodextrin). The ingredient may be a gum; examples include, but are not limited to, gum arabic, gellan gum, guar gum, locust bean gum, acacia gum, cellulose gum, and xanthan gum. The ingredient may be a liquid; examples include, but are not limited water, an aqueous buffer, an oil, a gel, and a carbohydrate-containing syrup or fluid.

In some embodiments, a digestive aid recombinant pepsin composition is mixed with an ingredient, such as lactose, to modify its enzymatic activity.

In some embodiments, the recombinant pepsinogen or recombinant pepsin compositions disclosed herein are used for preparation of food, beverage and other consumable compositions, such as for products that have soy or gelatin as ingredients. Recombinant pepsinogen or recombinant pepsin compositions disclosed herein can be used for making animal and vegetable protein hydrolysates for use in flavoring foods and beverages, and for making snack items and instant hot cereals. Exemplary uses include but are not limited to ale, beer, light beer, malt liquor, porter, stout, cheese (such as cheddar, cottage cheese, cream cheese, cream cheese spread), defatted soya flour, pre-cooked instant breakfast cereals, and hydrolyzed animal, milk and vegetable proteins. Recombinant pepsinogen or recombinant pepsin compositions also have utility in treating allergen-causing food items, such as legumes, to reduce allergic reactions when consumed by an animal, such as for human consumption.

In some embodiments, the recombinant pepsinogen or recombinant pepsin compositions disclosed herein are useful for preparation of biological tools and therapeutics. For example, the recombinant pepsinogen or recombinant pepsin compositions can be converted to composition containing active pepsin and employed to create antibody fragments, such as Fabs, that can be used for diagnostic and therapeutic applications, as well as used as tools in biotechnology.

A recombinant pepsinogen composition or a recombinant pepsin composition may also be formulated for the treatment of disease or condition of the gastrointestinal tract. Such a method may include steps of (a) providing the recombinant pepsinogen in a formulated composition, in which the pepsinogen is produced by the method according to any herein disclosed method and (b) administering the formulated composition for oral administration; in which upon contact of the formulated composition with an animal gut environment, the pepsinogen is converted to high-activity stable pepsin; and in which the pepsin is effective to treat the disease or condition of the gastrointestinal tract. Alternately, a recombinant pepsin composition, as disclosed herein, may be administered to a subject with a disease or condition of the gastrointestinal tract; here, the recombinant pepsin is in a primarily or substantially inactive form. The recombinant pepsin composition may then be activated in the subject's gastrointestinal tract and release the active form of the pepsin enzyme. A subject can be an animal, such as a human, a companion animal or livestock animal.

The recombinant pepsinogen or recombinant pepsin compositions disclosed herein can used to make animal-free products and ingredients, such as animal free pharmaceuticals, digestive aids, food and beverage ingredients, food and beverage products and enzyme preparations (such as animal-free rennet for use in cheese-making.

The recombinant pepsinogen or recombinant pepsin compositions disclosed herein can used for vegetarian, vegan, kosher and halal ingredients and products.

Additional Compositions and Methods

An aspect of the present disclosure is a method of producing a stable pepsin composition. The method comprises steps of (a) providing a microorganism that expresses a recombinant pepsinogen; (b) culturing the microorganism under conditions in which the recombinant pepsinogen polypeptide is expressed and secreted by the microorganism into a growth media; (c) harvesting the growth media and removing the microorganism therefrom to obtain a liquid starting material; (d) lowering the pH of the liquid starting material to less than pH 4.0 to obtain an activated pepsin composition; and (e) raising the pH of the activated pepsin composition to a pH of between about 5.4 and 7.0 to obtain a stable pepsin composition. The stable pepsin composition has a specific activity at pH of 2 of between about 100 FCC units/mg total protein and about 19,000 FCC units/mg total protein.

In some embodiments, the method further comprises, after step (d), a step of isolating activated pepsin polypeptide from other proteins and small molecules in the activated pepsin composition and/or, after step (e), a step of isolating activated pepsin polypeptide from other proteins and small molecules in the stable pepsin composition.

In some embodiments, the stable pepsin composition comprises an intact and stable proteolytically inactive form of recombinant pepsin.

In some embodiments, the specific activity at pH of 2 is at least 500 FCC units/mg total protein, at least 1000 FCC units/mg total protein, at least 2000 FCC units/mg total protein, at least 5000 FCC units/mg total protein, at least 10000 FCC units/mg total protein, or at least 15000 FCC units/mg total protein, and less than 20000 FCC units/mg total protein. As examples, the specific activity at pH of 2 is at least 100 FCC units/mg total protein, at least 200 FCC units/mg total protein, at least 300 FCC units/mg total protein, at least 400 FCC units/mg total protein, at least 500 FCC units/mg total protein, at least 600 FCC units/mg total protein, at least 700 FCC units/mg total protein, at least 800 FCC units/mg total protein, at least 900 FCC units/mg total protein, at least 1000 FCC units/mg total protein, at least 1100 FCC units/mg total protein, at least 1200 FCC units/mg total protein, at least 1300 FCC units/mg total protein, at least 1400 FCC units/mg total protein, at least 1500 FCC units/mg total protein, at least 1600 FCC units/mg total protein, at least 1700 FCC units/mg total protein, at least 1800 FCC units/mg total protein, at least 1900 FCC units/mg total protein, at least 2000 FCC units/mg total protein, at least 3000 FCC units/mg total protein, at least 4000 FCC units/mg total protein, at least 5000 FCC units/mg total protein, at least 6000 FCC units/mg total protein, at least 7000 FCC units/mg total protein, at least 8000 FCC units/mg total protein, at least 9000 FCC units/mg total protein, at least 10000 FCC units/mg total protein, at least 11000 FCC units/mg total protein, at least 12000 FCC units/mg total protein, at least 13000 FCC units/mg total protein, at least 14000 FCC units/mg total protein, at least 15000 FCC units/mg total protein, at least 16000 FCC units/mg total protein, at least 17000 FCC units/mg total protein, at least 18000 FCC units/mg total protein, or at least 19000 FCC units/mg total protein and less than 20000 FCC units/mg total protein. As used herein, an FCC unit (also referred to herein as a pepsin unit) is defined as that quantity of enzyme that produces the equivalent of 1 µmol of tyrosine per min under the conditions of incubating the enzyme with 2% hemoglobin substrate at pH 1.6 for 10 minutes at 25° C. (see Food Chemical Codex, 11th ed. (Pharmacopeial Convention. 2018) at 1386-87 "Pepsin Activity").

In some embodiments, the final pH of the stable pepsin composition is between about 5.4 and 6.0.

In some embodiments, the recombinant pepsinogen is present in at least about 1, 2, 3, 4, 5, 6, 7, 8, 9, 10, 11, 12, 13, 14, 15, 16, 17, 18, 19, 20 or greater than 20 g/liter in the growth medium prior to step (c).

In some embodiments, the growth medium is filtered after step (b), the liquid starting material is filtered after step (c), the activated pepsin composition is filtered after step (d), and/or the stable pepsin composition is filtered after step (e).

In some embodiments, a recombinant pepsin in the stable pepsin composition comprises an amino acid sequence of a pig, a sheep, a Central European red deer, a goat, a cow, a human, a yak, or a zebu pepsin.

Another aspect of the present disclosure is a method of producing a recombinant pepsinogen. The method comprises steps of (a) providing a microorganism that expresses a recombinant pepsinogen, wherein the expressed pepsinogen is secreted by the microorganism into a growth media; (b) culturing the microorganism until the secreted pepsinogen is present in the growth medium in an amount of at least about 1, 2, 3, 4, 5, 6, 7, 8, 9, 10, 11, 12, 13, 14, 15, 16, 17, 18, 19, 20 or greater than 20 g/liter; and (c) harvesting the growth media and removing the microorganism therefrom to obtain a liquid material in which the recombinant pepsinogen is substantially in a proteolytically inactive form. The recombinant pepsinogen that is substantially in the proteolytically inactive form is capable of being activated by reducing the pH or by exposure to an acidic environment to produce a stable pepsin composition, wherein the stable pepsin composition has a specific activity at pH of 2 of between about 100 FCC units/mg total protein and about 19,000 FCC units/mg total protein.

In some embodiments, the recombinant pepsinogen comprises an amino acid sequence of a pig, a sheep, a Central European red deer, a goat, a cow, a human, a yak, or a zebu pepsinogen.

In some embodiments, the recombinant pepsinogen comprises an amino acid sequence of one of SEQ ID Nos. 1-9 or a sequence with at least 90% identity thereto.

In some embodiments, the microorganism that expresses the recombinant pepsinogen comprises a first inducible promoter which regulates the expression of the recombinant pepsinogen. In some embodiments, the method further comprises a step of inducing the expression of the recombinant pepsinogen after or at least partially concurrent with the step of culturing the microorganism.

In some embodiments, the microorganism is selected from yeast, filamentous fungi, a *Saccharomyces* species, a bacteria, a *Pichia* species, a *Trichoderma* species and an *Aspergillus* species. In some embodiments, the microorganism is a *Pichia* species. In some embodiments, the microorganism further comprises a helper factor. In some embodiments, the helper factor is expressed from a second inducible promoter. In some embodiments, the first inducible promoter, the second inducible promoter, or both the first and second inducible promoters are induced by methanol.

In some embodiments, the method further comprises a desalting step after the harvesting step and/or a drying step after the harvesting step. In some embodiments, the drying step comprises spray drying or lyophilization.

In some embodiments, the specific activity at pH of 2 is at least 500 FCC units/mg total protein, at least 1000 FCC units/mg total protein, at least 2000 FCC units/mg total protein, at least 5000 FCC units/mg total protein, at least 10000 FCC units/mg total protein, or at least 15000 FCC units/mg total protein, and less than 20000 FCC units/mg total protein. As examples, the specific activity at pH of 2 is at least 100 FCC units/mg total protein, at least 200 FCC units/mg total protein, at least 300 FCC units/mg total protein, at least 400 FCC units/mg total protein, at least 500 FCC units/mg total protein, at least 600 FCC units/mg total protein, at least 700 FCC units/mg total protein, at least 800 FCC units/mg total protein, at least 900 FCC units/mg total protein, at least 1000 FCC units/mg total protein, at least 1100 FCC units/mg total protein, at least 1200 FCC units/mg total protein, at least 1300 FCC units/mg total protein, at least 1400 FCC units/mg total protein, at least 1500 FCC units/mg total protein, at least 1600 FCC units/mg total protein, at least 1700 FCC units/mg total protein, at least 1800 FCC units/mg total protein, at least 1900 FCC units/mg total protein, at least 2000 FCC units/mg total protein, at least 3000 FCC units/mg total protein, at least 4000 FCC units/mg total protein, at least 5000 FCC units/mg total protein, at least 6000 FCC units/mg total protein, at least 7000 FCC units/mg total protein, at least 8000 FCC units/mg total protein, at least 9000 FCC units/mg total protein, at least 10000 FCC units/mg total protein, at least 11000 FCC units/mg total protein, at least 12000 FCC units/mg total protein, at least 13000 FCC units/mg total protein, at least 14000 FCC units/mg total protein, at least 15000 FCC units/mg total protein, at least 16000 FCC units/mg total protein, at least 17000 FCC units/mg total protein, at least 18000 FCC units/mg total protein, or at least 19000 FCC units/mg total protein and less than 20000 FCC units/mg total protein. As used herein, an FCC unit (also referred to herein as a pepsin unit) is defined as that quantity of enzyme that produces the equivalent of 1 µmol of tyrosine per min under the conditions of incubating the enzyme with 2% hemoglobin substrate at pH 1.6 for 10 minutes at 25° C. (see Food Chemical Codex, 11th ed. (Pharmacopeial Convention. 2018) at 1386-87 "Pepsin Activity").

In some embodiments, the stable pepsin composition comprises a recombinant pepsin having an amino acid sequence of SEQ ID NO. 10 or a sequence with at least 90% identity thereto.

In some embodiments, the method further comprising formulating the recombinant pepsin or recombinant pepsinogen with at least one ingredient to create, respectively, a formulated recombinant pepsin composition or recombinant pepsinogen composition in liquid, powder, pill, tablet, or capsule form. In some embodiments, the liquid is a syrup or a gel Yet another aspect of the present disclosure is composition comprising a recombinant pepsin polypeptide. The composition is (a) free from animal-derived proteins, (b) the pepsin polypeptide is substantially in an intact and stable proteolytically inactive form, (c) the composition has a pH greater than about 5.4, and (d) the composition has a specific activity of between about 100 FCC units/mg total protein and about 19,000 FCC units/mg total protein.

In some embodiments, the specific activity at pH of 2 is at least 500 FCC units/mg total protein, at least 1000 FCC units/mg total protein, at least 2000 FCC units/mg total protein, at least 5000 FCC units/mg total protein, at least 10000 FCC units/mg total protein, or at least 15000 FCC units/mg total protein, and less than 20000 FCC units/mg total protein. In some embodiments, the specific activity at pH of 2 is at least 500 FCC units/mg total protein, at least 1000 FCC units/mg total protein, at least 2000 FCC units/mg total protein, at least 5000 FCC units/mg total protein, at least 10000 FCC units/mg total protein, or at least 15000 FCC units/mg total protein, and less than 20000 FCC units/mg total protein. As examples, the specific activity at pH of 2 is at least 100 FCC units/mg total protein, at least 200 FCC units/mg total protein, at least 300 FCC units/mg total protein, at least 400 FCC units/mg total protein, at least 500 FCC units/mg total protein, at least 600 FCC units/mg total protein, at least 700 FCC units/mg total protein, at least 800 FCC units/mg total protein, at least 900 FCC units/mg total protein, at least 1000 FCC units/mg total protein, at least 1100 FCC units/mg total protein, at least 1200 FCC units/mg total protein, at least 1300 FCC units/mg total protein, at least 1400 FCC units/mg total protein, at least 1500 FCC units/mg total protein, at least 1600 FCC units/mg total protein, at least 1700 FCC units/mg total protein, at least 1800 FCC units/mg total protein, at least 1900 FCC units/mg total protein, at least 2000 FCC units/mg total protein, at least 3000 FCC units/mg total protein, at least 4000 FCC units/mg total protein, at least 5000 FCC units/mg total protein, at least 6000 FCC units/mg total protein, at least 7000 FCC units/mg total protein, at least 8000 FCC units/mg total protein, at least 9000 FCC units/mg total protein, at least 10000 FCC units/mg total protein, at least 11000 FCC units/mg total protein, at least 12000 FCC units/mg total protein, at least 13000 FCC units/mg total protein, at least 14000 FCC units/mg total protein, at least 15000 FCC units/mg total protein, at least 16000 FCC units/mg total protein, at least 17000 FCC units/mg total protein, at least 18000 FCC units/mg total protein, or at least 19000 FCC units/mg total protein and less than 20000 FCC units/mg total protein. As used herein, an FCC unit (also referred to herein as a pepsin unit) is defined as that quantity of enzyme that produces the equivalent of 1 µmol of tyrosine per min under the conditions of incubating the enzyme with 2% hemoglobin substrate at pH 1.6 for 10 minutes at 25° C. (see Food Chemical Codex, 11th ed. (Pharmacopeial Convention. 2018) at 1386-87 "Pepsin Activity").

In some embodiments, the composition has a pH between about 5.4 to about 6.0.

In some embodiments, the composition comprises a protein content of at least 1%, 2%, 3%, 4%, 5%, 6%, 7%, 8%, 9%, 10, 1%, 12%, 13%, 14%, 15%, 20%, 25%, 30%, 35%, 40%, 45%, 50%, 55%, 60%, 65%, 70%, 75%, 80%, 85%, or 90% w/w.

In some embodiments, the composition is in powdered form.

In some embodiments, the composition is in liquid form.

In some embodiments, the recombinant pepsin polypeptide is at least 10 mg per liter, at least 100 mg per liter, at least 500 mg per liter, at least 1 g per liter, at least 2 g per liter, at least 5 g per liter, at least 7 g per liter, at least 10 g per liter, at least 15 g per liter, or at least 20 g per liter. As examples, the recombinant pepsin polypeptide is at least 10 mg per liter, at least 20 mg per liter, at least 30 mg per liter, at least 40 mg per liter, at least 50 mg per liter, at least 60 mg per liter, at least 70 mg per liter, at least 80 mg per liter, at least 90 mg per liter, at least 100 mg per liter, at least 200 mg per liter, at least 300 mg per liter, at least 400 mg per liter, at least 500 mg per liter, at least 600 mg per liter, at least 700 mg per liter, at least 800 mg per liter, at least 900 mg per liter, at least 1000 mg per liter, at least 1100 mg per liter, at least 1200 mg per liter, at least 1300 mg per liter, at least 1400 mg per liter, at least 1500 mg per liter, at least 1600 mg per liter, at least 1700 mg per liter, at least 1800 mg per liter, or at least 1900 mg per liter.

In some embodiments, the recombinant pepsin polypeptide comprises an amino acid sequence of a pig, a sheep, a Central European red deer, a goat, a cow, a human, a yak, or a zebu pepsin.

In some embodiments, the recombinant pepsin polypeptide comprises SEQ ID NO: 10, or an amino acid sequence with at least 90% identity thereto.

In some embodiments, the recombinant pepsin polypeptide is produced in a yeast, a filamentous fungi, a *Saccharomyces* species, a bacteria, a *Pichia* species, a *Trichoderma* species, or an *Aspergillus* species. In some embodiments, the recombinant pepsin polypeptide is produced in a *Pichia* sp.

In some embodiments, the liquid form is a syrup or a gel.

In some embodiments, at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, or 99% w/w of the protein in the composition is recombinant pepsin.

ADDITIONAL EMBODIMENTS

Embodiment 1: A composition comprising a recombinant pepsinogen polypeptide, wherein the pepsinogen is substantially in a stable proteolytically inactive form.

Embodiment 2: The composition of embodiment 1, wherein the pepsinogen polypeptide is present in at least 5 g per liter in the composition.

Embodiment 3: The composition of embodiment 1 or embodiment 2, wherein the pepsinogen polypeptide when converted to a proteolytically active form has a higher specific activity as compared to native bovine pepsin isolated from bovine stomach or native porcine pepsin isolated from porcine stomach in the same quantity.

Embodiment 4: The composition of embodiment 3, wherein the specific activity of the proteolytically active form is at least 2 times, 2.5 times or 3 times greater than the native bovine pepsin or native porcine pepsin.

Embodiment 5: The composition of embodiment 1 or embodiment 2, wherein the pepsinogen polypeptide is converted to a proteolytically active form and the proteolytically active form has a specific activity of at least 50000 or 60000 or 70000 FCC units/mg protein.

Embodiment 6: The composition according to any of embodiments 1 to 5, wherein the recombinant pepsinogen polypeptide is produced in a yeast or filamentous fungi, a *Saccharomyces* species, a bacteria, a *Pichia* species, a *Trichoderma* species or an *Aspergillus* species.

Embodiment 7: The composition of embodiment 6, wherein the recombinant pepsinogen polypeptide is produced in a *Pichia* species.

Embodiment 8: The composition of embodiment 1, wherein the pepsinogen exhibits stability in the inactive form for at least 6 months.

Embodiment 9: The composition according to any of embodiments 1 to 8, wherein the composition is in powder form.

Embodiment 10: The composition according to any of embodiments 1 to 9, wherein the recombinant pepsinogen polypeptide is a porcine, bovine, ovine, equine or human pepsinogen.

Embodiment 11: The composition according to any of embodiments 1 to 9, wherein the recombinant pepsinogen polypeptide comprises an amino acid sequence of any one of SEQ ID NOs: 1-9, or an amino acid sequence having at least 80% homology with any one of SEQ ID NOs: 1-9.

Embodiment 12: A method of obtaining high quantities of recombinant pepsinogen in an inactive form comprising: providing a host cell comprising a nucleic acid encoding a pepsinogen polypeptide, wherein the nucleic acid further includes a segment directing secretion of the pepsinogen polypeptide from the cell; growing the host cell in a liquid medium, such that the pepsinogen polypeptide is expressed and secreted from the host cell under conditions whereby the pepsinogen polypeptide is substantially in a proteolytically inactive form; isolating liquid medium containing the secreted pepsinogen polypeptide.

Embodiment 13: The method of embodiment 12, wherein the host cell further comprises an inducible promoter driving the expression of the nucleic acid encoding the pepsinogen polypeptide.

Embodiment 14: The method of embodiment 2, wherein the method further comprises a step of inducing the expression of the pepsinogen subsequent to or at least partially concurrent with the growing step.

Embodiment 15: The method of embodiment 13 or embodiment 14, wherein the promoter driving the pepsinogen expression is induced by methanol.

Embodiment 16: The method according to any of embodiments 12-15, further comprising treating the isolated liquid media to adjust the pH to about 2-4 followed by an adjustment of the pH to 5.5-7.0, e.g., pH 6.

Embodiment 17: The method of embodiment 16, wherein the isolated liquid media is filtered at one or more points selected from the group consisting of (i) prior to adjusting the pH to 3.5, (ii) after adjusting the pH to 6.0, (iii) after a desalting step; (iv) prior to lyophilization and (v) a combination of any of (i)-(iv).

Embodiment 18: The method of embodiment 12, wherein the pepsin polypeptide is present in at least about 1, 2, 3, 4, 5, 6, 7, 8, 9, 10, 11, 12, 13, 14, 15, 16, 17, 18, 19, 20 or greater than 20 g/liter in the liquid media.

Embodiment 19: The method according to any of embodiments 12-18, wherein the method further comprises the activation to an enzymatically active or mature form of the enzyme.

Embodiment 20: The method according to embodiment 19, wherein the pepsinogen polypeptide when converted to an enzymatically active form has a higher specific activity as compared to native bovine pepsin isolated from bovine stomach or native porcine pepsin isolated from porcine stomach in the same quantity.

Embodiment 21: The method of embodiment 19, wherein the specific activity of the enzymatically active form is at least 2 times, 2.5 times or 3 times greater than the native bovine pepsin or native porcine pepsin.

Embodiment 22: The method according to any of embodiments 12-20, wherein the pepsinogen polypeptide is converted to an enzymatically active form and the enzymatically active form has a specific activity of at least 50000 or 60000 or 70000 FCC units/mg protein.

Embodiment 23: The method according to any of embodiments 12-21, wherein the host cell is a yeast or filamentous fungi, a *Saccharomyces* species, a bacteria, a *Pichia* species, a *Trichoderma* species or an *aspergillus* species.

Embodiment 24: The method of embodiment 22, wherein the host cell is a *Pichia* species.

Embodiment 25: The method according to any of embodiments 12-23, wherein the pepsinogen polypeptide exhibits stability in the inactive or immature form for at least 6 months.

Embodiment 26: The method according to any of embodiments 12-24, wherein the composition is in powder form.

Embodiment 27: The method according to any of embodiments 12-25, wherein the recombinant pepsinogen polypeptide is a porcine, bovine, ovine, equine or human pepsinogen.

Embodiment 28: The method according to any of embodiments 12-25, wherein the recombinant pepsinogen polypeptide comprises an amino acid sequence of any one of SEQ ID NOs: 1-9, or an amino acid sequence having at least 80% homology with any one of SEQ ID NOs: 1-9.

Embodiment 29: A formulated composition comprising a recombinant pepsinogen and at least one formulated ingredient, wherein the formulated composition is in a form selected from the group consisting of a liquid (e.g., syrup and gel), powder, a pill, a tablet and a capsule, a microencapsulate, a liposome suspended in syrup and wherein the pepsinogen is substantially enzymatically inactive.

Embodiment 30: The composition of embodiment 28, wherein the formulated composition is substantially devoid of pepsin.

Embodiment 31: The composition of embodiment 29, wherein the amount of pepsin is less than 10%, 5%, 1%, 0.5%, 0.1% or 0.05% (weight pepsin/weight pepsinogen).

Embodiment 32: The composition of embodiment 28, wherein the pepsinogen is capable of activation when exposed to a pH less than about 6.

Embodiment 33: The formulated composition of embodiment 31, wherein the pH of the composition is greater than about 6.

Embodiment 34: The formulated composition of embodiment 31, wherein the pepsinogen is capable of activation when exposed to an animal gut environment.

Embodiment 35: The formulated composition of embodiment 28, wherein the recombinant pepsinogen is a bovine, porcine, ovine or human enzyme.

Embodiment 36: A method of preparing a formulated pepsinogen composition comprising: providing a recombinant pepsinogen, wherein the pepsinogen is substantially enzymatically inactive; formulating the recombinant pepsinogen with at least one ingredient to create a formulated pepsinogen composition in liquid (e.g., syrup and gel), powder, pill, tablet or capsule form: wherein the formulated pepsinogen composition is capable of activation when exposed to a pH of less than about 6.

Embodiment 37: The method of embodiment 35, wherein the recombinant pepsinogen is a bovine, porcine, ovine or human enzyme.

Embodiment 38: The method of embodiment 35, wherein the recombinant pepsinogen is produced in a heterologous host cell selected from the group consisting of bacteria, yeast, and filamentous fungi.

Embodiment 39: The method of embodiment 35, wherein the host cell is a *Pichia* species, a *Saccharomyces* species, a bacteria, an *Aspergillus* or a *Trichoderma* species.

Embodiment 40: The method of embodiment 36-39, wherein the recombinant pepsinogen is secreted from the host cell.

Embodiment 41: The method of embodiment 40, wherein the recombinant pepsinogen secreted is in a substantially enzymatically inactive form.

Embodiment 42: A composition comprising recombinant stable pepsin, wherein the stable pepsin is substantially enzymatically inactive.

Embodiment 43: The composition of embodiment 42, wherein recombinant stable pepsin is capable of activation when exposed to a pH less than about 6.

Embodiment 44: The composition of embodiment 42, wherein the pH of the composition is greater than about 6.

Embodiment 45: The composition of embodiment 42, wherein the recombinant stable pepsin is capable of activation when exposed to an animal gut environment.

Embodiment 46: The composition of embodiment 42, wherein the recombinant stable pepsin is a bovine, porcine, ovine or human enzyme.

Embodiment 47: The composition according to any of embodiments 42-46, wherein the specific activity of the recombinant stable pepsin when activated to a proteolytically active form is at least 2 times, 2.5 times or 3 times greater than the native bovine pepsin or native porcine pepsin.

Embodiment 48: The composition according to any of embodiments 42-46, wherein the recombinant stable pepsin when converted to a proteolytically active form has a specific activity of at least 50000 or 60000 or 70000 FCC units/mg protein.

Embodiment 49: The composition according to any of embodiments 42-48, wherein the recombinant stable pepsin is first produced as a pepsinogen polypeptide in a yeast or filamentous fungi, a *Saccharomyces* species, a bacteria, a *Pichia* species, a *Trichoderma* species or an *Aspergillus* species and then converted to pepsin.

Embodiment 50: A method of treating a disease or condition of the gastrointestinal tract comprising: providing a recombinant pepsinogen in a formulated composition, wherein the pepsinogen is substantially enzymatically inactive in the formulated composition; administering the formulated composition for oral administration; wherein upon contact of the formulated composition with an animal gut environment, the pepsinogen is converted to an enzymatically active form; and wherein the enzymatically active form is effective to treat the disease or condition of the gastrointestinal tract.

Embodiment 51: The composition of any of embodiments 1-11, wherein the composition comprises at least one production specification set forth in Table 2.

Embodiment 52: The composition of any of embodiments 1-11 or embodiment 51, wherein the composition comprises at least one quality specification set forth in Table 3.

Definitions

The terminology used herein is for the purpose of describing particular cases only and is not intended to be limiting.

As used herein, unless otherwise indicated, the terms "a", "an" and "the" are intended to include the plural forms as well as the single forms, unless the context clearly indicates otherwise.

The terms "comprise", "comprising", "contain," "containing," "including", "includes", "having", "has", "with", or variants thereof as used in either the present disclosure and/or in the claims, are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean 10% greater than or less than the stated value. In another example, "about" can mean within 1 or more than 1 standard deviation, per the practice in the given value. Where particular values are described in the application and claims, unless otherwise stated the term "about" should be assumed to mean an acceptable error range for the particular value.

The term "substantially" is meant to be a significant extent, for the most part; or essentially. In other words, the term substantially may mean nearly exact to the desired attribute or slightly different from the exact attribute. Substantially may be indistinguishable from the desired attribute. Substantially may be distinguishable from the desired attribute but the difference is unimportant or negligible.

Any aspect or embodiment described herein can be combined with any other aspect or embodiment as disclosed herein.

Examples

The following examples are given for the purpose of illustrating various embodiments of the invention and are not meant to limit the present invention in any fashion. The present examples, along with the methods described herein are presently representative of various embodiments, are exemplary, and are not intended as limitations on the scope of the invention. Changes therein and other uses which are encompassed within the spirit of the invention as defined by the scope of the claims will occur to those skilled in the art.

Example 1: Expression of Pepsinogen

The coding sequence of porcine pepsinogen (SEQ ID NO: 2) was fused to the *Saccharomyces* alpha factor pre-pro secretion signal under the control of a methanol-induced promoter. The fusion was constructed such that the pro form, pepsinogen, lacking the native secretion signal was produced upon expression and secretion of the pepsinogen.

The *P. pastoris* strain BG08 (BioGrammatics Inc., Carlsbad; CA, USA) is a single colony isolate from the Phillips Petroleum strain NRRL Y-11430 obtained from the Agriculture Research Service culture collection (Sturmberger, et al. 2016). *P. pastoris* BG10 (BioGrammatics Inc, Carlsbad, Calif., USA) was derived from BG08 using Hoechst dye selection to remove cytoplasmic killer plasmids (Sturmberger, et al. 2016). This BG10 strain was then further modified to have a deletion in the Alcohol Oxidase 1 gene (AOX1). This deletion generates a methanol-utilization slow (mutS) phenotype that reduces the strain's ability to consume methanol, e.g., as a carbon source. This base strain was called DFB-001 and used for the transformation of the pepsinogen construct.

The pepsinogen construct, along with a construct for the expression of the *P. pastoris* transcription factor HAC1 under the control of a strong methanol inducible promoter, was transformed into *Pichia pastoris* and isolates were selected that expressed and secreted pepsinogen. A transformant was selected as a high-producer for use in subsequent steps. Propagation of the strain confirmed that all changes introduced into the strain were stably integrated in the genome and confirmed to be present after >45 generations of growth on non-selective growth media.

Sequencing confirmed that this strain does not contain any antibiotic markers or prokaryotic vector origin of replication sequences.

The resulting strain was grown in fermentation conditions in high-density growth conditions at about pH 5. After about 36 hours of growth under fermentation conditions, the pH was raised to about pH 6, and expression of pepsinogen was induced by the addition of methanol to the culture. The pepsinogen was isolated from the growth media of the culture.

In some cases, the liquid media was centrifuged to remove *P. pastoris* cells. This was followed by filtration of the supernatant using a 0.2 um hollow fiber membrane filtration to remove host protein and cell debris.

Example 2: Conversion of Pepsinogen to Pepsin

The pepsinogen solution was concentrated to a 5× to 10× concentrate using 10 kDa hollow fiber membrane filtration. An acid solution of 85% phosphoric acid was added to the resulting liquid composition from Example 1 to lower the pH to 3.5, and the mixture was agitated for 2.25 hours at room temperature (about 20-25° C.). Following this agitation step, the pH was raised to 6 by addition of 5 N NaOH. The resulting concentrate was desalted with 10 DV of distilled water at pH 6 using 10 kDa hollow fiber membrane filtration. Then the solution was lyophilized to produce a pepsin powder.

Example 3: Characterization of Pepsinogen Activation

The pepsinogen composition (from Example 1 or 2) was characterized for its activation post dilution, e.g., conversion to active pepsin, under various temperature and pH ranges. In FIG. 1, the pepsinogen composition at pH 5.95 (B lane) was shifted to pH 3.5 by the addition of 2.5 N HCl and incubated for the times shown at room temperature (about 20°-25° C.), 35° C. or 45° C.; samples were raised to pH 6 using 2 NaOH. Samples were analyzed using polyacrylamide gel electrophoresis (PAGE) and conversion of pepsinogen to pepsin was observed as a change in the apparent molecular of the protein.

Figure 2:
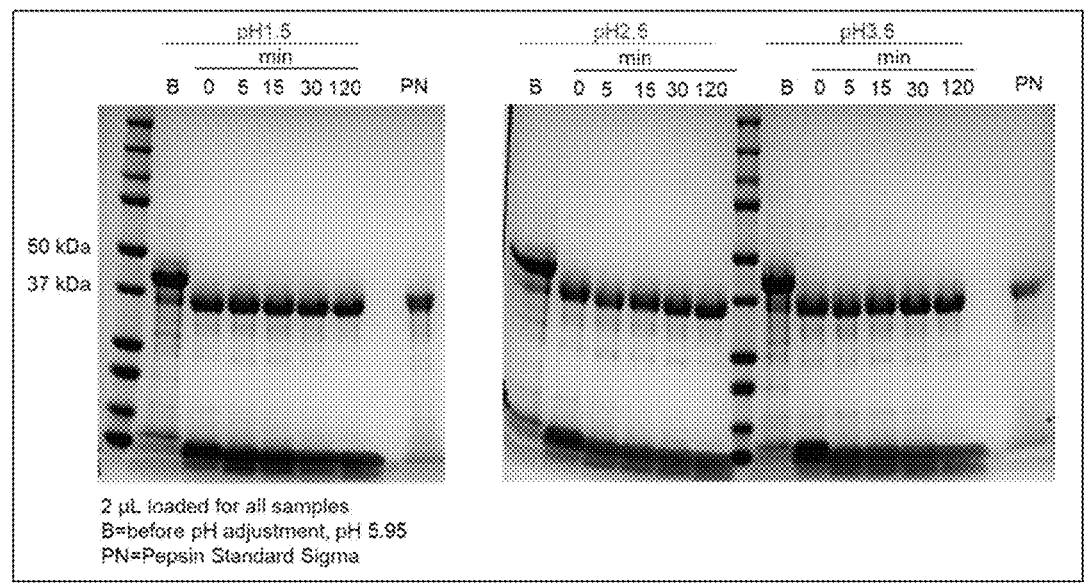
FIG. 2 shows pepsinogen composition at pH 5.95 (lane B) compared to activated pepsin at various pH after incubation with HCl for 5 minutes, 15 minutes, 30 minutes, and 120 minutes.
Figure 3:
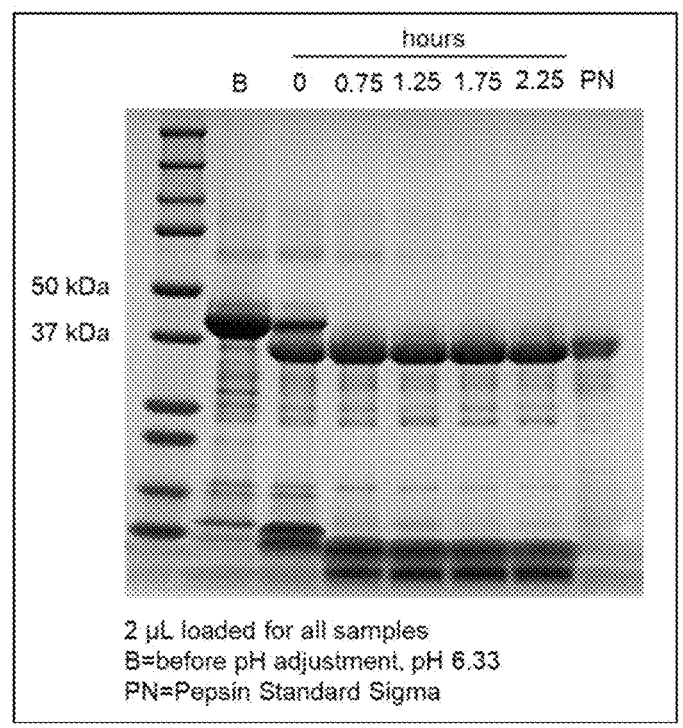
FIG. 3 shows pepsin activation for various times before conversion to inactive pepsin at pH 6.33 at 37° C.

FIG. 2, shows that the pepsinogen composition at pH 5.95 (B lane) was shifted to pH 1.5, 2.5, or 3.5 by the addition of 2.5 N HCl and incubated at 37° C. for the times shown followed by pH raising to pH 6.0 with 2 NaOH. Samples were analyzed using PAGE and conversion of pepsinogen to pepsin observed as a change in the apparent molecular weight of the protein. FIG. 3 shows images of protein gels of a pepsinogen composition for the times shown (in hours) at pH 1.5, 2.5, 3.5, and at room temperature; samples were raised to pH 6 using 2 NaOH. Samples were analyzed using PAGE and conversion of pepsinogen to pepsin was observed as a change in the apparent molecular of the protein.

Figure 4:
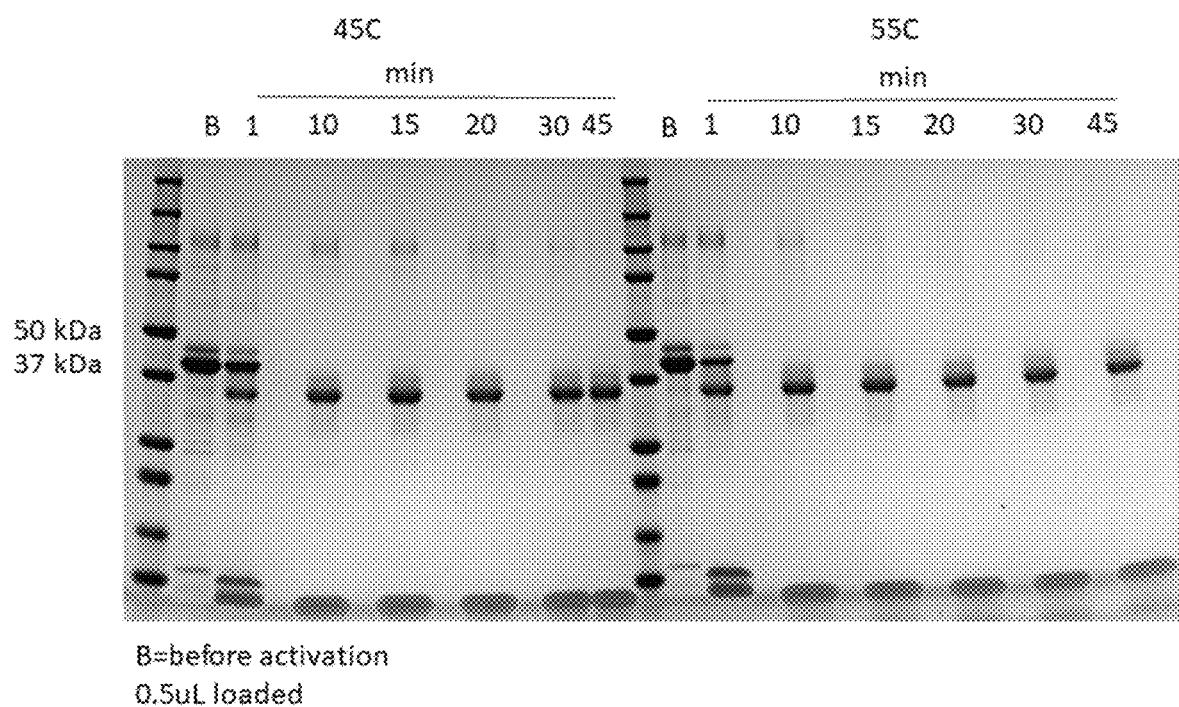
FIG. 4 shows pepsinogen composition activated at temperatures of 45° C. and 55° C. for various times.

FIG. 4, shows the pepsinogen composition activated at temperatures of 45° C. and 55° C. for the times shown, and raised to pH 6 using 2 NaOH. Samples were analyzed using PAGE and conversion of pepsinogen to pepsin was observed as a change in the apparent molecular of the protein.

Example 4: Characterization of Recombinant Pepsin

Lyophilized pepsin powder (Example 2) was subjected to a protein determination using combustion analysis (N×6.25) and activity was measured in an FCC9 enzyme assay (USP, Pepsin activity. In: *Ninth Edition of the Food Chemicals Codex (FCC 9)*. United States Pharmacopeia Convention, Rockville, Md., 2015e, pp. 1410-1411; see also *Food Chemical Codex, 11th ed.* (Pharmacopeial Convention. 2018) at 1386-87 "Pepsin Activity"). As compared to a commercially-available porcine pepsin product, the recombinant pepsin composition had over 3-times the specific activity.

Table 1 shows the results of the analysis for protein, fat, moisture, ash, carbohydrates and FCC units for the commercially-available native porcine pepsin and for a composition comprising recombinant pepsin. FCC units/mg is defined as follows: One pepsin unit is defined as that quantity of enzyme that produces the equivalent of 1 µmol of tyrosine per min under the conditions of incubating the enzyme with a 2% hemoglobin substrate at pH 1.6 for 10 minutes at 25° C. performed as set forth in *Food Chemical Codex, 11th ed.* (Pharmacopeial Convention. 2018) at 1386-87 "Pepsin Activity" (the same assay is also provided in *Ninth Edition of the Food Chemicals Codex (FCC 9)*. United States Pharmacopeia Convention, Rockville, Md., 2015e, pp. 1410-1411).

TABLE 1

FCC unit comparison between a commercially-available pepsin and a recombinant pepsin composition.

| | Commercial Porcine Pepsin | Recombinant Pepsin Composition |
|---|---|---|
| Protein % w/w (N X 6.25) | 50.25 | 31.3 |
| Fat % w/w | 0.535 | 0.285 |
| Moisture % w/w | 4.4 | 7.3 |
| Ash % w/w | 1.7 | 4.95 |
| Carbs (by difference) % w/w | 43.11 | 56.15 |
| Activity FCC units/mg protein | 27,343 | 70,863 |

Surprisingly, while the percentage of protein in the recombinant pepsin composition is significantly lower than the commercially-available native porcine pepsin, the FCC units of the recombinant pepsinogen composition is significantly (about 3×) higher. Without wishing to be bound by theory, the methods for manufacturing the pepsin compositions of the present disclosure provide a highly active product.

Example 5: Comparison of Pepsin Activity Profiles

Figure 5A:
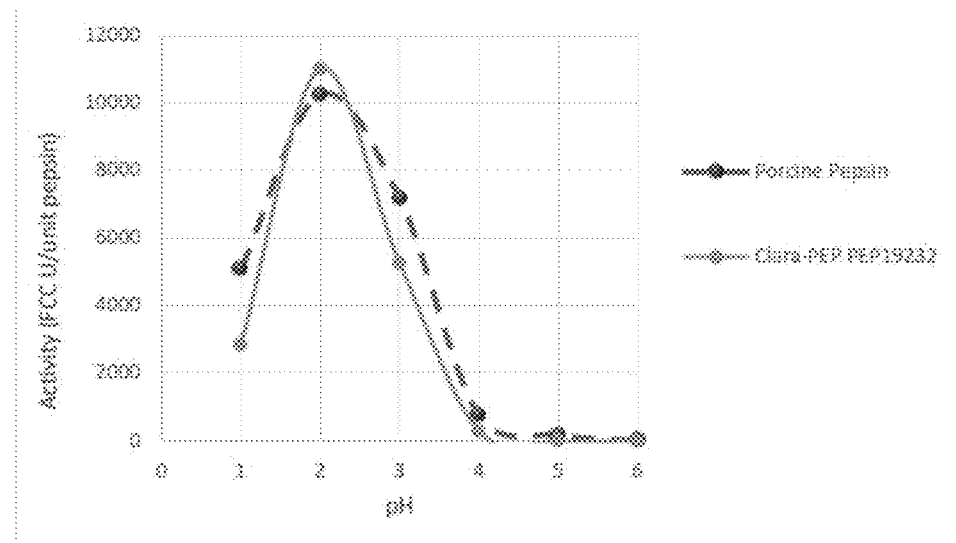
FIG. 5A shows a graph comparing the pH profile of a recombinant pepsin composition and a commercially-available native porcine pepsin. In this experiment, activity is expressed on the graph as FCC units/unit pepsin, where each pepsin unit is defined as the amount of pepsin present in the sample, derived from its peak area determined by HPLC.
Figure 5B:
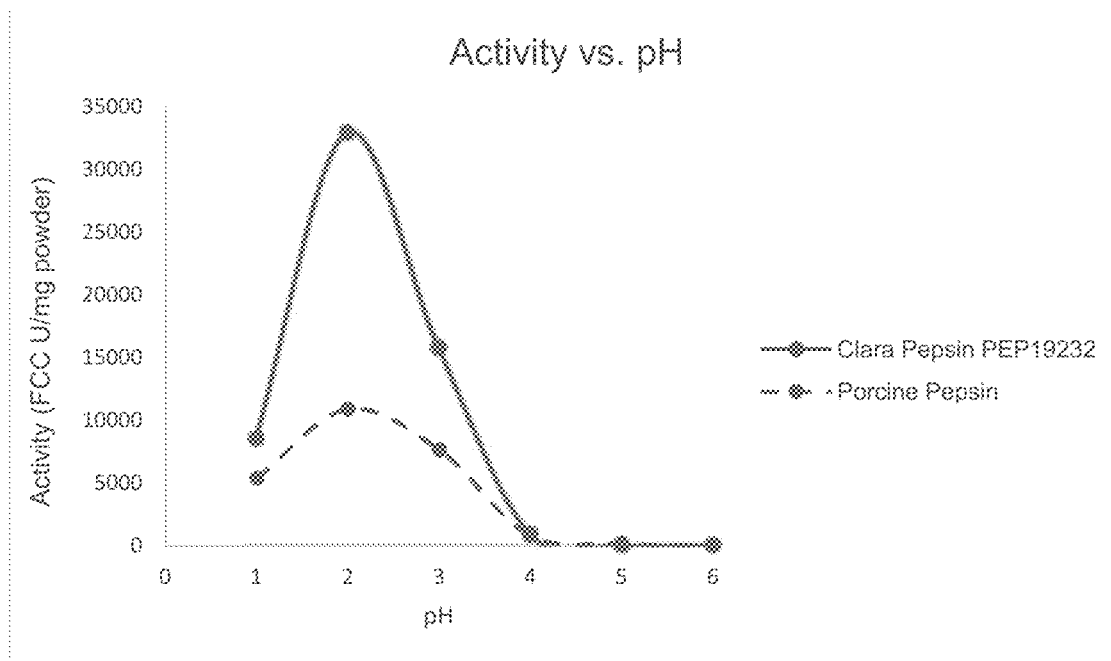
FIG. 5B shows a graph comparing the activity over a pH range of the recombinant pepsin composition and the commercially-available native porcine pepsin presented as the activity per mg powder composition.

A recombinant pepsin composition was tested for activity against a range of pH and compared against the activity of native porcine pepsin (see Example 4) using the FCC (9th Edition) Pepsin assay (Pharmacopeial Convention. 2014). The optimum activity was at pH 2 for both native porcine pepsin and the recombinant pepsin polypeptide of the present disclosure. Both pepsin enzymes tested had a similar activity profile (FIG. 5A and FIG. 5B). The pepsin activity in FIG. 5A is presented as FCC units/units pepsin, wherein each Pepsin unit is defined as the amount of pepsin present in the sample, derived from its peak area determined through HPLC. The pepsin activity in FIG. 5B is presented as FCC units/mg powder.

In some cases, pepsin assays were performed with the following changes ("alternate pepsin assay") to the assay described in Example 4: The activity assay was performed at 37° C. in a 96-well plate format and tyrosine was measured directly. These changes result in an output number that when multiplied by two (2) is equivalent to the FCC units of activity performed as in Example 4. The numbers reported for all alternate pepsin assays herein apply this conversion factor.

Example 6: Comparison of Immunoreactivity and Molecular Weights

Figure 6:
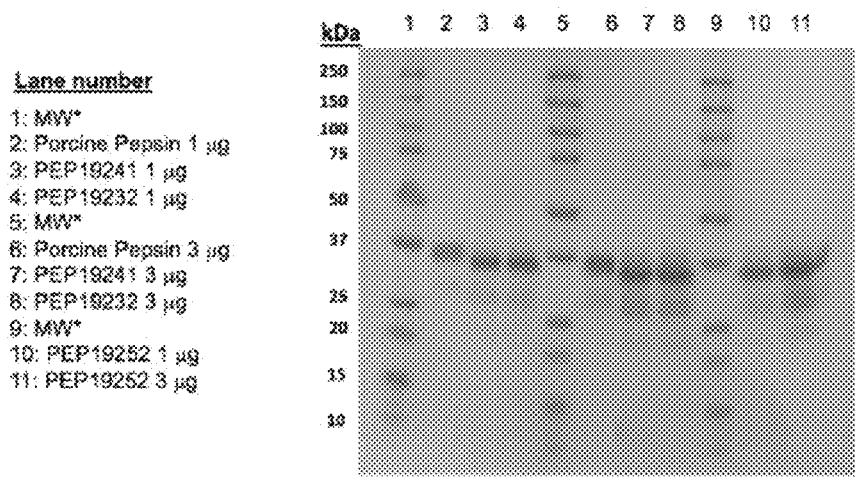
FIG. 6 shows a western blot comparing sizes of a recombinant pepsin composition and a commercially-available native porcine pepsin.

A recombinant pepsin composition and native porcine pepsin (see Example 4) were compared for immunoreactivity and molecular weight using western blotting technique (Tobin). Briefly, three separately-generated lots of the recombinant pepsin composition (PEP19232, PEP19241, PEP19252) and native porcine pepsin were run on SDS-PAGE and then transferred to nitrocellulose membrane. Western Blot was performed on the samples using primary pepsin antibody from rabbit (Abcam (ab182945)) at a 1:5000 dilution (Jensen 2012). The secondary antibody used was Goat anti-rabbit IgG conjugated to alkaline phosphatase (1:5000 dilution). FIG. 6 shows the western blot comparing the proteins.

Example 7: Pepsin Specifications

Based upon the characterization of the recombinant pepsin compositions and the properties of commercially-available native porcine pepsin, product specifications (Table 2) and quality control specifications (Table 3) were constructed.

TABLE 2

Product specifications for a recombinant pepsin composition

| Physical properties | Specification | |
|---|---|---|
| Source | Yeast fermentation-derived | |
| Appearance | White to off-white amorphous powder | |
| Solubility | Mostly soluble in water with slight opalescence. Practically insoluble in alcohol, chloroform and ether. | |
| Enzyme Activity | Specification | Method |
| Activity in Units/mg powder | 1:30000 FCC Units | FCC Assay[1] |
| Chemical Properties (in powder as is) | Specification | Method |
| Moisture | Maximum 10.0% | AOAC 925.09[2] |
| Ash | Maximum 5.0% | AOAC 942.05[3] |
| Hg | <1 ppm | ICP-AES[4] |
| Pb | <1 ppm | ICP-AES[4] |
| As | <1 ppm | ICP-AES[4] |
| Cd | <1 ppm | ICP-AES[4] |
| Microbial Properties (in powder as is) | Specification | Method |
| Standard Plate Count | <10000 CFU/g | AOAC 990.12[5] |
| Yeast & Mold | <100 CFU/g | AOAC 997.02[6] |
| *Salmonella* | Not Detected/25g | AOAC 2003.09[7] |
| *E. coli* | <10 CFU/g | AOAC 991.14[8] |
| Total coliform | ≤30 CFU/g | AOAC 991.14[8] |

[1]Food Chemical Codex, 9th ed. (Pharmacopeial Convention. 2014)
[2]Association of Official Analytical Chemists (1995). In Official Methods of Analysis.
[3]J AOAC Int. 2012 Sep-Oct;95(5): 1392-7.
[4]J. AOAC vol. 90 (2007) 844-856.
[5]AOAC International (2005). Aerobic plate count in foods, dry rehydratable film, method 990.12. AOAC International, 17th ed. Gaithersburg, MD.
[6]17.2.09 AOAC Official. Method 997.02. Yeast and Mold Counts in Foods Dry Rehydratable Film Method (Petrifilm ™ Method) First Action 1997 Final Action 2000
[7]AOAC International. 2005. *Salmonella* in selected foods, BAX automated system, method 2003.09. In Official methods of analysis of AOAC International, 17th ed. AOAC International Gaithersburg, MD.
[8]AOAC International, 2005. *E. coli* count in foods, dry rehydratable film, method 991.14. In Official methods of analysis of AOAC International, 17th ed. AOAC International Gaithersburg, MD.

TABLE 3

Quality specifications for recombinant pepsin compositions

| Parameter | Specification * | PEP19232 | PEP19241 | PEP19252 |
|---|---|---|---|---|
| Activity (FCC Units/mg powder) | 1:30000 | 1:31440 | 1:31000 | 1:32200 |
| Moisture | <10% | 9.4 | 9.1 | 9.6 |
| Ash % | <5% | 3.54 | 3.79 | 3.61 |
| Hg | <1 mg/kg | <0.01 | <0.01 | <0.01 |
| Pb | <1 mg/kg | <0.01 | <0.01 | <0.01 |
| As | <1 mg/kg | <0.01 | <0.01 | <0.01 |
| Cd | <1 mg/kg | <0.01 | <0.01 | <0.01 |
| Aerobic plate count | <10000 CFU/g | <10 | <10 | <10 |
| Yeast & Mold | <100 CFU/g | <10 | <10 | <10 |
| Salmonella | Not Detected/25 g | Not detected | Not detected | Not detected |
| E. coli | <10 CFU/g | <10 | <10 | <10 |
| Total coliforms | ≤30 CFU/g | Not detected | Not detected | Not detected |
| Absence of source organism from product | Not detected/mg sample | Not detected | Not detected | Not detected |
| Absence of encoding DNA from product | Not detected #/mg sample | Not detected | Not detected | Not detected |

Example 8: Absence of DNA in Recombinant Pepsin Compositions

In this example, experiments were performed to confirm the absence of transformable DNA in the recombinant pepsin preparation made and isolated from the *Pichia* strain.

Materials: 2× Taq MasterMix from NEB, Primers: 5'GAAGCTGAAGCTCTAGTAAAGGTGCCTCTAG (forward; SEQ ID NO: 12); 5' TGCAACAGGTGCTAGACC-CACCTTGTTGTTAG (reverse; SEQ ID NO: 13). The primers have an annealing temp of 58° C. when using 2× Taq MasterMix); control DNA is the pepsinogen transformation cassette (Example 1).

Figure 7C:
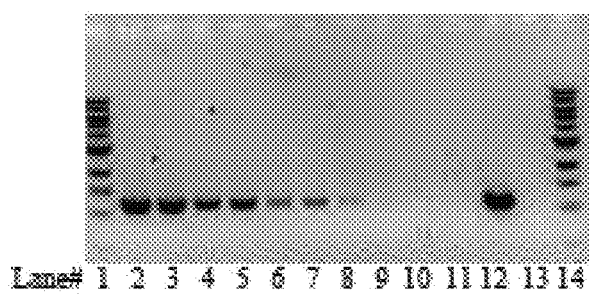

Methods: A pepsin composition in powdered form (see above Examples) was diluted to 100 mg powder/mL in 25 mM sodium hydroxide and then 250 µL was transferred to two new tubes with 250 µL of 25 mM sodium hydroxide (this created two new 500 µL tubes of 50 mg/mL pepsin). To one of these tubes, a positive control pepsinogen plasmid DNA was added to get a final concentration of 1 ng/µL (this served as a positive control for the assay). This tube was then used in sequential dilutions to generate a series of controls with the lowest concentration at 1 fg of control DNA. PCR reactions using the forward and reverse primers (of SEQ ID NOs: 12 and 13) were then performed on the powdered pepsin composition (without control DNA) and the series containing powdered pepsin compositions (with control DNA). PCR products were run on a 1% agarose gel. PCR product for pepsin (as shown in the control lanes) produced a 1122 bp band. This band was absent in each of the three powdered pepsin composition lots tested (see FIG. 7A to FIG. 7C). The detection limit of the assay was about 1 fg of pepsin DNA.

Example 9: Demonstration of Absence of Host Cells in Recombinant Pepsin Compositions Materials: Minimal methanol (MM) agar plates; Potato Glucose Agar (PGA) plates Procedure: Powdered recombinant pepsin compositions were plated on PGA plates. If samples yielded colonies, partial samples of the colony were streaked onto PGA plates and MM plates and incubated as follows: PGA plates for 48 hours at 30° C.; MM plates for 120 hours at 30° C. If colonies grew on MM plates within 120 hours at 30° C., single colonies were picked and colony PCR with cassette specific primers was run. (see PCR method, Example 8). If colony PCR confirmed the presence of the pepsinogen expression cassette, it could be concluded that recombinant *Pichia* cells are present in the pepsin composition.

This procedure was applied to three lots of powdered pepsin composition produced from the recombinant strain (Example 1). No recombinant *Pichia* cells were detected in any of the lots (see Table 3 "source organism" set forth in Example 7).

Example 10: Comparison of the Purity of a Recombinant Pepsin Composition and a Commercially-Available Native Porcine Pepsin A recombinant pepsin composition was compared to native porcine Pepsin A by liquid chromatography tandem mass spectrometry (LC-MS/MS). The protein samples were first digested into peptides using endoproteinase GluC or chymotrypsin, in parallel, to get improved cleavage of Pepsin A. The peptides produced were analyzed through LC-MS/MS. The resulting spectra were matched to peptide sequences using the software tool, X!tandem (see the World Wide Web at: proteomics.ucdavis.edu/protein-identification/). A summary of the proteins present by category is shown in Table 4. The results from the chymotrypsin digest are presented in Table 5.

TABLE 4

Protein abundance and impurities (non-target proteins)
Values shown are for Exponentially Modified Protein Abundance Index (emPAI)

| Accession Number | Porcine Pepsin | Recombinant Pepsin |
|---|---|---|
| Porcine Pepsin (PEPA_PIG; SEQ ID NO: 10) | 826.8 | 1280.1 |
| Pig protein (I3LL32_PIG) | 822.8 | 0.0 |
| Pig Protein (F1S636_PIG) | 491.4 | 0.0 |
| Miscellaneous proteins | 18.9 | 12.7 |

The LC-MS/MS data for the recombinant pepsin exactly matched the mature form of native *Sus scrofa* (Porcine) Pepsin A (PEPA_PIG; SEQ ID NO 10).

Figure 8:
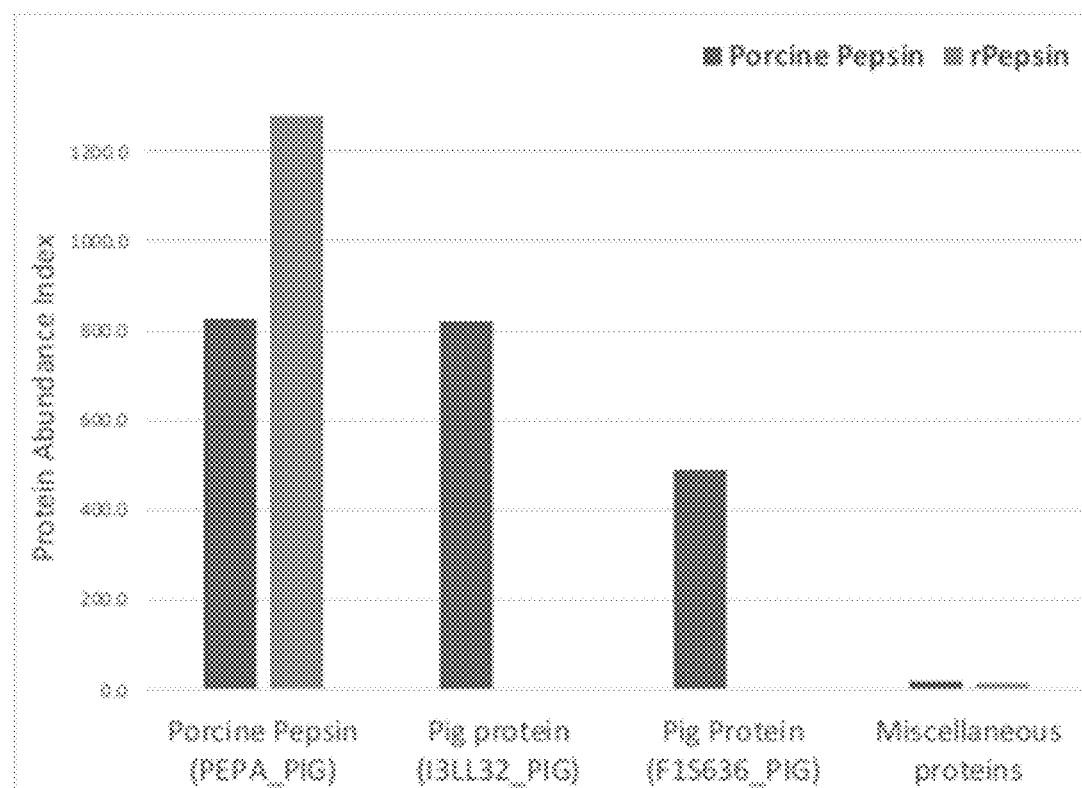
FIG. 8 shows a graph showing the lack of animal derived proteins in the recombinant pepsin composition as compared to a commercially-available native porcine pepsin.

Based on the LC-MS/MS results, recombinant pepsin ("rPepsin") was found to contain an abundance of the PEPA_PIG porcine pepsin sequence (Table 4 and FIG. 8).

The native porcine pepsin contained PEPA_PIG protein and other contaminating porcine proteins in high abundance whereas the recombinant pepsin compositions did not have as many protein impurities (Table 5 and FIG. 8).

TABLE 5

| | LC-MS/MS Protein Abundance data | | | |
|---|---|---|---|---|
| Identified Proteins | Accession Number | Mol. Wt (kDa) | Porcine Pepsin | Recombinant pepsin |
| Cluster of Pepsin A OS = Sus scrofa OX = 9823 GN = PGA PE = 1 SV = 3 (PEPA_PIG; SEQ ID NO: 10) | PEPA_PIG [2] | 41 | 826.8 | 1280.1 |
| Cluster of Chymotrypsinogen A OS = Bos taurus PE = 1 SV = 1 (CTRA_BOVIN) | CTRA_BOVIN [3] | 26 | 275.3 | 1273.6 |
| Uncharacterized protein OS = Sus scrofa OX = 9823 GN = CHIA PE = 3 SV = 2 | I3LL32_PIG | 52 | 822.8 | 0.0 |
| Uncharacterized protein OS = Sus scrofa OX = 9823 GN = LOC 100620249 PE = 3 SV = 2 | F1S636_PIG | 44 | 491.4 | 0.0 |
| Lectin-like protein with similarity to Flo 1p, thought to be expressed and involved in flocculation OS = Komagataella phaffii (strain GS115/ATCC 20864) OX = 644223 GN = PAS_chr1-4_0584 PE = 4 SV = 1 | C4QYW7_KOMPG | 51 | 0.0 | 6.9 |
| Cluster of Uncharacterized protein OS = Sus scrofa OX = 9823 GN = LOC100153899 PE = 1 SV = 1 (FISCD0_PIG) | FISCD0_PIG [2] | 47 | 6.7 | 0.0 |
| Cluster of Uncharacterized protein OS = Sus scrofa OX = 9823 GN = LOC100153899 PE = 1 SV = 1 (AOA287AVA9_PIG) | AOA287AVA9_PIG [3] | 47 | 3.4 | 0.0 |
| Cluster of Fibrillin-1 OS = Sus scrofa OX = 9823 GN = FBN1 PE = 1 SV = 3 (F1SN67_PIG) | F1SN67_PIG [2] | 312 | 0.3 | 0.0 |
| Uncharacterized protein OS = Sus scrofa OX = 9823 GN = MUC5AC PE = 1 SV = 1 | AOA287ANG4_PIG | 440 | 0.1 | 0.0 |
| Gastricsin OS = Sus scrofa OX = 9823 GN = PGC PE = 3 SV = 1 | AOA286ZP41_PIG (+1) | 43 | 3.6 | 0.0 |
| Uncharacterized protein OS = Sus scrofa OX = 9823 GN = LOC100621820 PE = 3 SV = 2 | I3LHI7_PIG | 28 | 1.7 | 0.0 |
| Contains GLEYA adhesin domain OS = Komagataella phaffii (strain GS115/ATCC 20864) OX = 644223 GN = PAS_c034_0002 PE = 4 SV = 1 | C4R9C9_KOMPG | 110 | 0.0 | 0.3 |
| Fibrillin 2 OS = Sus scrofa OX = 9823 GN = FBN2 PE = 1 SV = 3 | F1RKK1_PIG | 303 | 0.1 | 0.0 |
| Mucin 6, oligomeric mucus/gel-forming OS = Sus scrofa OX = 9823 GN = MUC6 PE = 4 SV = 2 | I3LQZ3_PIG | 200 | 0.1 | 0.0 |
| Cluster of Fibrillin 3 OS = Sus scrofa OX = 9823 GN = FBN3 PE = 1 SV = 2 (I3LI73_PIG) | I3LI73_PIG [2] | 304 | 0.0 | 0.0 |
| Uncharacterized protein OS = Komagataella phaffii (strain GS115/ATCC 20864) OX = 644223 GN = PAS_chr3_0016 PE = 4 SV = 1 | C4R3B1_KOMPG | 41 | 0.0 | 1.7 |
| Uncharacterized protein OS = Sus scrofa OX = 9823 GN = CTRB2 PE = 3 SV = 1 | I3LJ52_PIG | 28 | 0.5 | 0.0 |
| Phosphatidylglycerol/phosphatidylinositol transfer protein OS = Komagataella phaffii (strain GS115/ATCC 20864) OX = 644223 GN = PAS_FragB_0077 PE = 4 SV = 1 | C4QZC2_KOMPG | 19 | 0.0 | 2.7 |
| Serpin family F member 2 OS = Sus scrofa OX = 9823 GN = SERPINF2 PE = 1 SV = 1 | A0A287AJI4_PIG (+1) | 53 | 0.2 | 0.0 |
| Essential component of the nuclear pore complex OS = Komagataella phaffii (strain GS115/ATCC 20864) OX = 644223 GN = PAS_chr3_0524 PE = 4 SV = 1 | C4R4T7_KOMPG | 105 | 0.1 | 0.0 |
| Tripeptidyl peptidase 1 OS = Sus scrofa OX = 9823 GN = TPP1 PE = 1 SV = 1 | A0A287AM42_PIG (+2) | 62 | 0.3 | 0.0 |
| Uncharacterized protein OS = Sus scrofa OX = 9823 GN = SERPINA3-2 PE = 1 SV = 1 | F6Q469_PIG | 46 | 0.8 | 0.0 |
| Uncharacterized protein OS = Komagataella phaffii (strain GS115/ATCC 20864) OX = 644223 GN = PAS_chr3_0030 PE = 4 SV = 1 | C4R3C4_KOMPG | 63 | 0.0 | 0.1 |

TABLE 5-continued

| | LC-MS/MS Protein Abundance data | | | |
|---|---|---|---|---|
| Identified Proteins | Accession Number | Mol. Wt (kDa) | Porcine Pepsin | Recombinant pepsin |
| Uncharacterized protein OS = Sus scrofa OX = 9823 GN = LOC396684 PE = 1 SV = 1 | A0A287BM11_PIG (+1) | 45 | 0.7 | 0.0 |
| Thioredoxin OS = Komagataella phaffii (strain GS115/ATCC 20864) OX = 644223 GN = PAS_chr4_0284 PE = 3 SV = 1 | C4R7E5_KOMPG | 11 | 0.0 | 0.9 |
| Ribonuclease K3 OS = Sus scrofa OX = 9823 GN = RNASE6 PE = 1 SV = 2 | RNAS6_PIG | 17 | 0.4 | 0.0 |

Without wishing to be bound by theory, the methods for manufacturing the pepsin compositions of the present disclosure provide a highly active product which is free from animal-derived proteins, and with low (or no detectable) amounts of host cell proteins.

Example 11: Analysis of Stability of a Powdered Recombinant Pepsin Composition

The objective of this analysis was to determine the stability of a powdered recombinant composition. Here, a composition was diluted with common salt, under room temperature and refrigerated storage conditions.

Material and Methods:

Sample preparation: a powdered recombinant pepsin composition (Lot #PEP19225) was diluted with sodium chloride (Micro powder salt flour, The Great American Spice Company) to achieve an activity of 10000 FCC Units/mg powder. After thorough mixing, the diluted composition was aliquoted into 25 Kraft barrier pouches (FDA and USDA compliant) and sealed.

One pouch was sent for analysis for baseline data (Time Point TP 0). Twelve pouches were stored at about 4° C. and another twelve were stored at room temperature. Samples were pulled from each of the two storage conditions at monthly intervals and sent for analyses.

Tests Conducted:
1. Activity (FCC Units/mg powder) following the Pepsin Assay method by *Food Chemical Codex, 9th ed.* (Pharmacopeial Convention. 2014).
2. Moisture % using method AOAC 925.09, Association of Official Analytical Chemists (1995). In Official Methods of Analysis.
3. Aerobic Plate Count using method AOAC 990.12 (AOAC International (2005). Aerobic plate count in foods, dry rehydratable film, method 990.12. AOAC International, 17th ed. Gaithersburg, Md.)
4. Yeast and mold using 17.2.09 AOAC Official Method 997.02. Yeast and Mold Counts in Foods Dry Rehydratable Film Method (Petrifilm™ Method) First Action 1997 Final Action 2000

Results for the first seven months of the room temperature (18° C. to 20° C.) study are shown below in Table 6 and results for the first five months of the refrigerated (~4° C.) study are shown below in Table 7.

TABLE 6

| Time Point | Method | Specification | 0 | 1 | 2 | 3 | 4 | 5 | 6 | 7 |
|---|---|---|---|---|---|---|---|---|---|---|
| Activity (FCC Units/mg powder) | FCC Pepsin Assay | 10000 (FCC/mg powder) | 10708 | 10722 | 9218 | 9512 | 10412 | 10746 | 11974 | 10996 |
| Aerobic Plate Count | AOAC 990.12 | <10000 CFU/g | 20 | <10 | 20 | 20 | <10 | <10 | <10 | 15 |
| Yeast | AOAC 997.02 | <100 CFU/g | <10 | <10 | <10 | <10 | <10 | <10 | <10 | <10 |
| mold | AOAC 997.02 | <100 CFU/g | <10 | 10 | <10 | <10 | <10 | <10 | <10 | <10 |
| Moisture | AOAC 925.09 | <10% | 4.5 | n/a | 5.2 | 4.75 | 4.45 | 4.57 | 4.6 | 4.98 |

TABLE 7

| Time Point | Method | Specification | 0 | 1 | 2 | 3 | 4 | 5 | 6 | 7 |
|---|---|---|---|---|---|---|---|---|---|---|
| Activity (FCC/mg powder) | FCC Pepsin Assay | 10000 (FCC/mg powder) | 10708 | 11188 | 10070 | 10040 | 10452 | 10270 | 11512 | 11044 |
| TPC | AOAC 990.12 | <10000 CFU/g | 20 | 40 | <10 | 65 | <10 | <10 | <10 | 20 |
| Yeast | AOAC 997.02 | <100 CFU/g | <10 | <10 | <10 | <10 | <10 | <10 | <10 | <10 |

TABLE 7-continued

| Time Point | Method | Specification | 0 | 1 | 2 | 3 | 4 | 5 | 6 | 7 |
|---|---|---|---|---|---|---|---|---|---|---|
| mold | AOAC 997.02 | <100 CFU/g | <10 | <10 | <10 | <10 | <10 | <10 | <10 | <10 |
| moisture | AOAC 925.09 | <10% | 4.5 | n/a | 4.7 | 4.47 | 3.98 | 3.93 | 4.0 | 4.53 |

These data show that the microbial load on the samples over the first seven months was well within acceptable limits for both refrigerated and room temperature storage conditions. The recombinant pepsin activity was stable for at least seven months under refrigerated storage and at room temperature.

Without wishing to be bound by theory, the methods for manufacturing the powdered pepsin compositions of the present disclosure provide a highly stable product.

Example 12: Analysis of Stability of a Liquid Recombinant Pepsin Composition

The objective of this analysis was to determine the stability of a liquid recombinant composition. Here, a composition was diluted with phosphate citrate buffer, under refrigerated storage conditions over a period of time.

Material and Methods:

A powdered recombinant pepsin composition (GRAS Test Lot #2 (CS462) was obtained and diluted in 0.01 M phosphate citrate buffer, pH 6.0, to produce a composition comprising 1% recombinant pepsin. The composition was aliquoted into 50 ml conical tube and stored in a 4° C. refrigerator.

Samples were collected every two weeks and pepsin activity was assayed; using an assay based on the Worthington Pepsin Assay: hemoglobin substrate, pH 1.6, 37° C., 10 minutes.

Figure 9:
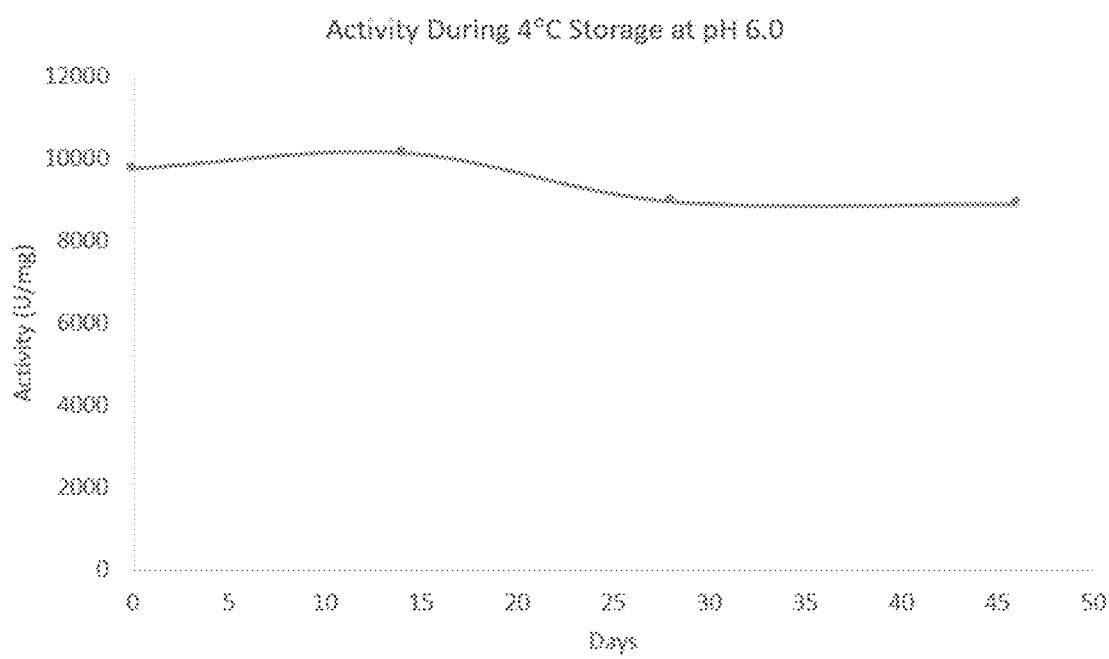
FIG. 9 shows a graph characterizing stability of a liquid recombinant pepsin composition over time.

Data is shown below in Table 8 and FIG. 9.

TABLE 8

| Days | Activity at 4° C. (U/mg) |
|---|---|
| 0 | 9757 |
| 14 | 10135 |
| 28 | 8970 |
| 46 | 8898 |

These data show that the liquid recombinant pepsin composition had maintained activity within the variation of the pepsin activity assay (15%) over the course of 46 days at 4° C. Thus, the recombinant pepsin composition can be considered liquid-stable at pH 6.

Without wishing to be bound by theory, the methods for manufacturing the liquid pepsin compositions of the present disclosure provide a highly stable product.

While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A consumable composition comprising a recombinant pepsin polypeptide and at least one consumable ingredient, wherein (a) the consumable composition is free from animal-derived proteins, (b) the recombinant pepsin polypeptide is in a proteolytically inactive form which does not self-digest, and (c) the recombinant pepsin polypeptide, when active, has a specific activity of from 500 FCC units/mg total protein to 50,000 FCC units/mg total protein.

2. The consumable composition of claim 1, wherein the composition comprising the proteolytically inactive pepsin polypeptide form which does not self-digest is stable for at least 6 months at room temperature or for at least 6 months at 4° C.

3. The consumable composition of claim 2, wherein the composition has a moisture content of less than about 10%.

4. The consumable composition of claim 1, wherein the recombinant pepsin polypeptide has a specific activity of from 500 FCC units/mg total protein to 20,000 FCC units/mg total protein at pH 2.

5. The consumable composition of claim 1, wherein the proteolytically inactive pepsin polypeptide form which does not self-digest is stable in a liquid composition for at least 30 days at a temperature of 4° C.

6. The composition of claim 1, wherein the recombinant pepsin polypeptide comprises an amino acid sequence of a sheep, pig, cow, human, zebu, yak, Central European red deer, or goat pepsin.

7. The composition of claim 1, wherein the recombinant pepsin polypeptide comprises SEQ ID NO: 10, or an amino acid sequence with at least 90% identity thereto.

8. The composition of claim 1, wherein the recombinant pepsin polypeptide is produced in a *Pichia* species, a yeast, a filamentous fungus, a *Saccharomyces* species, a bacterium, a *Trichoderma* species, or an *Aspergillus* species.

* * * * *